(12) United States Patent
Ahmed et al.

(10) Patent No.: US 12,329,992 B2
(45) Date of Patent: Jun. 17, 2025

(54) EBOLA VIRUS ANTIBODIES AND BINDING AGENTS DERIVED THEREFROM

(71) Applicants: Emory University, Atlanta, GA (US); The Scripps Research Institute, La Jolla, CA (US)

(72) Inventors: Rafi Ahmed, Atlanta, GA (US); Carl Davis, Atlanta, GA (US); Erica Ollmann Saphire, Solana Beach, CA (US)

(73) Assignees: Emory University, Atlanta, GA (US); The Scripps Research Institute, La Jolla, CA (US)

( * ) Notice: Subject to any disclaimer, the term of this patent is extended or adjusted under 35 U.S.C. 154(b) by 6 days.

(21) Appl. No.: 18/332,291

(22) Filed: Jun. 9, 2023

(65) Prior Publication Data

US 2023/0303667 A1    Sep. 28, 2023

Related U.S. Application Data

(63) Continuation of application No. 17/196,418, filed on Mar. 9, 2021, now Pat. No. 11,713,349, which is a continuation of application No. 16/319,775, filed as application No. PCT/US2017/043305 on Jul. 21, 2017, now abandoned.

(60) Provisional application No. 62/364,986, filed on Jul. 21, 2016.

(51) Int. Cl.
*A61P 31/14*     (2006.01)
*C07K 16/10*    (2006.01)
*C12Q 1/70*     (2006.01)

(52) U.S. Cl.
CPC .............. *C07K 16/10* (2013.01); *A61P 31/14* (2018.01); *C12Q 1/701* (2013.01); *C07K 2317/21* (2013.01); *C07K 2317/24* (2013.01); *C07K 2317/524* (2013.01); *C07K 2317/71* (2013.01); *C07K 2317/72* (2013.01); *C07K 2317/76* (2013.01); *C07K 2317/92* (2013.01)

(58) Field of Classification Search
CPC ... A61K 2039/505; A61P 31/14; C07K 16/10; C07K 2317/524; C07K 2317/72; C07K 2317/71; C07K 2317/92; C07K 2317/76
See application file for complete search history.

(56) References Cited

U.S. PATENT DOCUMENTS

| 11,713,349 | B2 | 8/2023 | Ahmed |
| 2008/0069822 | A1 | 3/2008 | Jensen |
| 2015/0125455 | A1 | 5/2015 | Green |
| 2015/0344546 | A1 | 12/2015 | Jones |
| 2016/0215040 | A1 | 7/2016 | Kyratsous |

FOREIGN PATENT DOCUMENTS

| WO | 2001016183 | 3/2001 |
| WO | 2016075546 | 5/2016 |
| WO | 2021150829 | 7/2021 |

OTHER PUBLICATIONS

Brown et al. Tolerance to Single, but Not Multiple, Amino Acid Replacements in Antibody VH, CDR2, Journal of Immunology, 1996, 156: 3285-3291.
Casset et al. A peptide mimetic of an anti-CD4 monoclonal antibody by rational design, Biochemical and Biophysical Research Communications 307 (2003) 198-205.
Corti et al. Protective monotherapy against lethal Ebola virus infection by a potently neutralizing antibody, Science, 2016, vol. 351 Issue 6279.
Davidson et al. Mechanism of Binding to Ebola Virus Glycoprotein by the ZMapp, ZMAb, and MB-003 Cocktail Antibodies, J Virol, 2015, 89:10982-10992.
Davis et al. Longitudinal Analysis of the Human B Cell Response to Ebola Virus Infection, Cell, 2019, 177(6):1566-1582.e17.
Flyak et al. Cross-Reactive and Potent Neutralizing Antibody Responses in Human Survivors of Natural Ebolavirus Infection, Cell, 2016, 164(3): 392-405.
Furuyama et al. Discovery of an antibody for pan ebolavirus therapy, Sci Rep. 2016, 6: 20514.
Geisbert et al. Ebola therapy protects severely ill monkeys, Nature. 2014, 514(7520): 41-43.
Geisbert et al. Considerations in the Use of Nonhuman Primate Models of Ebola Virus and Marburg Virus Infection, J Infect Dis, 2015, 212 Suppl 2(Suppl 2):S91-7.
Gregory et al. Structure and function of the complete internal fusion loop from Ebolavirus glycoprotein 2, PNAS, 2011, vol. 108, No. 27, 11211-11216.
Hernandez et al. Development and Characterization of Broadly Cross-reactive Monoclonal Antibodies Against All Known Ebolavirus Species, J Infect Dis, 2015, 212 Suppl 2(Suppl 2):S410-3.
Hoenen et al. Current Ebola vaccines, Expert Opin Biol Ther, 2012, 12(7): 859-872.
Holtsberg et al. Pan-ebolavirus and Pan-filovirus Mouse Monoclonal Antibodies: Protection against Ebola and Sudan Viruses, 2016, J Virol, 90:266-278.
Keck et al., Macaque Monoclonal Antibodies Targeting Novel Conserved Epitopes within Filovirus Glycoprotein, J Virol, 2016, 90:279-291.
MacCallum et al. Antibody-antigen Interactions: Contact Analysis and Binding Site Topography, J. Mol. Biol. (1996) 262, 732-745.
Martinez et al. Impact of Ebola Mucin-Like Domain on Antiglycoprotein Antibody Responses Induced by Ebola Virus-Like Particles, J Infect Dis, 2011, 204 Suppl 3(Suppl 3):S825-32.
McElroy et al. Human Ebola virus infection results in substantial immune activation, Proc Natl Acad Sci U S A, 2015, 112(15):4719-24.
Mohan et al. Less Is More: Ebola Virus Surface Glycoprotein Expression Levels Regulate Virus Production and Infectivity, J Virol , 2015, 89:1205-1217.

(Continued)

*Primary Examiner* — Bao Q Li
(74) *Attorney, Agent, or Firm* — Emory Patent Group

(57) ABSTRACT

This disclosure relates to antibodies and antigen binding fragments that specifically bind Ebola virus particles. In certain embodiments, the antibodies and fragments are capable of treating or preventing an Ebola viral infection. In certain embodiments, the antibodies and antigen binding fragments are also contemplated for diagnostic methods and compositions related thereto.

11 Claims, 8 Drawing Sheets

Specification includes a Sequence Listing.

(56) References Cited

OTHER PUBLICATIONS

Moller et al. Ebola Virus Entry: A Curious and Complex Series of Events, PLoS Pathog, 2015, 11(4): e1004731.

Murin et al. Structures of protective antibodies reveal sites of vulnerability on Ebola virus, Proc Natl Acad Sci U S A, 2014, 111 48):17182-17187.

Pascal et al. Development of Clinical-Stage Human Monoclonal Antibodies That Treat Advanced Ebola Virus Disease in Nonhuman Primates, the Journal of Infectious Diseases, 2018;218(S5):S612-26.

Pascalis et al. Grafting of "Abbreviated" Complementarity-Determining Regions Containing Specificity-Determining Residues Essential for Ligand Contact to Engineer a Less Immunogenic Humanized Monoclonal Antibody, Journal of Immunology, 2002, 169: 3076-3084.

Riechmann et al. Reshaping human antibodies for therapy, Nature, 1988, 332(6162):323-7.

Vajdos et al. Comprehensive Functional Maps of the Antigen binding Site of an Anti-ErbB2 Antibody Obtained with Shotgun Scanning Mutagenesis, J. Mol. Biol. (2002) 320, 415-428.

Zhang et al. Potent neutralizing monoclonal antibodies against Ebola virus infection, Sci Rep, 2016, 6, 25856.

| Antibody name | cell source | VH nucleotide sequence | VL nucleotide sequence | VH amino acid sequence | VL amino acid sequence | original isotype |
|---|---|---|---|---|---|---|
| 5.1.1083 | bulk GP negative plasmablast | GAGGTGCAGCTGGTGGAGTCTGGGGGAGGCTTGGTACAGCCTGGGGGGTCCCTGAGACTCTCCTGTGCAGCCTCTGGATTCACCTTCAGAAGCTACGACATGCACTGGGTCCGCCAAGCTACAGGAAAAGGTCTGGAGTGGGTCTCAGCTATTGGTACTGCTGGTGACACATACTATCCAGGCTCCGTGAAGGGCCGATTCACCATCTCCAGAGAAAATGCCAAGAACTCCTTGTATCTTCAAATGAACAGCCTGAGAGCCGAGGACACGGCCGTGTATTACTGTGCAAGAGTCCGTTTCGGGGATACAGCCGTTGACTACTGGGGCCAGGGAACCCTGGTCACCGTCTCCTCAGC SEQ ID NO: 52 | GACATCCAGATGACCCAGTCTCCATCCTCCCTGTCTGCATCTGTAGGAGACAGAGTCACCATCACTTGCCGGGCAAGTCAGAGCATTAGCAGCTTTTTAAATTGGCATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAATTTACTACTGTCAACAGAGTTACATTTCCCCATTCACTTTCGGCCCTGGGACCAAAGTGGATATCAAA SEQ ID NO: 51 | EVQLVESGGGLVQPGGSLRLSCAASGFTFRSYDMHWVRQATGKGLEWVSAIGTAGDTYYPGSVKGRFTISRENAKNSLYLQMNSLRAEDTAVYYCARVRFGDTAVDYWGQGTLVTVSS SEQ ID NO: 2 | DIQMTQSPSSLSASVGDRVTITCRASQSISSFLNWHQQKPGKAPKLLIYAASSLQSGVPSRFSGSGSGTDFTLTISSLQPEDFAIYYCQQSYISPFTFGPGTKVDIK SEQ ID NO: 1 | IgG1, kappa |
| 3.6.1ACI | GP binding B cells | GAGGTGCAGCTGGTGGAGTCAGGAGGAGGCTTGATCCAGCCTGGGGGGTCCCTGAGACTCTCCTGTGCAGCCTCTGGTTTCGCCGTCAGGAGCAACTACTTGAGCTGGGTCCGCCAGGCTCCTGGGAAGGGGCTGGAGTGGGTCTCACTTATTTATAGTGGTGGTCTCACAGCCTACGCAGACTCCGTGAAGGGCCGGTTCACCATCTCCAGAGACAATTCTAAGAACACACTATATCTTCAAATGAACAGCCTGAGAGTCGAGGACACGGCCCTATATTACTGTGCGAGAGTCGCATCATCGGCTGGAACCTTCTACTACGGTATGGACGTCTGGGGCCAAGGGACCACGGTCACCGTCTCCTCAGC SEQ ID NO: 54 | GATATTGTGATGACTCAGTCTCCACGCTCCCTGTCCGTCACCCCTGGAGAGCCGGCCCTCCATCTCCTGCAGGTCTAGTCAGAGCCTCCTGCATAGAAATGGATATAACTATTTGGATTGGTATCTGCAGAAGCCAGGGCAGTCTCCACAGCTCCTGATCTATTTGGGTTCTAATCGGGCCTCCGGGGTCCCTGACAGGTTCAGTGGCAGTGGATCAGGCACAGATTTTACACTGAAAATCAGCAGAGTGGAGGCTGAAGATGTTGGGGTTTATTACTGCATGCAAGCTCTACAAACTCCCTCGTGGACGTTCGGCCAAGGGACCAAGGTGGAAATCAAA SEQ ID NO: 53 | EVQLVESGGGLIQPGGSLRLSCAASGFAVRSNYLSWVRQAPGKGLEWVSLIYSGGLTAYADSVKGRFTISRDNSKNTLYLQMNSLRVEDTALYYCARVASSAGTFYYGMDVWGQGTTVTVSS SEQ ID NO: 4 | DIVMTQSPRSLSVTPGEPASISCRSSQSLLHRNGYNYLDWYLQKPGQSPQLLIYLGSNRASGVPDRFSGSGSGTDFTLKISRVEAEDVGVYYCMQALQTPSWTFGQGTKVEIK SEQ ID NO: 3 | IgG1, kappa |

FIG. 2

| | | | | | | |
|---|---|---|---|---|---|---|
| 2.1.1D05 | GP binding B cells | GAGGTGCAGCTGGTGGAGTCTGGGGGAGGCTTGGTAAAACCTGGGGGGTCCCTTAGACTCTCCTGTGCAGCCTCTGGATTCACTTTCAGTAACGCCTGGATGAACTGGGTCCGCCAGGCTCCAGGGAAGGGGCTGGAGTGGGTTGGCCGTATTAAGAGCAAAACTGATGGTGGGGCTGCAGACTACGCTGCACCCGTGAAGGGCAGATTCACCATCTCAAGAGATGATTCAAAAAACACGCTGTATCTGCAAATGAACAGCCTGAAAACCGAGGACACAGCCGTGTATTTCTGTACCACAGTCTACAGATACAACTATGATTCCGTCTGGGGCCAGGGAACCCTGGTCACCGTCTCCTCAGC<br>SEQ ID NO: 56 | CAGTCTGTGCTGACGCAGCCGCCCTCAGTGTCTGGGGCCCCAGGGCAGAGGGTCACCATCTCCTGCACTGGGAGCAGTTCCAACATCGGGGCAGGTTATGATGTATACTGGTACCAGCAGCTTCCAGGAACAGCCCCCAAACTCCTCATCTATGGTAACAGCAATCGGCCCTCAGGGGTCCCTGACCGATTCTCTGGCTCCAAGTCTGGCACCTCAGCCTCCCTGGCCATCACTGGGCTCCAGGCTGAGGATGAGGCTGATTACTACTGCCAGTCCTTTGACAGCAGCCTGAGAGATTCTTGGGTGTTCGGCGGGGGGACCAAGCTGACCGTCCTA<br>SEQ ID NO: 55 | EVQLVESGGGLVKPGGSLRLSCAASGFTFSNAWMNWVRQAPGKGLEWVGRIKSKTDGGAADYAAPVKGRFTISRDDSKNTLYLQMNSLKTEDTAVYFCTTVYRYNYDSVWGQGTLVTVSS<br><br>SEQ ID NO: 6 | QSVLTQPPSVSGAPGQRVTISCTGSSSNIGAGYDVYWYQQLPGTAPKLLIYGNSNRPSGVPDRFSGSKSGTSASLAITGLQAEDEADYYCQSFDSSLRDSWVFGGGTKLTVL<br><br>SEQ ID NO: 5 | IgG1, lambda |
| 2.1.1D07 | GP binding B cells | GAGGTGCAGCTGTTGGAGTCTGGGGGAGGCTTGGTACAGCCTGGGGGGTCCCTGAGACTCTCCTGTGCAGCCTCTGGATTCACCTTTAGCACCTATGGCATGAGCTGGGTCCGCCAGGCTCCAGGGAAGGGGCTGGAGTGGGTCTCAGGTATTAGTGGTAGTGGTGGTATCACATACTACGCAGACTCCGTGAGGGGCCGGTTCACCATCTCCAGAGACAATTCCAAGAACACGCTGTATCTGCAAATGAACAGCCTGAGAGCCGAGGACACGGCCGTATATTACTGTGCGAAAGTGGGGGAGTATTACGATTTTTGGAGTGGTTATTCCCCCTTTGAATACTGGGGCCAGGGAACCCTGGTCACCGTCTCCTCAGC<br>SEQ ID NO: 58 | GAAATTGTGTTGACGCAGTCTCCAGGCACCCTGTCTTTGTCTCCAGGGGAAAGAGCCACCCTCTCCTGCAGGGCCAGTCAGAGTGTTAGCAGCAGCTACTTAGCCTGGTACCAGCAGAAACCTGGCCAGGCTCCCAGGCTCCTCATCTATGGTGCATTTAACAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCTGTATGGTAGCTCACCGTGGACGTTCGGCCAAGGGACCAAGGTGGAAATCAAA<br>SEQ ID NO: 57 | EVQLLESGGGLVQPGGSLRLSCAASGFTFSTYGMSWVRQAPGKGLEWVSGISGSGGITYYADSVRGRFTISRDNSKNTLYLRMNSLRAEDTAVYYCAKVGEYYDFWSGYSPFEYWGQGTL<br><br>SEQ ID NO: 8 | EIVLTQSPGTLSLSPGERATLSCRASQSVSSSYLAWYQQKPGQAPRLLIYGAFNRATGIPDRFSGSGSGTDFTLTISRLEPEDFAVYYCQLYGSSPWTFGQGTKVEIK<br><br>SEQ ID NO: 7 | IgG1, kappa |

FIG. 3

| | | | | | |
|---|---|---|---|---|---|
| 9.6.3D06 | GP binding B cells | GAGGTGCAGCTGTTGGAGTCTGGGGGAGGCCTGGTACAGCCGGGGGGGTCCCTGAGACTCTCCTGTGCCGCCTCTGGATTCACCTTTAGCAAATATGCCATGATCTGGGTCCGCCAGGCCCCAGGGAAGGGGCTGCAGTGGGTGGCAGGTATTAATAAGAGTGGTGGCAGGACATACTACGCAGACTCCGTGAGGGGCCGGTTCACCATCTCCAGAGACAATTCCAAGAATACGCTGTACCTGCAAATGAAAAGCCTGAGAGCCGACGACACGGCCATGTATTACTGTGCGAAAGAGGGATCCCCTTTATCAGATGTTTTACTGGTAGCAGCTCCATTTGGGTGGTTCGATCCCTGGGGCCAGGGAACCCTGGTCACCGTCTCCTCAGC<br>SEQ ID NO: 60 | GACATCCAGATGACCCAGTCTCCTTCCACCCTGTCTGCATCTGTAGGAGACAGAGTCACCATCACTTGCCGGGCCAGTCAGAGGATTAATAATTTGGTGGCCTGGTATCAGCAGAAACCAGGGAAAGCCCCTAAGGTCATGATCTATGATGCCTCCAGTTTGAAAAGTGGGGTCCCATCAAGGTTCAGCGGCAGTGGATCTGGGACAGAATTCACTCTCACCATCAGCAGCCTGCAACCTGATGATTTTGCAACTTATTTCTGCCAACAGTATGATACTGATTCGGGGTGGACGTTCGGCCAAGGGACCAAGGTGGAAATCAAA<br>SEQ ID NO: 59 | EVQLLESGGGLVQPGGSLRLSCAASGFTFSKYAMIWVRQAPGKGLQWVAGINKSGGRTYYADSVRGRFTISRDNSKNTLYLQMKSLRAEDTAMYYCAKEGSPLSDVLLVAAPFGWFDPWGQGTLVTVSS<br><br>SEQ ID NO: 10 | DIQMTQSPSTLSASVGDRVTITCRASQRINNLVAWYQQKPGKAPKVMIYDASSLKSGVPSRFSGSGSGTEFTLTISSLQPDDFATYFCQQYDTDSGWTFGQGTKVEIK<br><br>SEQ ID NO: 9 | IgA1, kappa |

FIG. 4

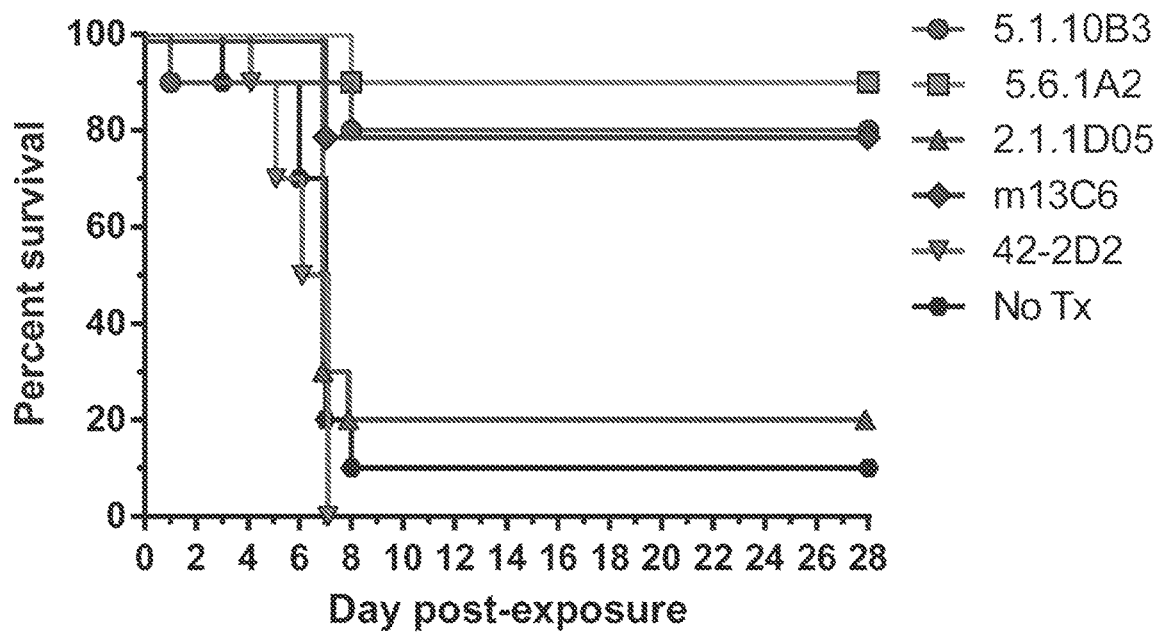

FIG. 5

| mAb name | Heavy chain nucleotide sequence | Light chain nucleotide sequence |
|---|---|---|
| 2.1.1B02 | GAGGTGCAGCTGGTGCAGTCTGGGGCTGAGGTGAAGAAGCCTGGGGCCTCAGTGAAGGTTTCCTGCAAGGCATCTGGATACACCTTCACCAGCTACTATATGCACTGGGTGCGACAGGCCCCTGGACAAGGGCTTGAGTGGATGGGAATAATCAACCCTAGTGGTGGTAGCACAAGCTACGCACAGAAGTTCCAGGGCAGAGTCACCATGACCAGGGACACGTCCACGAGCACAGTCTACATGGAGCTGAGCAGCCTGAGATCTGAGGACACGGCCGTGTATTACTGTGCTAGGCATGATAGTAGTGGTTATGATGCTTTTGATATCTGGGGCCAAGGGACAATGGTCACCGTCTCTTCA SEQ ID NO: 197 | TCCTATGAGCTGACACAGCCACCCTCGGTGTCAGTGTCCCCAGGACAGACGGCCAGGATCACCTGCTCTGGAGATGCATTGCCAAAGCAATATGCTTATTGGTACCAGCAGAAGCCAGGCCAGGCCCCTGTGCCGGTGATATATAAAGACAGTGAGAGGCCCTCAGGGATCCCTGAGCGATTCTCTGGCTCCAGCTCAGGGACAACAGTCACGTTGACCATCAGTGGAGTCCAGGCAGAAGACGAGGCTGACTATTACTGTCAATCATCAGACAGCAGTGGTACTTATGTGGTATTCGGCGGAGGGACCAAGCTGACCGTCCTA SEQ ID NO: 198 |
| 5.24.1C11 | CAGGTGCAACTGGTGCAGTCAGGGGCTGAGGTGAAGAAGCCTGGGGCCTCAGTGAAGGTTTCCTGCAGGACATCTGGATACACATTCTCCAGCTACAATATACATTGGGTGCGACAGGCCCCTGGACAAGGTCTTGAGTGGATGGGAGTTATTAATCCTTATGGCCGTAGTACCACACTTTACGCACGGAGGTTCCGGGACAGAGTCACCATGACCAGGGACACGTCCACGAGCACAGTTTACATGGAACTGAGCAGCCTGAGATCCGAGGACACGGCCGTATACTTCTGTGGAAGGCTTTACAGTGGTGCACCCTATGGTTTGGACGTCTGGGGCCAAGGGAGCACGGTCACCGTCTCTTCA SEQ ID NO: 199 | GATATTGTGATGACTCAGTCTCCACTCTCCCTGCCCGTCACCCCTGGAGAGCCGGCCTCCATCTCCTGCAGGTCTAGTCAGAGCCTCCTGCATAGTAATGGATACAACTATGTGGATTGGTACCTGCAGAAGCCAGGGCAGTCTCCACAGCTCCTGATCTATTTGGGTTCTAGTCGGGCCTCCGGGGTCCCTGACAGGTTCAGTGGCAGTGGATCAGGCACAGATTTTACACTGAAAATCAGCAGAGTGGAGACTGAGGATGTTGGCATTTATTACTGCATGCAAGGTCTACAAACTCCCCTCACTTTCGGCGGAGGGACCAAGGTGGAGATCAAA SEQ ID NO: 200 |
| 9.20.1C03 | CAGGTGCAGCTGGTGCAGTCTGGGGCTGAAGTGAAGAAGCCTGGGGTCCTCGGTGAAGGTCGCCTGCAAGGTTTCTGGAGGCACCTTCAGCAGCTATACTATTAGTTGGGTGCGACAGGCCCCTGGACAAGGGCTTGAGTGGATGGGAGGGATCATCCCTTCCTTTGGTGTGGGACACTACTCACAGAAGTTCCGGGACAGAGTCACGCTAACCGCGGACAAATCCACGACCACAGCCTTCTTGGAACTGAGCAGCGTGAGATCTGAAGACACGGCCCTATATTACTGTGCGATACTGGGGACTTTAACTGGAAGTCCGGGGGCAACTACTTCGGCCCCTGGGGCCAGGGGACCCTGGTCACCGTCTCTTCA SEQ ID NO: 201 | GACATCGTGCTGACCCAGTCTCCAGACTCCCTGGCTGCGTCTCTGGGCGAGAGGGCCACCATCAGCTGCAAGTCCAGCCACAGTGTTTTATACAGCTCCAACAATAAGGACTTCTTTGCCTGGTACCAGCAGAAACCAGGACAGCCTCCCAAACTGCTCATTTCCTGGGCATCTACCCGGGGAATCCGGGGTCCCTGTCCGATTCAATGGCGGCGGGTCTGGGACACATTTCACTCTCACCATCAGCAGCCTGCAGGCTGAAGATGTGGCAGTTTACTACTGTCAGCAATATTTTAGTTCTCCGATCACCTTCGGCCAAGGGACACGACTGGAGATTAAA SEQ ID NO: 202 |

FIG. 8

| mAb name | Heavy chain nucleotide sequence | Light chain nucleotide sequence |
|---|---|---|
| 5.24.1 B03 | CAGGTGCAGCTGCAGGAGTCGGGCCCAGGACTGGTGAAGCCTTCGGAGAGCCTGTCCCTCACATGCACTATCTCTGGCGGCTCCATAAGGGACTATTACTGGAGCTGGATTCGGCAGGCCCCAGGGAAGGGACTGGAGTGGATCGGATATAAGTATCACGCTGCGCGCGGCAACTCCAATCCCTCCCTCGAGAGTCGAGTCACCATGTCCATCGACACGTCCAGGAGCGAGTTCTCCCTGAGGCTGACTTCTGTGACCGCTGCGGACACGGCCGTCTATTATTGTGCGAGAGTTCAATACGGTCCTGGGGGCGGTTACTATTCGGGGAACTGGTTGGACCTCTGGGGCCAGGGAACCCTGGTCACCGTCTCTTCA SEQ ID NO: 203 | GAAATTGTGTTGACACAGTCTCCAAACACCCTGTCTTTGTCTCCAGGGGAAAGAGCCACCCTCTCCTGCAGGGCCAGTCAGAGTCTTCGTACCAACCAGTTAGCCTGGTACCAGCAAAAACCTGGCCAGGCTCCCAGGCTCCTCATCCATACATCCACCAGGGCCACTGGCATCCCAGCAGGTTCAGTGGCAGTGGGTCTGGGACAGACTTCACTCTCACCATCAGCGGACTGGAGGCTGAAGACTTTGCAGTGTATTACTGTCAGGCGTCTGATACCTCATCGCTCACTTTCGGCGGAGGGACCAAGTTAGAGATCAGA SEQ ID NO: 204 |
| 9.20.1 D09 | CAGCTGCAGCTGCAGGAGTCGGGCCCAGGACTGGTGAAGCCTTCGGAGACCCTGTCCCTCACCTGCACTGTCTCTGGTGGCTCCGTCGCCAGTAGTAATGACTACTGGGGCTGGATCCGCCAGCCCCCAGGGAAGGGGCCGGAGTGGATTGGGACTATCTTTTATAGAGGGACCACCGACTACAACCCGTCCCTCAAGAGTCGACTCACTATGTCCGTGGACACGTCCAGGAACCAGTTCTCCCTGAAGCTGAGCTCTGTGACCGCCGCAGACACGGCTGTCTATTACTGTGCGAGACTGCCCCTATGGTTCAGTGAGTTAGGTCATGACTACTGGGGCCAGGGAACCCTGGTCACCGTCTCCTCA SEQ ID NO: 205 | GAAATAGTGATGACGCAGTCTCCAGCCACCCTGTCTCTGTCTCCAGGAGAAAGAGCCTCCCTGTCCTGCAGGGCCAGTCAGAGTATTGCCACCAACTTAGCCTGGTACCAGCAAAAACCTGGCCAGCCTCCCAGGGTCCTCATCTATGGTGCATCCAAAGGGCAACTGGTATCCCAACCAGGTTCAGTGGCAGTGGATCTGGGACAGAGTTCACTCTCACCATCAGCAGCCTGCAGTCTGAAGATTTTGCAATTTATTACTGTCACCAGTATCATAGCTGGCGGACGTTCGGCCAAGGGACCAAGGTAGAAATGAAA SEQ ID NO: 206 |
| 5.24.2 A03 | CAGGTGCAGCTGCATGAGTCGGGCCCAGGGCTGGTGCAGCCTTCGGAGACCCTGTCCCTCACCTGCACTGTCTCTGGTGACTCCATCACTAATTACTACTGGAGCTGGATCCGGCAGCCCCCAGGGAAGGGACTGGAGTGGATTGGATATATGTATTACAGTGCGAGCGCCCACTACAATCCCTCCCTCCAGAGTCgAGTCACCATTTCAGTGGACACGTCCAAGAACCAGTTCTCCCTGAAACTGAGCTCTGTGACCGCTGCGGACACGGCCGTGTATTTCTGTGCGAGAGTGGACTACAGTTCGAGTAGTTATTATCGGGAAACTGGTTCGACCCCTGGGGCCAGGGAACCCTTGTCACCGTCTCCTCA SEQ ID NO: 207 | CAGTCTGCCCTGACTCAGCCTCCCTCCGCGTCCGGGTCTCTGGACAGTCAGTCACCATCTCCTGCACTGGAACCAGCAGTGACGTTGGTGTTTATAATTCTGTCTCCTGGTACCGACAGCACCCAGGCAAAGTCCCCAAACTCATGATTTATGAGGTCAGTAAGCGGCCCTCAGGGGTCCCTGATCGCTTCTCTGGCTCCAAGTCCGGCAACACGGCCTCCCTGACCGTCTCTGGGCTCCAGGCTGACGATGAGGGTGATTATTACTGCTGCTCATGTTCAGGCACCAACAGCCTCTGTGTCTTCGGAACTGGGACCAAGGTCACCGTCCTG SEQ ID NO: 208 |

FIG. 9

| mAb name | Heavy chain nucleotide sequence | Light chain nucleotide sequence |
|---|---|---|
| 9.20.1 A02 | GAGGTGCAGCTGGTGGAGTCTGGGGGAGACTTAGTACAG CCTGGGGGGTCCCTCAGACTCTCCTGTGCAGCCTCTGGAAT CACCTTGAGTGGAGTTTGGATGAACTGGGTCCGCCAGGCT CCAGGGAAGGGGCTGGAGTGGATTGGCCGTATTAAAAGC ACAAGTGACGGTGGGAGAGCAGACTTCGCCGCACCCGCG AGAGGCAGATTCACCATGTCAAGAGATGAGTCAAAGAAT AAGCTGTTTCTGCAAATGAACAACCTGGGAATCGAAGACA CAGGCATGTATTATTGTTTCACGAGAGTCCAAAGAGACGG AACTAAAGATGACTTCTGGGGCCGGGGAACCCTGGTCACC GTCTCTTCA SEQ ID NO: 209 | CAGTCTGTGCTGACGCAGCCGCCCTCAGTGTCTGGGGCC CCAGGGCAGACGGTCACCATCTCCTGCACTGGGAGCTAC TCCAACATCGGGGCAGGTTATGATGTACAGTGGTACCAG CACCTTCCTGGAACAGCCCCCAAACTCCTCATTTATGATA ATGTCCATCGGCCCTCAGGGGTCCCTGACCGATTCTCTGG CTCCAAGTCTGGCACCTCAGCCTCCCTGGCCATCACTGGG CTCCAGACTGAAGATGAGGCTGATTATTATTGCCAGTCCT ATGACAGCAGACTGAGGGATCAATGGGTGTTCGGCGGA GGGACCAAGCTGACCGTCCTA SEQ ID NO: 210 |
| 5.24.2 C05 | CAGGAGCAGCTGCAAGAGTCGGGCCCAGGACTGGTGAAG CCTTCGGGGACCCTGTCCCTCACCTGCACTGTCTCCGGCGT CTCCGTCAGTGGGAGTTACTTCTGGAATTGGGTCCGCCAGC CCCCAGGGAAGGGACTGGAGTGGCTTGGATTTATTCATAG CACTGGGAGCACCAACACCAACCCCTCCCTCAAGAGTCGA GTCACCATTTCAGTAGACACGTCCAAGAACCAGTTCTCCCT GAGGCTGACTTCTGTGAGCGCTGCGGACACGGCCGTTTATT ACTGTGCGAGAGCCGCTTGGTTAGTAGGGGGGAGTACTA CAACTACGGTATGGACCTTTGGGGCCAAGGGACCACGGTT ACCGTCTCCTCA SEQ ID NO: 211 | CAGTCTGCCCTGACTCAGCCCGCCTCCGTTTCTGGGTCTC CTGGACAGTCGATCACCCTCTCCTGCACTGTAGGCGGTA ATAAGTTTGTCTCTTGGTATCAACAACACCCAGGCAAAG CCCCCAAACTCATTATTTCTGATTTCACTGATCGGCCCTC AGGGGTCTCTAGTCGCTTCTCTGGCTCCAAGTCTGGCAAC ACGGCCTCCCTGACCATCTCTGGGCTCCAGCCTGACGAC GAGGCTACTTATTTCTGCAGTTCTTACGCAAGCACCAGCA CTTCTCTTTGGGTCTTCGGCGGGGGGACCAAGCTGACCGT CCTA SEQ ID NO: 212 |
| 5.24.2 B07 | CAGGTGCAGCTGGTGGAATCTGGGGGAGGCGTGGTCCAG CCTGGGAGGTCCCTGAGACTCTCCTGTGTAGCGTCTGGATT CACCTTCAGTAGTTATGGCATGCACTGGGTCCGCCAGGCTC CAGGCAAGGGGCTGGAGTGGGTGGCATTTATATGGTATGA TGGAACTATTCAATACTATGGAGACTCCGTGAAGGGCCGA TTCATCATCTCCAGAGACAATTCCAGGAATACGCTGTATCT ACAAATGAACAGCCTGAGAGCCGAGGACACGGCTGTGTA TTACTGTGCGAGCACTCTTTACCGAAACGGTGACTACGGGT CAGGGTCCCGGACCCCGGACGACTACTGGGGCCAGGGAA CCCTGGTCACCGTCTCTTCA SEQ ID NO: 213 | GGCATCCAGTTGACCCAGTCTCCATCCTTCCTGTCTGCAT CTGTAGGAGACAGAGTCACCATCACTTGCCGGGCCAGTC AGGGCATTTACACTTATTTAGCCTGGTATCAGCAAAAAC CAGGGAAAGCCCCTAAGCTCCTGGTCTATGTTGCATCCA CTTTGCAAAGTGGGGTCCCATCAAGGTTCAGCGGCAGTG GATCTGGGACAGAATTCACTCTCACAATCAGCAGCCTGC AGCCTGAAGATTTTGCAACTTATTACTGTCAACAGCTTAA TAGTTACCCTCTCACTTTTGGCCAGGGGACCAAGCTGGA GATCAAA SEQ ID NO: 214 |

FIG. 10

EBOLA VIRUS ANTIBODIES AND BINDING AGENTS DERIVED THEREFROM

CROSS-REFERENCE TO RELATED APPLICATIONS

This application is a continuation of U.S. application Ser. No. 17/196,418 filed Mar. 9, 2021, which is a continuation of U.S. application Ser. No. 16/319,775 filed Jan. 22, 2019, which is the National Stage of International Application No. PCT/US2017/043305 filed Jul. 21, 2017, which claims the benefit of U.S. Provisional Application No. 62/364,986 filed Jul. 21, 2016. The entirety of each of these applications is hereby incorporated by reference for all purposes.

STATEMENT REGARDING FEDERALLY SPONSORED RESEARCH OR DEVELOPMENT

This invention was made with government support under W3194Q-14-1-0010 awarded by DARPA and A1109762 awarded by the National Institutes of Health. The government has certain rights in the invention.

INCORPORATION-BY-REFERENCE OF MATERIAL SUBMITTED AS AN XML FILE VIA THE OFFICE ELECTRONIC FILING SYSTEM

The Sequence Listing associated with this application is provided in XML format and is hereby incorporated by reference into the specification. The name of the XML file containing the Sequence Listing is 16008USCON2.xml. The XML file is 281 KB, was created on Jun. 7, 2023, and is being submitted electronically via the USPTO patent electronic filing system.

BACKGROUND

Ebolaviruses are in the family Filoviridae that cause severe fevers that typically leads to fatalities in humans. Thus, there is a need to identify improved therapeutic methods for treating or preventing Ebola virus infections.

ZMapp is a combination of monoclonal antibodies in testing for the treatment for Ebola virus disease. Qiu et al., Nature, 2014, 514 (7520): 47-53. See also WO2001/016183.

Martinez et al. report an Ebola mucin-like domain effect antiglycoprotein antibody responses induced by Ebola virus-like particles. J Infect Dis. 2011, 204 Suppl 3:S825-32.

Murin et al. report structures of protective antibodies reveal sites of vulnerability on Ebola virus. Proc Natl Acad Sci USA. 2014, 111(48):17182-7.

Flyak et al. report cross-reactive and potent neutralizing antibody responses in human survivors of natural ebolavirus infection. Cell. 2016, 164(3):392-405

Furuyama et al. report an antibody for pan-Ebolavirus therapy. Sci Rep. 2016, 6:20514.

References cited herein are not an admission of prior art.

SUMMARY

This disclosure relates to antibodies and antigen binding fragments that specifically bind Ebola virus particles. In certain embodiments, the antibodies and fragments are capable of treating or preventing an Ebola viral infection. In certain embodiments, the antibodies and antigen binding fragments are also contemplated for diagnostic methods and compositions related thereto. In certain embodiments, the antibodies are non-naturally occurring chimeric antibodies.

In certain embodiments, this disclosure relates to antibodies or antigen binding fragments comprising six complementarity determining regions (CDRs) or consensus sequences thereof, wherein the CDRs comprise the three light chain CDRs derived from an antibody selected from 5.1.10B3, 5.6.1A02, 2.1.1D05, 2.1.1D07, 9.6.3D06, 2.1.7G07, 9.6.3A06, 5.1.13G03, 5.6.c2618, 2.10.1E06, 9.6.1A09, 5.1.7D03 and wherein the CDRs comprise the three heavy chain CDRs derived from an antibody selected from 5.1.10B3, 5.6.1A02, 2.1.1D05, 2.1.1D07, 9.6.3D06, 2.1.7G07, 9.6.3A06, 5.1.13G03, 5.6.c2618, 2.10.1E06, 9.6.1A09, 5.1.7D03, and wherein the antibody or antigen binding fragment thereof specifically or immunospecifically binds to an epitope expressed in an Ebola virus particle.

In certain embodiments, the CDRs comprise the three light chain CDRs of antibody 5.1.10B3 within SEQ ID NO: 1 DIQMTQSPSSLSASVGDRVTIT-CRASQSISSFLNWHQQKPGKAPKLLI-YAASSLQSGVPSR FSGSGSGTDFTLTISSLQPED-FAIYYCQQSYISPFTFGPGTKVDIK; CDR 1 (SEQ ID NO: 11) RASQSISSFLN; CDR2 (SEQ ID NO: 12) AASSLQS; and CDR3 (SEQ ID NO: 13) QQSYIS-PFT; and the three heavy chain CDRs of antibody 5.1.10B3 within SEQ ID NO: 2 EVQLVESGGGLVQPGGSLRLS-CAASGFTFRSYDMHWVRQATGKGLEWV-SAIGTAGDT YYPGSVKGRFTISRENAKNS-LYLQMNSLRAEDTAVYYCARVRFGDTAVDY-WGQGTLV TVSS; CDR 1 (SEQ ID NO: 14) FTFRSYDMH; CDR 2 (SEQ ID NO: 15) IGTAGDTYYP; and CDR 3 (SEQ ID NO: 16) VRFGDTAVDY.

In certain embodiments, the CDRs comprise the three light chain CDRs of antibody 5.6.1A02 within SEQ ID NO: 3 DIVMTQSPRSLSVTPGEPASIS-CRSSQSLLHRNGY-NYLDWYLQKPGQSPQLLIYLGSNRA SGVPDRF SGSGSGTDFTLKISRVEAE-DVGVYYCMQALQTPSWTFGQGTKVEIK; CDR 1 (SEQ ID NO: 17) RSSQSLLHRNGYNYLD; CDR 2 (SEQ ID NO: 18) LGSNRAS; and CDR 3 (SEQ ID NO: 19) MQALQTPSWT; and the three heavy chain CDRs of antibody 5.6.1A02 within SEQ ID NO: 4 EVQLVESGGGLIQPGGSLRLS-CAASGFAVRSNYLSWVRQAPGK-GLEWVSLIYSGGLTAY ADSVEGRFTIS-RDNSKNTLYLQMNSLRVEDTALYYCARVASS-AGTFYYGMDVWGQGT TVTVSS; CDR 1 (SEQ ID NO: 20) FAVRSNYLS; CDR 2 (SEQ ID NO: 21) LIYSGGLTAYADSVEG; and CDR 3 (SEQ ID NO: 22) VASSAGTFYYGMDV.

In certain embodiments, the CDRs comprise the three light chain CDRs of antibody 2.1.1D05 within SEQ ID NO: 5 QSVLTQPPSVSGAPGQRVTISCTGSSSNI-GAGYDVYWYQQLPGTAPKLLIYGNSNRPSGV PDRFSGSKSGTSASLAITGLQAEDEAD-YYCQSFDSSLRDSWVFGGGTKLTVL; CDR 1 (SEQ ID NO: 23) TGSSSNIGAGYDVY; CDR 2 (SEQ ID NO: 24) GNSNRPS; and CDR 3 (SEQ ID NO: 25) QSFDSSLRDSWV, and the three heavy chain CDRs of antibody 2.1.1D05 within SEQ ID NO: 6 EVQLVESGGGLVKPGGSLRLS-CAASGFTFSNAWMNWVRQAPGKGLEWVGRIK- SKTDG GAADYAAPVKGRFTISRDDSKNT-LYLQMNSLKTEDTAVYFCTTVYRYNYDSVWG-QGT LVTVSS; CDR 1 (SEQ ID NO: 26) FTFSNAWMN; CDR 2 (SEQ ID NO: 27) RIK-SKTDGGAADYAAPVKG; and CDR 3 (SEQ ID NO: 28) VYRYNYDSV.

In certain embodiments, the CDRs comprise the three light chain CDRs of antibody 2.1.1D07 within SEQ ID NO: 7 EIVLTQSPGTLSLSPGER-ATLSCRASQSVSSSY-LAWYQQKPGQAPRLLIYGAFNRATGIPD RFSGSGSGTDFTLTISRLEPED-FAVYYCQLYGSSPWTFGQGTKVEIK; CDR 1 (SEQ ID NO: 29) RASQSVSSSYLA; CDR 2 (SEQ ID NO: 30) GAFNRAT; and CDR 3 (SEQ ID NO: 31) QLYGSSPWT, and the three heavy chain CDRs of antibody 2.1.1D07 within SEQ ID NO: 8 EVQLLESGGGLVQPGGSLRLS-CAASGFTFSTYGMSWVRQAPGKGLEWVSGIS-GSGGITY YADSVRGRFTISRDNSKNT-LYLRMNSLRAEDTAVYYCAKVGEYYDFWSG-YSPFEYWG QGTL; CDR 1 (SEQ ID NO: 32) FTF-STYGMS; CDR 2 (SEQ ID NO: 33) GISGSGGITYY-ADSVRG; and CDR 3 (SEQ ID NO: 34) VGEYYDFWSGYSPFEY.

In certain embodiments, the CDRs comprise the three light chain CDRs of antibody 9.6.3D06 within SEQ ID NO: 9 DIQMTQSPSTLSASVGDRVTIT-CRASQRINNLVAWYQQKPGKAPKVMIYDAS-SLKSGVP SRFSGSGSGTEFTLTISSLQPDDFA-TYFCQQYDTDSGWTFGQGTKVEIK; CDR 1 (SEQ ID NO: 35) RASQRINNLVA; CDR 2 (SEQ ID NO: 36) DASSLKS; CDR 3 (SEQ ID NO: 37) QQYDTDSGWT, and the three heavy chain CDRs of antibody 9.6.3D06 within SEQ ID NO: 10 EVQLLESGGGLVQPGGSLRLS-CAASGFTFSKY-AMIWVRQAPGKGLQWVAGINKSGGRT YYADSVRGRFTISRDNSKNTLYLQMKSLRADD-TAMYYCAKEGSPLSDVLLVAAPFGWF DPWGQGTLVTVSS; CDR 1 (SEQ ID NO: 38) FTFSKYAMI; CDR 2 (SEQ ID NO: 39) GINKSG-GRTYYADSVRG; and CDR 3 (SEQ ID NO: 40) EGSPLSDVLLVAAPFGWFDP.

In certain embodiments, the CDRs comprise the three light chain CDRs of antibody 2.1.7G07 within SEQ ID NO: 69 EIVLTQSPGTLSLSPGER-ATLSCRASQSVSSSY-LAWYQQKPGQAPRLLIYGAFNRATGIPD RFSGSGSGTDFTLTISRLEPEDFAVYYCQQYGR-SPFTFGPGTKVDIK; CDR 1 (SEQ ID NO: 70) QSVSSSY; CDR2 (SEQ ID NO: 71) GAFNRAT; and CDR3 (SEQ ID NO: 72) QQYGRSPFT; and the three heavy chain CDRs of antibody 2.1.7G07 within SEQ ID NO: 73 EVQLVESGGGLVQPGGSLRLS-CAASGFAFSTYAMSWVRQAPGKGLEWV-SAITGSGYST YYADSVKGRFTISGDNSKNT-LYLQMNSLRAEDTALYYCAKVGEYYDFWSGYS-PFDSW GQGTLVTVSS; CDR 1 (SEQ ID NO: 74) GFAFSTYA; CDR 2 (SEQ ID NO: 75) ITGSGYST; and CDR 3 (SEQ ID NO: 76) AKVGEYYDFWSGYSPFDS.

In certain embodiments, the CDRs comprise the three light chain CDRs of antibody 9.6.3A06 within SEQ ID NO: 77 DIVMTQTPLSSAVTLGQPASIS-CRSSQRLVHSDGNTYLSWLHQRPGQP-PRLLIYKVSLRFS GVPDRFSGSGAGTDFTLKIS-RVEAEDVGIYYCMQATQFPLTFGGGTKVEIK; CDR 1 (SEQ ID NO: 78) QRLVHSDGNTY; CDR 2 (SEQ ID NO: 79) KVSLRFS; and CDR 3 (SEQ ID NO: 80) MQATQFPLT; and the three heavy chain CDRs of antibody 9.6.3A06 within SEQ ID NO: 81 EVQLLESGGGLVKPGGSLRLS-CAASGFTFNEYMMNWVRQPPGKGLEWVSSIS-GTSTYIN YADSVKGRFTISRDNAKNS-LYLQMNSLRSDDTAMYYCARGSTGGYWGQG-TLITVSS; CDR 1 (SEQ ID NO: 82) GFTFNEYM; CDR 2 (SEQ ID NO: 83) ISGTSTYI; and CDR 3 (SEQ ID NO: 84) GSTGGY.

In certain embodiments, the CDRs comprise the three light chain CDRs of antibody 5.1.13G03 within SEQ ID NO: 85 DIQMTQSPSSLSASVGDRVTIT-CRASQSIS-SYLNWYQQKPGKAPKVLIYSAFSLQNGVPS RFSGSGSGTDFTLTISSLQPEDFATYYCQQSYST-PRTFGQGTKVEIK; CDR 1 (SEQ ID NO: 86) QSIS-SYLN; CDR 2 (SEQ ID NO: 87) SAFSLQN; and CDR 3 (SEQ ID NO: 88) QQSYSTPRT; and the three heavy chain CDRs of antibody 5.1.13G03 within SEQ ID NO: 89 QVQLQESGPGLVKPSGTLSLT-CAVSGGSISSTNWWSWVRQPPGK-GLEWIGEIYHSGSTN YNPSLKSRVTISLDK-SKDQFSLKLSSVTAADTAVYYCAYSNTWTG--GWGQGTLVTVSS; CDR 1 (SEQ ID NO: 90) GSIS-STNWWS; CDR 2 (SEQ ID NO: 91) HSGSTN; and CDR 3 (SEQ ID NO: 92) SNTWTGG.

In certain embodiments, the CDRs comprise the three light chain CDRs of antibody 5.6.c2618 within SEQ ID NO: 93 EVVLTQSPVTLSLSPGER-ATLSCRASQSVSGY-LAWYQQKPGQVPRLLIYDTSNRATGIPA RFSGSGSGTDFTLTISTIEPEDFAVYYCQQR-SKWGVTFGGGTKVDIK; CDR 1 (SEQ ID NO: 94) QSVSGYLA; CDR 2 (SEQ ID NO: 95) DTSNRAT; and CDR 3 (SEQ ID NO: 96) QQRSKWGVT; and the three heavy chain CDRs of antibody 5.6.c2618 within SEQ ID NO: 97 QVQLVQSGAEVKKP-GASVNLSCKGSGYSFRTYYIHWVRQAPGQ-GLEWMGIINSSGGGT TYAQKFQGRVTMTRDTSTSTVYMELRSLKYED-TAMYYCARDRFPTVSGEPFAMDVWG QGTTVTVSS; CDR 1 (SEQ ID NO: 98) GYSFRTYYIH; CDR 2 (SEQ ID NO: 99) INSSGGGTTY; and CDR 3 (SEQ ID NO: 100) DRFPTVSGEPFAMDV.

In certain embodiments, the CDRs comprise the three light chain CDRs of antibody 2.10.1E06 within SEQ ID NO: 101 EIVLTQSPGTLSLSPGER-ATLSCRASQSVTSNYLAWYQQKPGQAPRVLIY-GASSRATGIP DRFSGSGSGTDFTLTISRLEPED-FAVYYCQQFGASPPYSFGQGTKVEIK; CDR 1 (SEQ ID NO: 102) QSVTSNYLA; CDR 2 (SEQ ID NO: 103) GASSRAT; and CDR 3 (SEQ ID NO: 104) QQFGASPPYS; and the three heavy chain CDRs of antibody 2.10.1E06 within SEQ ID NO: 105 EVQLVESGGGLIQPGGSLRLSC-TASGFTFSKFAMSWVRQAPGRGLEWISYISGG-SKTKY YADSVRGRFTISRDNAKGSLFLQMNSL-RAEDTAIYFCAKKGWQSTFLGMDYFYGMDV WGKGTTVTVSS; CDR 1 (SEQ ID NO: 106) GFTFSKFAMS; CDR 2 (SEQ ID NO: 107) ISGG-SKTKY; and CDR 3 (SEQ ID NO: 108) AKKGWQST-FLGMDYFYGMDV.

In certain embodiments, the CDRs comprise
the three light chain CDRs of antibody 9.6.1A09 within SEQ ID NO: 109 DIVMTQSPDSLAVSLGERASIN-CKSSQSVLSSSNTKNYLAWYQHKPGQPPKWY-WAST RESGVPDRFSGSGSGTDFTLTISSLQPEDVA-VYYCQQYYGAPYTFGQGTKVEIK; CDR 1 (SEQ ID NO: 110) QSVLSSSNTKNY; CDR 2 (SEQ ID NO: 111) WASTRES; and CDR 3 (SEQ ID NO: 112) QQYYGAPYT; and
the three heavy chain CDRs of antibody 9.6.1A09 within SEQ ID NO: 113 EVQLVESGGGLVQPGGSLRLS-CAASGFTFRSYDMDWFRQSTGKGLEWV-SAIGSAGDTY YTDSVKGRFTISRENGKNS-LYLQMNSLRAGDTAVYYCARARFGDNVFDLW-GRGTLVT VSS; CDR 1 (SEQ ID NO: 114) FTFRSYDMD; CDR 2 (SEQ ID NO: 115) IGSAGDT; and CDR 3 (SEQ ID NO: 116) ARFGDNVFDL.

In certain embodiments, the CDRs comprise
the three light chain CDRs of antibody 5.1.7D03 within SEQ ID NO: 117 EIVLTQSPGTLSLSPGER-AALSCRASQSVSGNYFAWYQQKSGQAPRL-LISAASSRATGVP DRFSASGSGTDFTLTISRLE-PEDSAVYYCQQYGSSPLTFGQGTKVEIK; CDR 1 (SEQ ID NO: 118) SVSGNYFA; CDR 2 (SEQ ID NO: 119) AASSRAT; and CDR 3 (SEQ ID NO: 120) QQYGSSPLT; and
the three heavy chain CDRs of antibody 5.1.7D03 within SEQ ID NO: 121 EVQLVQSGGGLAQPGGSLRLS-CAASGFTFRSYDIVIHWVRQVTGKGLEWV-SAIGTAGDT YYTGSVKGRFTISRENDKSS-LYLQMSSLRGEDTAVYYCARAAFGSHYFDY-WGQGTLVT VSS; CDR 1 (SEQ ID NO: 122) FTFRSYDMH; CDR 2 (SEQ ID NO: 123) IGTAGDTYYT; and CDR 3 (SEQ ID NO: 124) AAF-GSHYFDY.

In certain embodiments, an antibody or antigen binding fragment thereof comprises a light chain variable region comprising the amino acid sequence of SEQ ID NO: 1, 3, 5, 7, 9, 69, 77, 85, 93, 101, 109, or 117 having at least 80, 85, 90, 95, 98, 99%, or more sequence identity or similarity thereto.

In certain embodiments, an antibody or antigen binding fragment thereof comprises a heavy chain variable region comprising the amino acid sequence of SEQ ID NO: 2, 4, 6, 8, 10, 73, 81, 89, 97, 105, 113, or 121 having at least 80, 85, 90, 95, 98, 99%, or more sequence identity or similarity thereto.

In certain embodiments, the antibody or antigen binding fragment has CDRs of SEQ ID NO: 11, 12, 13, 14, 15, and 16, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 17, 18, 19, 20, 21, and 22, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 23, 24, 25, 26, 27, and 28, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 29, 30, 31, 32, 33, and 34, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 35, 36, 37, 38, 39, and 40, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 70, 71, 72, 74, 75, and 76, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 78, 79, 80, 82, 83, and 84, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 86, 87, 88, 90, 91 and 92, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 94, 95, 96, 98, 99, and 100, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 102, 103, 104, 106, 107, and 108, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 110, 111, 112, 114, 115, and 116, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 118, 119, 120, 122, 123, and 124, wherein one, two, three, four, five, or all of the CDRs contain one, two, three, or four amino acid substitutions. In certain embodiments, the substitutions are conservative substitutions.

In certain embodiments, this disclosure relates to antibodies or antigen binding fragments comprising six complementarity determining regions (CDRs) or consensus sequences thereof, wherein the CDRs comprise the three light chain CDRs derived from an antibody selected from 2.1.1B02, 5.24.1C11, 9.20.1C03, 5.24.1B03, 9.20.1D09, 5.24.2A03, 9.20.1A02, 5.24.2C05, 5.24.2B07 and wherein the CDRs comprise the three heavy chain CDRs derived from an antibody selected from 2.1.1B02, 5.24.1C11, 9.20.1C03, 5.24.1B03, 9.20.1D09, 5.24.2A03, 9.20.1A02, 5.24.2C05, 5.24.2B07, and wherein the antibody or antigen binding fragment thereof specifically or immunospecifically binds to an epitope expressed in an Ebola virus particle.

In certain embodiments, the CDRs comprise
the three light chain CDRs of antibody 2.1.1B02 within SEQ ID NO: 125 SYELTQPPSVSVSPGQ-TARITCSGDALPKQYAYWYQQKPGQAPVPVIYKD-SERPSGIPER FSGSSSGTTVTLTISGVQAEDEAD-YYCQSSDSSGTYVVFGGGTKLTVL; CDR 1 (SEQ ID NO: 126) ALPKQY; CDR2 (SEQ ID NO: 127) KDSE; and CDR3 (SEQ ID NO: 128) QSSDSSGTYVV; and the three heavy chain CDRs of antibody 2.1.1B02 within SEQ ID NO: 129 EVQLVQSGAEVKKP-GASVKVSCKASGYTFTSYYMHWVRQAPGQ-GLEWMGIINPSGGS TSYAQKFQGRVTMTRDTST-STVYMELSSLRSEDTAVYYCARHDSSGYDAF-DIWGQGTM VTVSS; CDR 1 (SEQ ID NO: 130) GYTFTSYY; CDR 2 (SEQ ID NO: 131) INPSGGST; and CDR 3 (SEQ ID NO: 132) ARHDSSGYDAFDI.

In certain embodiments, the CDRs comprise
the three light chain CDRs of antibody 5.24.1C11 within SEQ ID NO: 133 DIVMTQSPLSLPVTPGEPASIS-CRSSQSLLHSNG-YNYVDWYLQKPGQSPQLLIYLGSSRAS GVPDRFSGSGSGTDFTLKISRVET-EDVGIYYCMQGLQTPLTFGGGTKVEIK; CDR 1 (SEQ ID NO: 134) QSLLHSNGYNY; CDR2 (SEQ ID NO: 135) LGSS; and CDR 3 (SEQ ID NO: 136) MQGLQTPLT; and the three heavy chain CDRs of antibody 5.24.1C11 within SEQ ID NO: 137 QVQLVQSGAEVKKP-GASVKVSCRTSGYTFSSYNIHWVRQAPGQ-GLEWMGVINPYGRST TLYARR-FRDRVTMTRDTSTSTVYMELSSLRSEDTAVYFCGR-LYSGAPYGLDVWGQGST VTVSS; CDR 1 (SEQ ID NO: 138) GYTFSSYNIH; CDR 2 (SEQ ID NO: 139) PYGRSTT, and CDR 3 (SEQ ID NO: 140) GRLYSGAPYGLDV.

In certain embodiments, the CDRs comprise
the three light chain CDRs of antibody 9.20.1C03 within SEQ ID NO: 141 DIVLTQSPDSLAASLGER-ATISCKSSHSVLYSSNNKDF-FAWYQQKPGQPPKLLISWASTR ESGVPVRFNGGGSGTHFTLTISSLQAEDVA-VYYCQQYFSSPITFGQGTRLEIK; CDR 1 (SEQ ID NO: 142) HSVLYSSNNKDF; CDR2 (SEQ ID NO: 143) WAST; and CDR3 (SEQ ID NO: 144) QQYFSSPIT; and the three heavy chain CDRs of antibody 9.20.1C03 within SEQ ID NO: 145 QVQLVQSGAEVKKPGSSVK-VACKVSGGTFSSYTISWVRQAPGQGLEWMG-GIIPSFGVG HYSQKFRDRVTLTADKSTT-TAFLELSSVRSEDTALYYCAILGTFNWKSGGN-YFGPWGQ GTLVTVSS; CDR1 (SEQ ID NO: 146) GGTFSSYT; CDR 2 (SEQ ID NO: 147) IIPSFGVG; and CDR 3 (SEQ ID NO: 148) AILGTFNWKSGG-NYFGP.

In certain embodiments, the CDRs comprise
the three light chain CDRs of antibody 5.24.1B03 within SEQ ID NO: 149 EIVLTQSPNTLSLSPGER-ATLSCRASQSLRTNQLAWYQQKPGQAPRLLIHT-STRATGIPDR FSGSGSGTDFTLTISGLEAED-FAVYYCQASDTSSLTFGGGTKLEIR; CDR 1 (SEQ ID NO: 150) QSLRTN; CDR2 (SEQ ID NO: 151) HTST; and CDR3 (SEQ ID NO: 152) QASDTSSLT; and the three heavy chain CDRs of antibody 5.24.1B03 within SEQ ID NO: 153 QVQLQESGPGLVKPSESLSLTC-TISGGSIRDYYWSWIRQAPGKGLEWIGYKY-HAARGNS NPSLESRVTMSIDTSRSEFSLRLT-SVTAADTAVYYCARVQYGPGGGYYSGNW-LDLWGQ GTLVTVSS; CDR 1 (SEQ ID NO: 154) GGSIRDYY; CDR 2 (SEQ ID NO: 155) KYHAARG; and CDR 3 (SEQ ID NO: 156) ARVQYGPGG-GYYSGNWLDL.

In certain embodiments, the CDRs comprise
the three light chain CDRs of antibody 9.20.1D09 within SEQ ID NO: 157 EIVMTQSPATLSL-SPGERASLSCRASQSIATNLAWYQQKPGQP-PRVLIYGASTRATGIPTR FSGSGSGTEFTLTISSLQSEDFAIYY-CHQYHSWRTFGQGTKVEMK; CDR 1 (SEQ ID NO: 158) QSIATN; CDR2 (SEQ ID NO: 159) GAST; and CDR3 (SEQ ID NO: 160) HQYHSWRT; and the three heavy chain CDRs of antibody 9.20.1D09 within SEQ ID NO: 161 QLQLQESGPGLVKP-SETLSLTCTVSGGSVASSNDYWGWIRQPPGKG-PEWIGTIFYRGTTD YNPSLKSRLTMSVDTSRNQFSLKLSSVTAAD-TAVYYCARLPLWFSELGHDYWGQGTLV TVSS; CDR 1 (SEQ ID NO: 162) GGSVASSNDY; CDR 2 (SEQ ID NO: 163) IFYRGTT; and CDR 3 (SEQ ID NO: 164) ARLPLWFSELGHDY.

In certain embodiments, the CDRs comprise
the three light chain CDRs of antibody 5.24.2A03 within SEQ ID NO: 165 QSALTQPP-SASGSPGQSVTISCTGTSSDVGVYNS-VSWYRQHPGKVPKLMIYEVSKRPSG VPDRFSG-SKSGNTASLTVSGLQADDEGDYYCCSCSGTN-SLCVFGTGTKVTVL; CDR 1 (SEQ ID NO: 166) SSDVGVYNS; CDR2 (SEQ ID NO: 167) EVSK; and CDR3 (SEQ ID NO: 168) CSCSGTNSLCV; and the three heavy chain CDRs of antibody 5.24.2A03 within SEQ ID NO:169 QVQLHESGPGLVQP-SETLSLTCTVSGDSITNYYWSWIRQPPGK-GLEWIGYMYYSASAHY NPSLQSRVTISVDTSKNQFSLKLSSVTAAD-TAVYFCARVDYSSSSYYSGNWFDPWGQGT LVTVSS; CDR 1 (SEQ ID NO: 170) GDSITNYY; CDR 2 (SEQ ID NO: 171) MYYSASA; and CDR 3 (SEQ ID NO: 172) ARVDYSSSSYYSGNWFDP.

In certain embodiments, the CDRs comprise
the three light chain CDRs of antibody 9.20.1A02 within SEQ ID NO: 173 QSVLTQPPSVSGAPGQTVTISCTGSYSNI-GAGYDVQWYQHLPGTAPKLLIYDNVHRPSG VPDRFSGSKSGTSASLAITGLQTEDEAD-YYCQSYDSRLRDQWVFGGGTKLTVL; CDR 1 (SEQ ID NO: 174) YSNIGAGYD; CDR2 (SEQ ID NO: 175) DNVH; and CDR3 (SEQ ID NO: 176) QSYDSRLRDQWV; and the three heavy chain CDRs of antibody 9.20.1A02 within SEQ ID NO: 177 EVQLVESGGDLVQPGGSLRLS-CAASGITLSGVWMNWVRQAPGKGLEWI-GRIKSTSDGG RADFAAPAR-GRFTMSRDESKNKLFLQMNNLGIEDTGMYY-CFTRVQRDGTKDDFWGRG TLVTVSS; CDR 1 (SEQ ID NO: 178) GITLSGVW; CDR 2 (SEQ ID NO: 179) IKSTSDGGRA;
and CDR 3 (SEQ ID NO: 180) FTRVQRDGTKDDF.

In certain embodiments, the CDRs comprise
the three light chain CDRs of antibody 5.24.2C05 within SEQ ID NO: 181 QSALTQPASVSGSPGQSITLSCTVGG-NKFVSWYQQHPGKAPKLIISDFT-DRPSGVSSRFSG SKSGNTASLTISGLQPD- DEATYFCSSYASTSTSLWVFGGGTKLTVL; CDR 1 (SEQ ID NO: 182) CTVGGNKF; CDR2 (SEQ ID NO: 183) DFTD; and CDR3 (SEQ ID NO: 184) SSYASTSTSLWV; and the three heavy chain CDRs of antibody 5.24.2C05 within SEQ ID NO: 185 QEQLQESGPGLVKPSGTLSLTCTVSGVSVSGS-YFWNWVRQPPGKGLEWLGFIHSTGSTN TNPSLKSRVTISVDTSKNQFSLRLTSVSAAD-TAVYYCARAAWLVGGEYYNYGMDLWG QGTTVTVSS; CDR 1 (SEQ ID NO: 186) GVSVSGSYF; CDR 2 (SEQ ID NO: 187) IHSTGST; CDR 3 (SEQ ID NO: 188) ARAAWLVGGEYYNYGMDL.

In certain embodiments, the CDRs comprise the three light chain CDRs of antibody 5.24.2B07 within SEQ ID NO: 189 GIQLTQSPSFLSASVGDRVTIT-CRASQGIYTYLAWYQQKPGKAPKLLVYV-ASTLQSGVPS RFSGSGSGTEFTLTISSLQPEDFA-TYYCQQLNSYPLTFGQGTKLEIK; CDR 1 (SEQ ID NO: 190) QGIYTY; CDR2 (SEQ ID NO: 191) VAST; and CDR3 (SEQ ID NO: 192) QQLNSYPLT; and the three heavy chain CDRs of antibody 5.24.2B07 within SEQ ID NO: 193 QVQLVES-GGGVVQPGRSLRLSCVASGFTFSSYGMHWV-RQAPGKGLEWVAFIWYDGTI QYYGDSVKGRFI-ISRDNSRNTLYLQMNSLRAEDTAVYYCAST-LYRNGDYGSGSRTPDD YWGQGTLVTVSS; CDR 1 (SEQ ID NO: 194) GFTFSSYG; CDR 2 (SEQ ID NO: 195) IWYDGTIQ; and CDR 3 (SEQ ID NO: 196) ASTLYRNGDYGSGSRTPDDY.

In certain embodiments, an antibody or antigen binding fragment thereof comprises a light chain variable region comprising the amino acid sequence of SEQ ID NO: 125, 133, 141, 149, 157, 165, 173, 181 or 189 having at least 80, 85, 90, 95, 98, 99%, or more sequence identity or similarity thereto.

In certain embodiments, an antibody or antigen binding fragment thereof comprises a heavy chain variable region comprising the amino acid sequence of SEQ ID NO: 129, 137, 145, 153, 161, 169, 177, 185, or 193 having at least 80, 85, 90, 95, 98, 99%, or more sequence identity or similarity thereto.

In certain embodiments, the antibody or antigen binding fragment has CDRs of SEQ ID NO: 126, 127, 128, 130, 131, and 132, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 134, 135, 136, 138, 139, and 140, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 142, 143, 144, 146, 147, and 148, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 150, 151, 152, 154, 155, 156, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 158 159 160, 162, 163, 164, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 166, 167, 168, 170, 171, 172, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 174, 175, 176, 178, 179, 180 wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 182, 183, 184, 186, 187, 188, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 190, 191, 192, 194, 195, 196, wherein one, two, three, four, five, or all of the CDRs contain one, two, three, or four amino acid substitutions. In certain embodiments, the substitutions are conservative substitutions.

In certain embodiments, the antibody, antigen binding fragment, the light chain, or the heavy chain comprises a non-naturally occurring chimeric amino acid sequence such that there is at least one mutation that is not present in naturally occurring antibodies comprising the six CDRs.

In certain embodiments, the antibody, antigen binding fragment, or heavy chain, comprises a human constant domain from an immunoglobulin constant region (Fc) having one, two, three, four, five, six, or more of the following mutations G236A, S239D, A330L, I332E, S267E, L328F, P238D, H268F, S324T, S228P, G236R, L328R, L234A, L235A, M252Y, S254T, T256E, M428L, N434S, A330L, N297A, N297Q.

In certain embodiments, this disclosure relates to antibodies comprising the triple mutation M252Y/S254T/T256E or the quadruple mutation of G236A/S239D/A330L/I332E.

In certain embodiments, antigen binding fragments disclosed herein comprises a human constant domain from an immunoglobulin constant region (Fc). In certain embodiments, the antibody or antigen fragment disclosed herein, comprising at least one amino acid substitution in the heavy chain constant region that is not present in naturally occurring antibodies comprising the six CDRs. In certain embodiments, the heavy chain comprises a sequence in a constant region that is different from any sequences present in naturally derived antibodies for which the light chain variable region comprises the three light chain CDRs and the heavy chain variable region comprise the three light chain CDRs or consensus sequences thereof.

In certain embodiments, the epitope expressed on an Ebola virus particle is arrayed on a surface, expressed on the surface of a cell, or expressed at an endogenous or transfected concentration, and the antibody or antigen binding fragment is bound to the epitope.

In certain embodiments, the antibody or antigen binding fragment is capable of inducing an immune response to the Ebola virus or capable of neutralizing an of Ebola virus from replicating.

In certain embodiments, the disclosure relates to nucleic acids encoding an antibody or antigen binding fragment disclosed herein or a vector or expression system comprising such a nucleic acid. In certain embodiments, the disclosure relates to nucleic acids disclosed herein and variants which are synonymous mutations and non-synonymous mutations, e.g., codon optimized mutations.

In certain embodiments, the antibody or antigen binding fragment thereof is detectably labeled or comprises a conjugated toxin, drug, receptor, enzyme, receptor ligand.

In certain embodiments, the disclosure relates to pharmaceutical compositions comprising the antibody or antigen binding fragment thereof disclosed herein, and a physiologically acceptable carrier or excipient.

In certain embodiments, the disclosure relates to methods of detection Ebola virus infection, comprising: (a) assaying the expression of Ebola virus epitope in cells or in a tissue sample of a subject using the antibody or antigen binding fragment thereof disclosed herein and (b) comparing the level of the Ebola virus epitope with a control level, wherein an increase in the assayed level of Ebola virus compared to the control level is indicative of the infection.

In certain embodiments, the expression of Ebola virus epitope is assayed by enzyme linked immunosorbent assay (ELISA), radioimmunoassay (RIA), or fluorescence-activated cell sorting (FACS).

In certain embodiments, the disclosure relates to methods of preventing or treating an Ebola virus infection comprising administering an effective amount of a pharmaceutical composition disclosed herein to a subject in need thereof. In certain embodiments, the subject is at risk of, exhibiting symptoms of, or diagnosed with an Ebola virus infection.

BRIEF DESCRIPTION OF THE DRAWINGS

FIG. 2 illustrates nucleic acid sequences encoding and amino acid sequences for the heavy (right) and light (left) variable regions of antibodies 5.1.10B3 and 5.6.1A02.

FIG. 3 illustrates nucleic acid sequences encoding and amino acid sequences for the heavy (right) and light (left) variable regions of antibodies 2.1.1D05 and 2.1.1D07.

FIG. 4 illustrates nucleic acid sequences encoding and amino acid sequences for the heavy (right) and light (left) variable regions of antibody 9.6.3D06.

FIG. 5 shows data on antibodies against maEVOV in BALB/c mice. Mice were given 100 ug of the indicated mAbs 24 hours prior to challenge with 100 pfu of Ebola Zaire (Mayinga strain). Note: C13C6 is a previously described antibody and component of Zmapp that was included as a control. 42-2D2 is an influenza specific negative control mAb made at Emory.

FIG. 8 illustrates nucleic acid sequences for the heavy (right) and light (left) variable regions of antibodies 2.1.1B02, 5.24.1C11 and 9.20.1CB3.

FIG. 9 illustrates nucleic acid sequences for the heavy (right) and light (left) variable regions of antibodies 5.24.1B3, 9.20.1D09 and 5.24.2A03. FIG. 10 illustrates nucleic acid sequences for the heavy (right) and light (left) variable regions of antibodies 9.20.1A02, 5.24.2C05 and 5.24.2B07.

DETAILED DESCRIPTION

Figure 1:
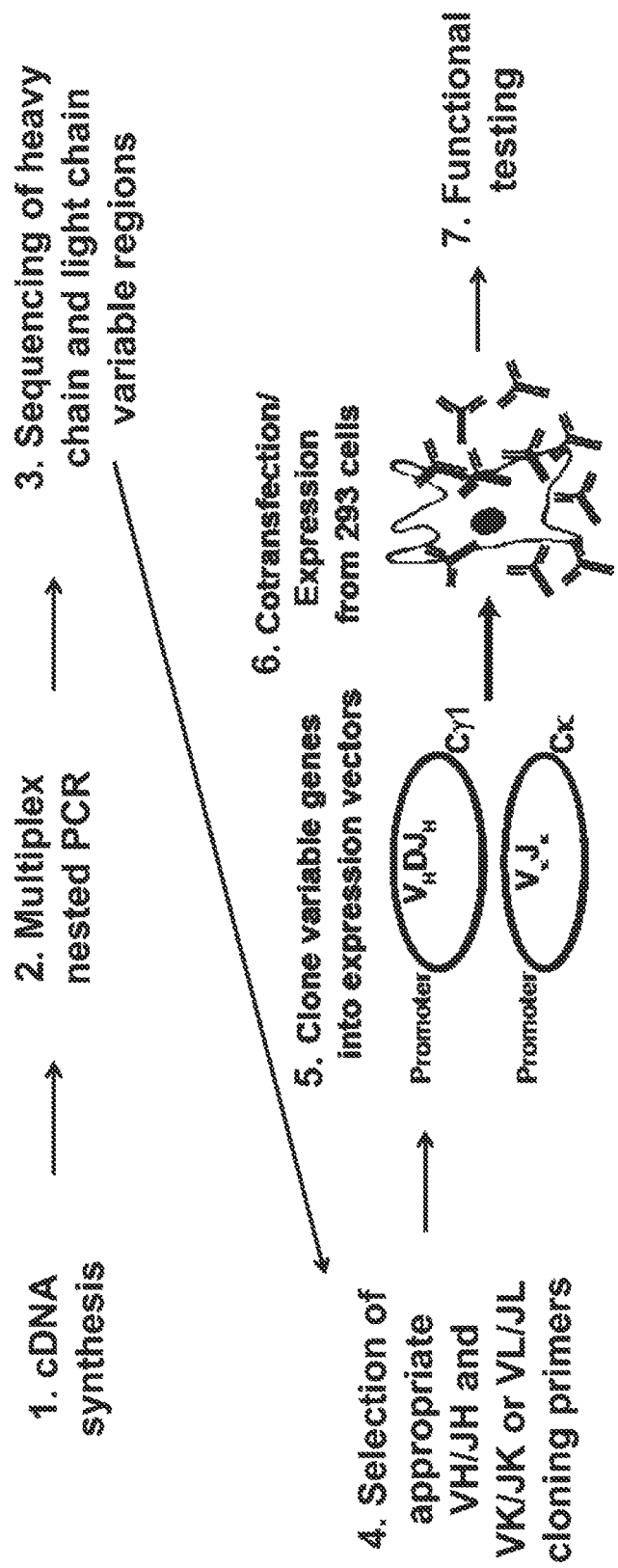
FIG. 1 illustrates a method of isolating variable antibody sequences from cells and grafting them to human constant regions.
Figure 6:
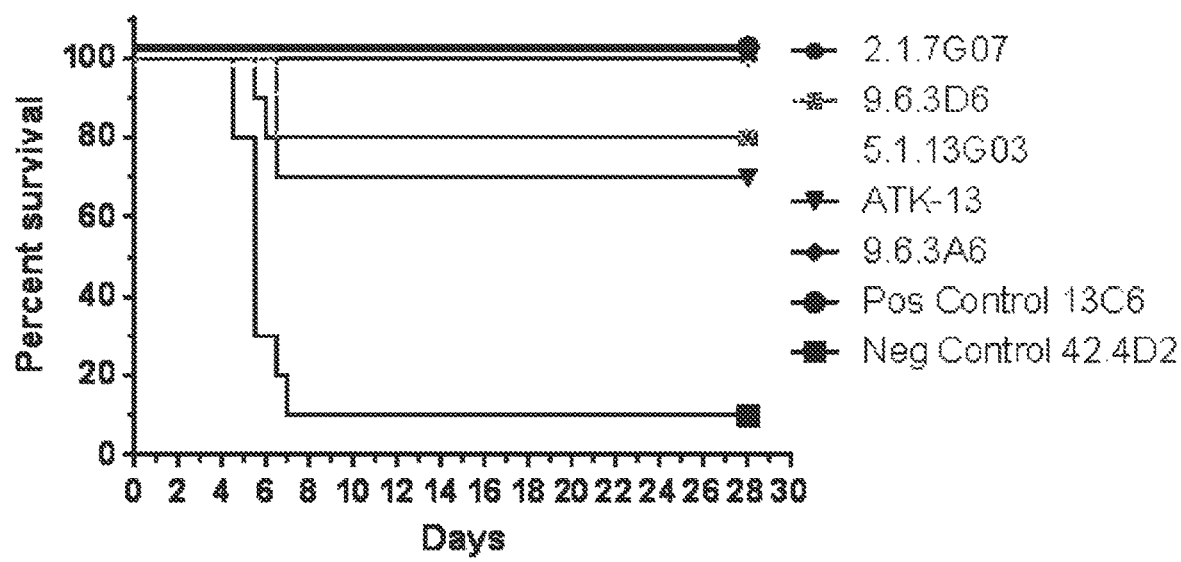
FIG. 6 shows data on antibodies. Mice were given 100 ug of the indicated mAbs 24 hours prior to challenge with 100 pfu of Ebola Zaire (Mayinga strain). Note: ATK-13 is the same as 5.6.c2618.
Figure 7:
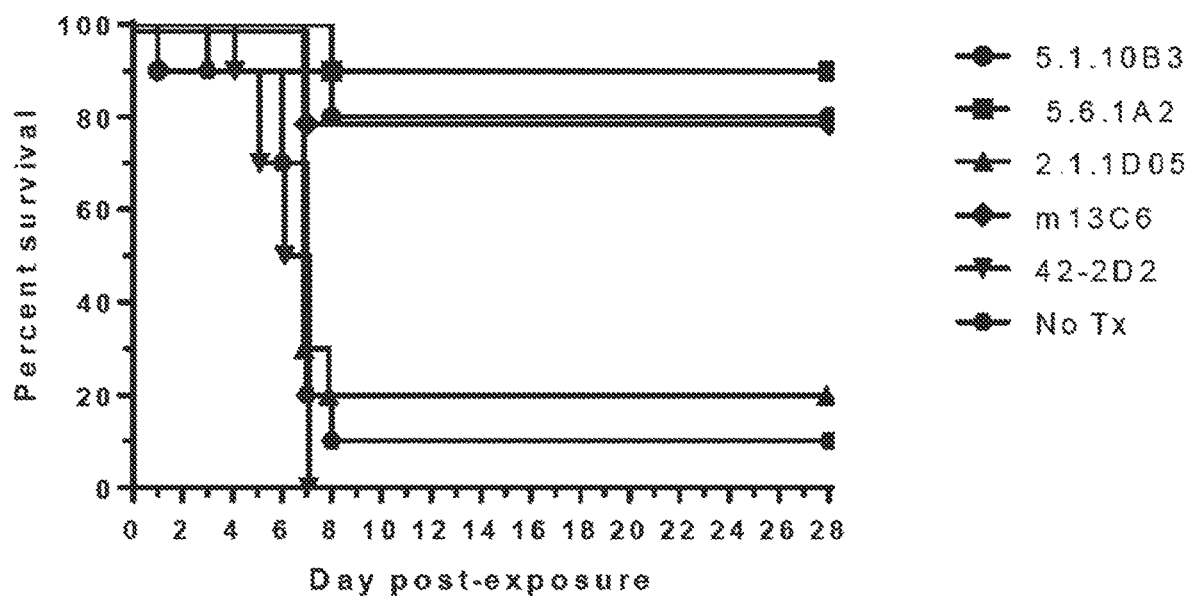
FIG. 7 shows data on antibodies against maEBOV in BALB/c Mice. Mice were given 100 ug of the indicated mAbs 24 hours prior to challenge with 100 pfu of Ebola Zaire (Mayinga strain). Note: C13C6 is a previously described antibody and component of Zmapp that was included as a control. 42-2D2 is an influenza specific negative control mAb made at Emory.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In the claims appended hereto, the term "a" or "an" is intended to mean "one or more," and the term "comprise" and variations thereof such as "comprises" and "comprising," when preceding the recitation of a step or an element, are intended to mean that the addition of further steps or elements is optional and not excluded.

As used herein, the terms "treat," "treating," "treatment" and "therapeutic use" refer to the elimination, reduction, or amelioration of one or more symptoms of a disease or disorder that would benefit from an increased or decreased immune response. As used herein, a "therapeutically effective amount" refers to that amount of a therapeutic agent sufficient to mediate an altered immune response, and more preferably, a clinically relevant altered immune response, sufficient to mediate a reduction or amelioration of a symptom. An effect is clinically relevant if its magnitude is sufficient to impact the health or prognosis of a recipient subject. A therapeutically effective amount refers to the amount of the therapeutic agent that provides a therapeutic benefit in the treatment.

The term "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human patient.

The term "sample" refers to any mixture of biological materials derived from a subject, e.g., bodily fluids, whole blood, serum, plasma, tissue, skin, saliva, urine, stool, tears, amniotic fluid, breast milk etc. Biological samples may be obtained from animals (including humans) and encompass fluids, solids, tissues, and gases.

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

The term "substantially," as used in the context of binding or exhibited effect, is intended to denote that the observed effect is physiologically or therapeutically relevant. Thus, for example, a molecule is able to substantially block an activity of an Ebola virus if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation, and optionally post-translational modifications such as RNA polymerase, regulatory protein factors, transcription factors, ribosomes, tRNA cofactors, amino acids, and nucleotides. In the presence of an expression vector, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (at1D), UDP-glucose:galactose-1-phosphate uridyltransferaseI (galT), feedback-insensitive α subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to antibodies and antigen binding fragments comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to vectors comprising a nucleic acid encoding an antibody or antigen binding fragment disclosed herein or chimeric protein thereof.

In certain embodiments, the vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 215) and GGGGT (SEQ ID NO: 216) have a sequence identity of 4 out of 5 or 80%. For example, the polypeptides GGGPPP (SEQ ID NO: 217) and GGGAPPP (SEQ ID NO: 218) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

As used herein, the term "combination with" when used to describe administration with an additional treatment means that the agent may be administered prior to, together with, or after the additional treatment, or a combination thereof.

Ebola Virus

Ebola is a deadly disease caused by infection with one of the Ebola virus species. The disease is spread through direct contact with bodily fluids, contaminated objects, infected fruit bats or primates, or from sexual contact. In a period from 3-21 days, Ebola virus causes symptoms such as fever, muscle pain, and vomiting, and can also lead to unexplained hemorrhage and, if left untreated, eventually death. Although it is considered a rare disease, in 2014, the largest Ebola outbreak in history nucleated in West Africa (Guinea) and was thought to be caused by a new Ebola virus strain.

Ebola viruses are categorized in the family Filoviridae and typically cause severe hemorrhagic fevers and fatalities in humans. Ebola viruses include Zaire Ebola virus (EBOV), Sudan virus (SUDV), Tai forest virus (TAFV), Bundibugyo virus (BDBV), and Reston virus (RESTV). The Ebolavirus virion core consists of the negative-sense RNA genome. The core is surrounded by a lipid envelope with surface projections that are comprised of a glycoprotein (GP).

Ebola viruses are RNA viruses that are thread-like in appearance and consist of seven structural proteins including glycoprotein, matrix proteins, and nucleocapsid proteins. Virus particles are surrounded by a host cell-derived membrane in which the surface glycoprotein GP is embedded.

Typically, survival from an Ebola viral infection depends on access to adequate healthcare early in disease progression. Treatment consists of providing fluids, maintaining oxygen and blood pressure, and treating other infections. Survivors do develop antibodies against Ebola virus that may persist for up to 10 years.

Ebola virus infections typically result in the onset of fever and chills, but low-grade fever and malaise may also precede the development of more severe symptoms. Watery diarrhea nausea, vomiting, and abdominal pain are common. Gastrointestinal bleeding, blood in the stool, and mucosal bleeding may occur. Blurred vision, photophobia, blindness may occur during the acute phase of illness. A diffuse erythematous, nonpruritic maculopapular rash may develop. The rash usually involves the face, neck, trunk, and arms, and can desquamate. Multi-organ failure with death typically occurring in the second week.

The presence of the Ebola virus can be done by the detection of viral RNA, e.g. by RT-PCR, and/or by detection of Ebola antigen by a specific Antigen detection test, and/or by detection of immunoglobulin M (IgM) antibodies directed against Ebola.

Antibody and Antigen Binding Fragments

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to the disclosed B7-H5 antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site and exhibit an ability to immunospecifically bind an antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, non-naturally occurring chimeric or humanized derivatives of anti-Ebola virus antibodies are particularly preferred for in vivo use in humans, however, murine antibodies or antibodies of other species may be advantageously employed for many uses (for example, in vitro or in situ detection assays, acute in vivo use, etc.). A humanized antibody may comprise amino acid residue substitutions, deletions, or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted, or added (i.e., mutated). Complete human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of an Ebola virus polypeptide.

Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such that the entire molecule is not naturally occurring. Examples of chimeric antibodies include those having a variable region derived from a non-human antibody and a human immunoglobulin constant region. The term is also intended to include antibodies having a variable region derived from one human antibody grafted to an immunoglobulin constant region of a predetermined sequences or the constant region from another human for which there are allotypic differences residing in the constant regions of any naturally occurring antibody having the variable regions, e.g., CDRs 1, 2, and 3 of the light and heavy chain. Human heavy chain genes exhibit structural polymorphism (allotypes) that are inherited as a haplotype. The serologically defined allotypes differ within and between population groups. See Jefferis et al. mAb, 1 (2009), pp. 332-338.

Smith et al. report a protocol for the production of antigen-specific chimeric human monoclonal antibodies (hmAbs) wherein antibody-secreting cells (ASCs) are isolated from whole blood collected after vaccination and sorted by flow cytometry into single cell plates. Nat Protoc. 2009; 4(3):372-84. The antibody genes of the ASCs are then amplified by RT-PCR and nested PCR, cloned into expression vectors and transfected into a human cell line. Meijer et al. report methods for isolation of human antibody repertoires with preservation of the natural heavy and light chain pairing. J Mol Biol. 2006 May 5; 358(3):764-72. Wrammert et al. report using immunoglobulin variable regions isolated from sorted single ASCs to produce human monoclonal antibodies (mAbs) that bound with high affinity. Nature. 2008 May 29; 453(7195): 667-671.

Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807, 715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an Fc RIIB polypeptide, that has been altered by the introduction of amino acid residue substitutions, deletions or additions (i.e., mutations).

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "Structural Determinants In the Sequences of Immunoglobulin Variable Domain," J. Mol. Biol. 278: 457-479 for a listing of human framework regions).

A humanized or non-naturally occurring chimeric Ebola virus antibody can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, an Ebola virus antibody also includes at least a portion of an immunoglobulin constant region (Fc), typically that of a human immunoglobulin. The constant domains of the Ebola virus antibodies may be selected with respect to the proposed function of the antibody, in particular the effector function which may be required. In some embodiments, the constant domains of the Ebola virus antibodies are (or comprise) human IgA, IgD, IgE, IgG or IgM domains. In a specific embodiment, human IgG constant domains, especially of the IgG1 and IgG3 isotypes are used, when the humanized Ebola virus antibodies is intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the Ebola virus antibody is intended for therapeutic purposes and antibody effector function is not required. The disclosure encompasses Fc constant domains comprising one or more amino acid modifications which alter antibody effector functions such as those disclosed in U.S. Patent Application Publication Nos. 2005/0037000 and 2005/0064514.

In some embodiments, the Ebola virus antibody contains both the light chain as well as at least the variable domain of a heavy chain. In other embodiments, the Ebola virus antibody may further include one or more of the CH1, hinge, CH2, CH3, and CH4 regions of the heavy chain. The antibody can be selected from any class of immunoglobulins, including IgM, IgG, IgD, IgA and IgE, and any isotype, including IgG1, IgG2, IgG3 and IgG4. In some embodiments, the constant domain is a complement fixing constant domain where it is desired that the antibody exhibits cytotoxic activity, and the class is typically IgG1. In other embodiments, where such cytotoxic activity is not desirable, the constant domain may be of the IgG2 class. The Ebola virus antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc. Natl. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

The antibodies used in the methods of the present disclosure may be monospecific. Also of interest are bispecific antibodies, trispecific antibodies or antibodies of greater multispecificity that exhibit specificity to different targets in the Ebola virus.

The antibodies of the present disclosure may be produced by any method known in the art useful for the production of polypeptides, e.g., in vitro synthesis, recombinant DNA production, and the like. Preferably, the antibodies are produced by recombinant DNA technology. The Ebola virus antibodies may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

Host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant Ebola virus antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the antibodies disclosed herein can be used to generate anti-idiotype antibodies using techniques well known to those skilled in the art (see, e.g., Greenspan, N. S. et al. (1989) "Idiotypes: Structure and Immunogenicity,"

FASEB J. 7:437-444; and Nisinoff, A. (1991) "Idiotypes: Concepts and Applications," J. Immunol. 147(8):2429-2438).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present disclosure include those disclosed in Brinkman, U. et al. (1995) "Phage Display Of Disulfide-Stabilized Fv Fragments," J. Immunol. Methods, 182:41-50, 1995; Ames, R. S. et al. (1995) "Conversion Of Murine Fabs Isolated From A Combinatorial Phage Display Library To Full Length Immunoglobulins," J. Immunol. Methods, 184:177-186; Kettleborough, C. A. et al. (1994) "Isolation Of Tumor Cell-Specific Single-Chain Fv From Immunized Mice Using Phage-Antibody Libraries And The Re-Construction Of Whole Antibodies From These Antibody Fragments," Eur. J. Immunol., 24:952-958, 1994; Persic, L. et al. (1997) "An Integrated Vector System For The Eukaryotic Expression Of Antibodies Or Their Fragments After Selection From Phage Display Libraries," Gene, 187:9-18; Burton, D. R. et al. (1994) "Human Antibodies From Combinatorial Libraries," Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art (such as those disclosed in PCT Publication WO 92/22324; Mullinax, R. L. et al. (1992) "Expression Of A Heterodimeric Fab Antibody Protein In One Cloning Step," BioTechniques, 12(6):864-869; and Sawai et al. (1995) "Direct Production Of The Fab Fragment Derived From The Sperm Immobilizing Antibody Using Polymerase Chain Reaction And cDNA Expression Vectors," Am. J. Reprod. Immunol. 34:26-34; and Better, M. et al. (1988) "*Escherichia coli* Secretion of an Active Chimeric Antibody Fragment," Science 240:1041-1043). Examples of techniques which can be used to produce single-chain Fvs and antibodies include those described in U.S. Pat. Nos. 4,946,778 and 5,258,498; Huston, J. S. et al. (1991) "Protein Engineering of Single-Chain Fv Analogs and Fusion Proteins," Methods in Enzymology 203:46-88; Shu, L. et al., "Secretion of a Single-Gene-Encoded Immunoglobulin from Myeloma Cells," Proc. Natl. Acad. Sci. (USA) 90:7995-7999; and Skerra. A. et al. (1988) "Assembly of a Functional Immunoglobulin Fv Fragment in *Escherichia coli*," Science 240:1038-1040.

Phage display technology can be used to increase the affinity of an antibody for Ebola virus. This technique would be useful in obtaining high affinity antibodies that could be used in the disclosed combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "Antibody Engineering by Codon-Based Mutagenesis in a Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155:1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567).

The disclosure contemplates the use of random mutagenesis to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see, Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155: 1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567).

Methods for accomplishing such affinity maturation are described for example in: Krause, J. C. et al. (2011) "An Insertion Mutation that Distorts Antibody Binding Site Architecture Enhances Function of a Human Antibody," MBio. 2(1) pii: e00345-10. doi: 10.1128/mBio.00345-10; Kuan, C. T. et al. (2010) "Affinity-Matured Anti-Glycoprotein NMB Recombinant Immunotoxins Targeting Malignant Gliomas and Melanomas," Int. J. Cancer 10.1002/ijc.25645; Hackel, B. J. et al. (2010) "Stability and CDR Composition Biases Enrich Binder Functionality Landscapes," J. Mol. Biol. 401(1):84-96; Montgomery, D. L. et al. (2009) "Affinity Maturation and Characterization of a Human Monoclonal Antibody Against HIV-1 gp41," MAbs 1(5):462-474; Gustchina, E. et al. (2009) "Affinity Maturation By Targeted Diversification of the CDR-H2 Loop of a Monoclonal Fab Derived From A Synthetic Naive Human Antibody Library And Directed Against The Internal Trimeric Coiled-Coil Of Gp41 Yields A Set Of Fabs With Improved HIV-1 Neutralization Potency And Breadth," Virology 393(1):112-119; Finlay, W. J. et al. (2009) "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol. 388(3):541-558; Bostrom, J. et al. (2009) "Improving Antibody Binding Affinity and Specificity for Therapeutic Development," Methods Mol. Biol. 525:353-376; Steidl, S. et al. (2008) "In Vitro Affinity Maturation of Human GM-CSF Antibodies by Targeted CDR-Diversification," Mol. Immunol. 46(1):135-144; and Barderas, R. et al. (2008) "Affinity Maturation of Antibodies Assisted by in Silico Modeling," Proc. Natl. Acad. Sci. (USA) 105(26):9029-9034.

In certain embodiments, the antibody, antigen binding fragment, the light chain, or the heavy chain comprises a non-naturally occurring chimeric amino acid sequence such that there is at least one mutation that is not present in naturally occurring antibodies comprising the six CDRs. In certain embodiments, the antibody, antigen binding fragment, or heavy chain, comprises a human constant domain from an immunoglobulin constant region (Fc) having one, two, three, four, five, six, or more of the following mutations G236A, S239D, A330L, I332E, S267E, L328F, P238D, H268F, S324T, S228P, G236R, L328R, L234A, L235A, M252Y, S254T, T256E, M428L, N434S. With regard to IgG-1 Fc mutations reported herein the sequences are in reference to following amino acid sequence (SEQ ID NO: 50) starting at amino acid 119: STKGPSVFP LAPSSKSTSG GTAALGCLVK DYFPEPVTVS WNSGALTSGV HTFPAVLQSS 178 GLYSLSSVVT VPSSSLGTQT YICNVNHKPS NTKVDKKVEP KSCDKTHTCP PCPAPELLGG 238 PSVFLFPPKP KDTLMISRTP EVTCVVVDVS HEDPEVKFNW YVDGVEVHN AKTKPREEQYN 298 STYRVVSVLT VLHQDWLNGK EYKCKVSNKA LPAPIEKTIS KAKGQPREPQ VYTLPPSRDE 358 LTKNQVSLTC LVKGFYPSDI AVEWESNGQP ENNYKTTPPV LDSDGSFFLY SKLTVDKSRW 418 QQGNVFSCSV MHEALHNHYT QKSLSLSPG.

In certain embodiments, this disclosure relates to antibodies reported wherein the constant region comprises a mutation that activates immune responses such as those selected from the constant region comprises as least one, two, three, or more mutations in the Fc domain selected from S239D, I332E, G236A, A330L, or combinations thereof.

FcgRIIb has immunosuppressive function. In certain embodiments, this disclosure relates to antibodies reported wherein the constant region comprises a mutation that suppressed immune responses those selected from the constant region comprises as least one, two, three, or more mutations in the Fc domain selected from S267E, L328F, P238D, or combinations thereof.

Antibodies interact with the complement cascade through C1q binding enabling antibodies to activate complement-dependent cytotoxicity (CDC). In certain embodiments, this disclosure relates to antibodies reported wherein the constant region comprises a mutation that effectively active complement-dependent cytotoxicity such as those selected from S267E, H268F, S324T, and combinations thereof.

In certain embodiment interaction with the immune system through Fc receptors may be unnecessary or undesirable, i.e., immune-silent antibodies. In certain embodiments, this disclosure relates to antibodies reported wherein the constant region comprises a mutation that bind the antigen but do not bind to FcgRs such as those selected from S228P, G236R, L328R, L234A, L235A, or combinations thereof.

In certain embodiments, it may be desirable to have antibodies wherein constant region of the Fc has been to increase or decrease antibody half-life. In certain embodiments, this disclosure relates to antibodies reported wherein the constant region comprises a mutation that increases or decreases the antibodies half-life such as those selected from M252Y, S254T, T256E, M428L, N434S or combinations thereof.

The disclosure particularly contemplates the production and use of "derivatives" of any of the above-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions, or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies, as well as variants having altered CH1, hinge, CH2, CH3 or CH4 regions, so as to form, for example antibodies, etc., having variant Fc regions that exhibit enhanced or impaired effector or binding characteristics.

The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "Lack of Fucose on Human IgG N-Linked Oligosaccharide Improves Binding to Human Fcgamma RIII and Antibody-Dependent Cellular Toxicity," J. Biol. Chem. 277(30): 26733-26740; Davies J. et al. (2001) "Expression of GnTIII in a Recombinant Anti-CD20 CHO Production Cell Line: Expression of Antibodies with Altered Glycoforms Leads to an Increase In ADCC Through Higher Affinity For FC Gamma RIII," Biotechnology & Bioengineering 74(4): 288-294). Methods of altering carbohydrate contents are known to those skilled in the art, see, e.g., Wallick, S. C. et al. (1988) "Glycosylation of a VH Residue of a Monoclonal Antibody Against Alpha (1-6) Dextran Increases its Affinity for Antigen," J. Exp. Med. 168(3): 1099-1109; Tao, M. H. et al. (1989) "Studies of Aglycosylated Chimeric Mouse-Human IgG. Role of Carbohydrate in the Structure and Effector Functions Mediated by the Human IgG Constant Region," J. Immunol. 143(8): 2595-2601; Routledge, E. G. et al. (1995) "The Effect of Aglycosylation on the Immunogenicity of a Humanized Therapeutic CD3 Monoclonal Antibody," Transplantation 60(8):847-53; Elliott, S. et al. (2003) "Enhancement of Therapeutic Protein in Vivo Activities Through Glycoengineering," Nature Biotechnol. 21:414-21; Shields, R. L. et al. (2002) "Lack of Fucose on Human IgG N-Linked Oligosaccharide Improves Binding to Human Fcgamma RM and Antibody-Dependent Cellular Toxicity," J. Biol. Chem. 277(30): 26733-26740).

In some embodiments, a humanized antibody is a derivative. Such a humanized antibody comprises amino acid residue substitutions, deletions, or additions in one or more CDRs. The humanized antibody derivative may have substantially the same binding, better binding, or worse binding when compared to a non-derivative humanized antibody. In specific embodiments, one, two, three, four, or five amino acid residues of the CDR have been substituted, deleted, or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present disclosure or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting, or adding) amino acid residues identified as involved in the interaction between the Fc domain and the FcRn receptor. The Ebola virus antibodies can be engineered to increase biological half-lives (see, e.g. U.S. Pat. No. 6,277,375). For example, Ebola virus antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The Ebola virus antibodies may also be modified by the methods and coupling agents described by Davis et al. (See U.S. Pat. No. 4,179,337) in order to provide compositions that can be injected into the mammalian circulatory system with substantially no immunogenic response.

One embodiment encompasses modification of framework residues of the Ebola virus antibodies. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "Reshaping Human Antibodies for Therapy," Nature 332:323-327).

Yet another embodiment encompasses Ebola virus antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: toxins (such as abrin, ricin A, pseudomonas exotoxin (i.e., PE-40), diphtheria toxin, ricin, gelonin, or pokeweed antiviral protein), proteins (such as tumor necrosis factor, interferon (e.g., alpha-interferon, beta-interferon), nerve growth factor, platelet derived growth factor, tissue plasminogen activator, or an apoptotic agent (e.g., tumor necrosis factor-alpha, tumor necrosis factor-bet.)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU™ (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or antimitotic agents (e.g., vincristine and vinblastine).

Techniques for conjugating such therapeutic moieties to antibodies are well known; see, e.g., Arnon et al., "Monoclonal Antibodies for Immunotargeting of Drugs in Cancer Therapy", in MONOCLONAL ANTIBODIES AND CANCER THERAPY, Reisfeld et al. (eds.), 1985, pp. 243-56, Alan R. Liss, Inc.); Hellstrom et al., "Antibodies for Drug Delivery", in CONTROLLED DRUG DELIVERY (2nd Ed.), Robinson et al. (eds.), 1987, pp. 623-53, Marcel Dekker, Inc.); Thorpe, "Antibody Carriers of Cytotoxic Agents in Cancer Therapy: A Review", in MONOCLONAL ANTIBODIES '84: BIOLOGICAL AND CLINICAL APPLICATIONS, Pinchera et al. (eds.), 1985, pp. 475-506); "Analysis, Results, and Future Prospective of the Therapeutic Use of Radiolabeled Antibody in Cancer Therapy", in MONOCLONAL ANTIBODIES FOR CANCER DETECTION AND THERAPY, Baldwin et al. (eds.), 1985, pp. 303-16, Academic Press; and Thorpe et al. (1982) "The Preparation and Cytotoxic Properties of Antibody-Toxin Conjugates," Immunol. Rev. 62:119-158.

In one embodiment, the Ebola virus antibodies or Ebola virus fusion molecules include an Fc portion. The Fc portion of such molecules may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "Humanized Porcine VCAM-Specific Monoclonal Antibodies with Chimeric IgG2/G4 Constant Regions Block Human Leukocyte Binding to Porcine Endothelial Cells," Mol. Immun 34(6):441-452, Swann, P. G. (2008) "Considerations for the Development of Therapeutic Monoclonal Antibodies," Curr. Opin. Immun. 20:493-499 (2008), and Presta, L. G. (2008) "Molecular Engineering and Design of Therapeutic Antibodies," Curr. Opin. Immun 20:460-470. In some embodiments, the Fc region is the native IgG1, IgG2, or IgG4 Fc region. In some embodiments, the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn, and IgG4 with serine at amino acid resident #228 in the hinge region changed to proline (S228P) to enhance stability. The Fc region may include the entire hinge region, or less than the entire hinge region.

Another embodiment includes IgG2-4 hybrids and IgG4 mutants that have reduced binding to FcR which increase their half-life. Representative IG2-4 hybrids and IgG4 mutants are described in Angal, S. et al. (1993) "A Single Amino Acid Substitution Abolishes the Heterogeneity of Chimeric Mouse/Human (IgG4) Antibody," Molec. Immunol. 30(1):105-108; Mueller, J. P. et al. (1997) "Humanized Porcine VCAM-Specific Monoclonal Antibodies With Chimeric IgG2/G4 Constant Regions Block Human Leukocyte Binding To Porcine Endothelial Cells," Mol. Immun 34(6): 441-452; and U.S. Pat. No. 6,982,323. In some embodiments the IgG1 and/or IgG2 domain is deleted for example, Angal, s. et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V3051 or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V3051 and P296L substitution. In another embodiment, the human IgG1 Fc domain variant contains an N297Q substitution, as this mutation abolishes FcR binding.

Substitutions, additions or deletions in the derivatized antibodies may be in the Fc region of the antibody and may thereby serve to modify the binding affinity of the antibody to one or more Fc R. Methods for modifying antibodies with modified binding to one or more Fc R are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

In some embodiments, the disclosure encompasses antibodies whose Fc region will have been modified so that the molecule will exhibit altered Fc receptor (FcR) binding activity, for example to exhibit decreased activity toward activating receptors such as FcgammaRIIA or FcgammaRIIIA, or increased activity toward inhibitory receptors such as FcgammaRIIB Preferably, such antibodies will exhibit decreased antibody-dependent cell-mediated cytotoxicity (ADCC) or complement dependent cytotoxicity (CDC) activities (relative to a wild-type Fc receptor).

Modifications that affect Fc-mediated effector function are well known in the art (see U.S. Pat. No. 6,194,551, and WO 00/42072; Stavenhagen, J. B. et al. (2007) "Fc Optimization Of Therapeutic Antibodies Enhances Their Ability To Kill Tumor Cells In Vitro And Controls Tumor Expansion In Vivo Via Low-Affinity Activating Fcgamma Receptors," Cancer Res. 57(18):8882-8890; Shields, R. L. et al. (2001) "High Resolution Mapping of the Binding Site on Human IgG1 for FcgammaRI, FcgammaRII, FcgammaRIII, and FcRn and Design of IgG1 Variants with Improved Binding to the Fc.gamma.R," J. Biol. Chem. 276(9):6591-6604). Exemplary variants of human IgG1 Fc domains with reduced binding to FcgammaRIIA or FcgammaRIIIA, but unchanged or enhanced binding to FcgammaRIIB, include S239A, H268A, S267G, E269A, E293A, E293D, Y296F, R301A, V303A, A327G, K322A, E333A, K334A, K338A, A339A, D376A.

In some embodiments, the disclosure encompasses antibodies whose Fc region will have been deleted (for example, a Fab or F(ab)$_2$, etc.).

Any of the molecules of the present disclosure can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "The Structure Of An Antigenic Determinant In A Protein," Cell, 37:767-778) and the "flag" tag (Knappik, A. et al. (1994) "An Improved Affinity Tag Based On The FLAG Peptide For The Detection And Purification Of Recombinant Antibody Fragments," Biotechniques 17(4):754-761).

In some embodiments, the antigen binding fragments may comprise one, two, or more of the CDRs or variable regions, e.g., a light chain variable region having a flexible linker such as a polyglycine, linked to the heavy chain variable region which is further fused to a polypeptide having a signal-transduction component of a T-cell antigen receptor domain, e.g., constant Fc domain or CD3-zeta. In certain embodiments, the signal-transduction component of the T-cell antigen receptor is a peptide with an immunoreceptor tyrosine-based activation motif with the consensus sequence YXXL(X)$_n$YXXL (SEQ ID NO: 61) wherein X is any amino acid L is leucine or isoleucine, wherein n is 6, 7, or 8. For example, the immunoreceptor tyrosine-based activation motif (underlined) is in the partial CD3-zeta sequences:

AQLPITEAQSFGLLDPKLCYLLDGILFIYGVILT-ALFLRVKFSRSADAPAYQQGQN QLYNELNLGR-REEYDVLDKRRGRDPEMGGKPRRKNPQEGLY-NELQKDKMAEAYSEI GMKGERRRGKGHDGLYQGLSTATKDTY-DALHMQALPPR (SEQ ID NO: 62) or AQLPITEA-QSFGLLDPKLCYLLDGILFIYGVILTALFLRVKFSRS-ADAPAYQQGQNQLYN ELNLGRREEYDVLDKRR-GRDPEMGGKPQRRKNPQEGLYNELQKDKMAEAY-SEIGMK GERRRGKGHDGLYQGLSTATKDTY-DALHMQALPPR (SEQ ID NO: 63) or AQLPITEAQSFGLLDPKLCYLLDGILFIYGVILT-ALFLRVKFSRSAEPPAYQQGQNQLYNE LNLGRREEY-DVLDKRRGRDPEMGGKPRRKNPQEGLYNELQKDK-MAEAYSEIGMKGE RRRGKGHDGLYQGLSTATKDTYDALHMQALPPR (SEQ ID NO: 64) or fragments or variants, e.g. having 1, 2, or 3 amino acid deletion, addition, or substitution variants, or a sequence with greater than 50, 60, 70, 80, 90, 95% or greater identity thereto.

In certain embodiments, the signal-transduction component of the T-cell antigen receptor is a peptide with a immunoreceptor tyrosine-based activation motif (underlined) with the sequence of immunoglobulin epsilon receptor subunit gamma precursor EPQLCYILDAILFLY-GIVLTLLYCRLKIQVRKAAITSYEKSDGVYTGLSTRNQETYETLK HE (SEQ ID NO: 65) fragments or variants thereof variants or a sequence with greater than 50, 60, 70, 80, 90, 95% or greater identity thereto.

The present disclosure also encompasses antibodies or their antigen-binding fragments that are conjugated to a diagnostic or therapeutic agent or any other molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present disclosure.

Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferon, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium (103Pd), phosphorous ($^{32}$P), praseodymium ($^{142}$Pr), promethium, ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$YB, $^{175}$Yb) yttrium ($^{90}$Y), zinc ($^{65}$Zn); positron emitting metals using various positron emission tomographies, and nonradioactive paramagnetic metal ions.

The molecules of the present disclosure can be conjugated to a second antibody to form an antibody heteroconjugate as described by Segal in U.S. Pat. No. 4,676,980. Such heteroconjugate antibodies may additionally bind to haptens (such as fluorescein, etc.), or to cellular markers (e.g., PD-1, 4-1-BB, B7-H4, B7-H5, CD4, CD8, CD14, CD25, CD27, CD28, CD40, CD68, CD163, CTLA4, GITR, LAG-3, OX40, TIM3, TIM4, TLR2, LIGHT, etc.) or to cytokines (e.g., IL-7, IL-15, IL-12, IL-4 TGF-beta, IL-10, IL-17, IFNg, Flt3, BLys) or chemokines (e.g., CCL21), etc.

The molecules of the present disclosure may be attached to solid supports, which are particularly useful for immunoassays or purification of the target antigen or of other molecules that are capable of binding to target antigen that has been immobilized to the support via binding to an antibody or antigen-binding fragment of the present disclosure. Such solid supports include, but are not limited to, glass, cellulose, polyacrylamide, nylon, polystyrene, polyvinyl chloride, or polypropylene.

The present disclosure additionally includes nucleic acid molecules (DNA or RNA) that encode any such antibodies, fusion proteins or fragments, as well as vector molecules (such as plasmids) that are capable of transmitting or of replication such nucleic acid molecules and expressing such antibodies, fusion proteins or fragments in a cell line. The nucleic acids can be single-stranded, double-stranded, and may contain both single-stranded and double-stranded portions.

Consensus Sequences

In certain embodiments, the disclosure relates to antibodies or fragments comprising six CDRs having consensus sequences.

Light chain CDR is of antibodies disclosed herein:

```
CDR 1
                                        (SEQ ID NO: 11)
RASQSISSFLN,

CDR 1
                                        (SEQ ID NO: 17)
RSSQSLLHRNGYNYLD,

CDR 1
                                        (SEQ ID NO: 29)
RASQSVSSSYLA,

CDR 1
                                        (SEQ ID NO: 35)
RASQRINNLVA.
```

Consensus sequences for light chain CDR 1:
CDR 1 (SEQ ID NO: 41) $RX^1SQXIX^2$, wherein $X^1$ is A, S, or any amino acid and $X^2$ is S, R, or any amino acid and
CDR 1 (SEQ ID NO: 42) $RX^1SQSX^2$, wherein $X^1$ is A, S, or any amino acid and $X^2$ is I, L, V, or any amino acid.

Light chain CDR 2s of antibodies disclosed herein:

```
CDR 2
                                        (SEQ ID NO: 12)
AASSLQS,

CDR 2
                                        (SEQ ID NO: 36)
DASSLKS,

CDR 2
                                        (SEQ ID NO: 18)
LGSNRAS,

CDR 2
                                        (SEQ ID NO: 24)
GNSNRPS,

CDR 2
                                        (SEQ ID NO: 30)
GAFNRAT.
```

Consensus sequences for light chain CDR 2s:
CDR 2 (SEQ ID NO: 43) $ASSLX^1S$, wherein $X^1$ is a Q, K, or any amino acid and
CDR 2 (SEQ ID NO: 44) $X^1SNRX^2S$, wherein $X^1$ is G, L, or any amino acid, and X is A, P, or any amino acid.

Light chain CDR 3s of antibodies disclosed herein:

```
CDR 3
                                        (SEQ ID NO: 13)
QQSYISPFT,

CDR 3
                                        (SEQ ID NO: 31)
QLYGSSPWT,

CDR 3
                                        (SEQ ID NO: 37)
QQYDTDSGWT.
```

Consensus sequences for light chain CDR 3s:
CDR 3 (SEQ ID NO: 45) $QX^1X^2X^3X^4SPX^5T$, wherein $X^1$ is Q, L, Y or any amino acid, $X^2$ is S, Y, D or any amino acid, $X^3$ is Y, G, T or any amino acid, $X^4$ is I, S, D or any amino acid, and $X^5$ is F, W or any amino acid.

Heavy Chain CDR is of antibodies disclosed herein:

```
CDR 1
                                        (SEQ ID NO: 14)
FTFRSYDMH,

CDR 1
                                        (SEQ ID NO: 20)
FAVRSNYLS,

CDR 1
                                        (SEQ ID NO: 26)
FTFSNAWMN,

CDR 1
                                        (SEQ ID NO: 32)
FTFSTYGMS,

CDR 1
                                        (SEQ ID NO: 38)
FTFSKYAMI.
```

Consensus sequences for heavy chain CDR 1:
CDR 1 (SEQ ID NO: 46)
$FX^1X^2RSX^3$ wherein $X^1$ is T, A, or any amino acid, $X^2$ is F, V, or any amino acid, and $X^3$ is Y, N, A or any amino acid and
CDR 1 (SEQ ID NO: 47)
$FTFX^1X^2YX^3M$, wherein $X^1$ is R, S, or any amino acid, $X^2$ is S, N, T, K, or any amino acid, $X^3$ D, Y, W, G, A, or any amino acid.

Heavy Chain CDR 2s of antibodies disclosed herein:

```
CDR 2
                                        (SEQ ID NO: 15)
IGTAGDTYYPGSVKG,

CDR 2
                                        (SEQ ID NO: 21)
LIYSGGLTAYADSVEG,

CDR 2
                                        (SEQ ID NO: 27)
RIKSKTDGGAADYAAPVKG,

CDR 2
                                        (SEQ ID NO: 33)
GISGSGGITYYADSVRG,

CDR 2
                                        (SEQ ID NO: 39)
GINKSGGRTYYADSVRG.
```

Consensus sequences for heavy chain CDR 2:
CDR 2 (SEQ ID NO: 48)
$GX^1X^2X^3YX^4X^5SVX^6G$, wherein $X^1$ is D, L, A, I, R, or any amino acid, $X^2$ is T, A, or any amino acid, $X^3$ is Y, A, D, or any amino acid, $X^4$ is P, A, or any amino acid, $X^5$ is K, E, R, or any amino acid and Heavy Chain CDR 3s of antibodies disclosed herein:

CDR 3
(SEQ ID NO: 16)
V R F G D T A V D Y
and

CDR 3
(SEQ ID NO: 22)
V A S S A G T F Y Y G M D V

Consensus sequences for heavy chain CDR 3:

CDR 3
(SEQ ID NO: 49)
VX$^1$X$^2$X$^3$X$^4$X$^5$X$^6$X$^7$X$^8$Y

Wherein X$^1$ is R, A, or any amino acid, X$^2$ is F, S or any amino acid, X$^3$ is G, S, or any amino acid, X$^4$ is D, A, or any amino acid, X$^5$ is T, G, or any amino acid, X$^6$ is A, T, or any amino acid, X$^7$ is V, F, or any amino acid, X$^8$ is D, Y, or any amino acid.

In certain embodiments, the disclosure relates to antibodies or fragments comprising six CDRs having the consensus sequences. With regard to the consensus sequences any of the amino acid positions may be desirable to substitute an amino acid that corresponds to the sequence in any antibody disclosed herein.

In certain embodiments, the disclosure relates to antibodies or fragments wherein the light chain comprises
a) a light chain CDR 1 selected from
 CDR 1 (SEQ ID NO: 41) RX$^1$SQXIX$^2$, wherein X$^1$ is A, S, or any amino acid and X$^2$ is S, R, or any amino acid
 and
 CDR 1 (SEQ ID NO: 42) RX$^1$SQSX$^2$, wherein X$^1$ is A, S, or any amino acid and X$^2$ is I, L, V, or any amino acid;
b) a light chain CDR 2 selected from:
 CDR 2 (SEQ ID NO: 43) ASSLX$^1$S, wherein X$^1$ is a Q, K, or any amino acid and
 CDR 2 (SEQ ID NO: 44) X$^1$SNRX$^2$S, wherein X$^1$ is G, L, or any amino acid, and X is A, P, or any amino acid; and
c) a light chain CDR 3 comprising (SEQ ID NO: 45) QX$^1$X$^2$X$^3$X$^4$SPX$^5$T, wherein X$^1$ is Q, L, Y or any amino acid, X$^2$ is S, Y, D or any amino acid, X$^3$ is Y, G, T or any amino acid, X$^4$ is I, S, D or any amino acid, and X$^5$ is F, W or any amino acid.

In certain embodiments, the disclosure relates to antibodies or fragments wherein the heavy chain comprises,
a) a heavy chain CDR 1 selected from (SEQ ID NO: 46) FX$^1$X$^2$RSX$^3$ wherein X$^1$ is T, A, or any amino acid, X$^2$ is F, V, or any amino acid, and X$^3$ is Y, N, A or any amino acid and CDR 1 (SEQ ID NO: 47) FTFX$^1$X$^2$YX$^3$M, wherein X$^1$ is R, S, or any amino acid, X$^2$ is S, N, T, K, or any amino acid, X$^3$ D, Y, W, G, A, or any amino acid;
b) a heavy chain CDR 2 having (SEQ ID NO: 48) GX$^1$X$^2$X$^3$YX$^4$X$^5$SVX$^6$G, wherein X$^1$ is D, L, A, I, R, or any amino acid, X$^2$ is T, A, or any amino acid, X$^3$ is Y, A, D, or any amino acid, X$^4$ is P, A, or any amino acid, X$^5$ is K, E, R, or any amino acid; and
c) a heavy chain CDR 3 having (SEQ ID NO: 49) VX$^1$X$^2$X$^3$X$^4$X$^5$X$^6$X$^7$X$^8$Y, wherein X$^1$ is R, A, or any amino acid, X$^2$ is F, S or any amino acid, X$^3$ is G, S, or any amino acid, X$^4$ is D, A, or any amino acid, X$^5$ is T, G, or any amino acid, X$^6$ is A, T, or any amino acid, X$^7$ is V, F, or any amino acid, X$^8$ is D, Y, or any amino acid.

In certain embodiments, the disclosure relates to antibodies or fragments wherein the light chain comprises
 a CDR 1 having CDR 1 (SEQ ID NO: 41) RX$^1$SQXIX$^2$, wherein X$^1$ is A, S, or any amino acid and X$^2$ is S, R, or any amino acid,
 a CDR 2 having CDR 2 (SEQ ID NO: 43) ASSLX$^1$S, wherein X$^1$ is a Q, K, or any amino acid, and
 a CDR 3 (SEQ ID NO: 45) QX$^1$X$^2$X$^3$X$^4$SPX$^5$T, wherein X$^1$ is Q, L, Y or any amino acid, X$^2$ is S, Y, D or any amino acid, X$^3$ is Y, G, T or any amino acid, X$^4$ is I, S, D or any amino acid, and X$^5$ is F, W or any amino acid, and the heavy chain comprises
 a CDR 1 (SEQ ID NO: 46)
 FX$^1$X$^2$RSX$^3$ wherein X$^1$ is T, A, or any amino acid, X$^2$ is F, V, or any amino acid, and X$^3$ is Y, N, A, or any amino acid,
 a CDR 2 (SEQ ID NO: 48)
 GX$^1$X$^2$X$^3$YX$^4$X$^5$SVX$^6$G, wherein X$^1$ is D, L, A, I, R, or any amino acid, X$^2$ is T, A, or any amino acid, X$^3$ is Y, A, D, or any amino acid, X$^4$ is P, A, or any amino acid, X$^5$ is K, E, R, or any amino acid; and
 a CDR 3 (SEQ ID NO: 49)
 VX$^1$X$^2$X$^3$X$^4$X$^5$X$^6$X$^7$X$^8$Y, wherein X$^1$ is R, A, or any amino acid, X$^2$ is F, S or any amino acid, X$^3$ is G, S, or any amino acid, X$^4$ is D, A, or any amino acid, X$^5$ is T, G, or any amino acid, X$^6$ is A, T, or any amino acid, X$^7$ is V, F, or any amino acid, X$^8$ is D, Y, or any amino acid.

Therapeutic Methods

In certain embodiments, the disclosure relates to methods of preventing or treating an Ebola virus infection comprising administering an effective amount of a pharmaceutical composition comprising an antibody or antigen binding fragment disclosed herein to a subject in need thereof. Treatment of a subject with a therapeutically or prophylactically effective amount of antibody or antibody binding fragment can include a single treatment or, preferably, can include a series of treatments. In certain embodiments, the subject is at risk of, exhibiting symptoms of, or diagnosed with an Ebola virus infection.

In certain embodiments, the antibody or antigen binding fragment is administered in combination with another or second therapeutic agent or antiviral agent. In certain embodiments, the antiviral agent(s) is abacavir, acyclovir, acyclovir, adefovir, amantadine, amprenavir, ampligen, arbidol, atazanavir, atripla, boceprevir, cidofovir, combivir, Complera™, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, saquinavir, stavudine, Stribild™, tenofovir, tenofovir disoproxil, tenofovir alafenamide fumarate, tipranavir, trifluridine, trizivir, tromantadine, truvada, valaciclovir, valganciclovir, vicriviroc, vidarabine, viramidine, zalcitabine, zanamivir, or zidovudine, and combinations thereof.

In certain embodiments, the other or second therapeutic agent may be monoclonal antibodies (mAbs) targeting the Ebola virus surface glycoprotein (GP) such as ZMAb (mAbs 2G4, 4G7, and 1H3) or MB-003 (mAbs 13C6, 6D8, and 13F6) or human chimera thereof. See Zeitlin et al., Enhanced potency of a fucose-free monoclonal antibody being developed as an Ebola virus immunoprotectant. Proc. Natl. Acad. Sci. U.S.A. 108, 20690-20694 (2011). The original murine 13F6 variable regions were deimmunized and were subsequently chimerized with human constant regions, containing an alanine at N297 of the human IgG1 heavy-chain constant region (h-13F6agly) to eliminate Fc glycosylation entirely. In certain embodiments, the disclosure contemplates that N297 may be substituted to any other nucleic acid such as G, A, S, T, C, V, L, I, M, F, Y, P, W, D, E, H, K, or R. Other contemplated agents include interfering RNA (siRNA) or antisense oligonucleotides molecules, e.g., phosphorodiamidate morpholino oligomers (PMOs), that target Ebola mRNA.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity, the route of administration, as well as age, body weight, response, and the past medical history of the patient. Suitable regimens can be selected by one skilled in the art by considering such factors and by following, for example, dosages reported in the literature and recommended in the Physician's Desk Reference (56th Ed., 2002).

Various delivery systems are known and can be used to administer the therapeutic or prophylactic compositions, e.g., encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

Methods of administering antibodies and antigen binding fragments include, but are not limited to, parenteral administration (e.g., intradermal, intramuscular, intraperitoneal, intravenous, and subcutaneous), epidural, and mucosal (e.g., intranasal and oral routes). In a specific embodiment, the antibodies or fusion proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934, 272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as Silastic™ membranes, or fibers.

In some embodiments, the antibodies or antigen binding fragments are formulated in liposomes for targeted delivery of the antibodies or fusion proteins. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 can be used to make liposomes-antibody compositions. Preferred liposomes are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces opsonization with serum components and reduces recognition by MPS. Sterically stabilized liposomes are preferably prepared using polyethylene glycol. For preparation of liposomes and sterically stabilized liposome, see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the disclosed compositions and methods can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody, e.g., F(ab'), may be conjugated to the liposomes using previously described methods, see, e.g., Martin et al., 1982, J. Biol. Chem. 257: 286-288.

The antibodies, or antigen binding fragments may also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, Stealth Liposomes, Boca Rotan: CRC Press, 233-44; Hansen et al., 1995, Biochim. Biophys. Acta, 1239: 133-144. In most preferred embodiments, immunoliposomes for use in the disclosed methods and compositions are further sterically stabilized. Preferably, the antibodies or antigen binding fragments are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phosphatidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, Biochemistry, 35: 1100-1105; Loughrey et al., 1987, Biochim. Biophys. Acta, 901: 157-160; Martin et al., 1982, J. Biol. Chem. 257: 286-288; Martin et al., 1981, Biochemistry, 20: 4429-38. Although not intending to be bound by a particular mechanism of action, immunoliposomal formulations including an antibody or fusion protein are particularly effective as therapeutic agents, since they deliver the antibody or fusion protein to the cytoplasm of the target cell, i.e., the cell comprising the receptor to which the antibody or fusion protein binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions include one or more vesicle forming lipids, an antibody or a fragment or derivative thereof or a fusion protein, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations are known to one skilled in the art and encompassed within the invention. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al., 1994, Immunomethods, 4: 259-72; Maruyama, 2000, Biol. Pharm. Bull. 23(7): 791-799; Abra et al., 2002, Journal of Liposome Research, 12(1&2): 1-3; Park, 2002, Bioscience Reports, 22(2): 267-281; Bendas et al., 2001 BioDrugs, 14(4): 215-224, J. Thomas August, ed., 1997, Gene Therapy: Advances in Pharmacology, Volume 40, Academic Press, San Diego, Calif., p. 399-435.

The antibodies and antigen binding fragments can be packaged in a hermetically sealed container, such as an ampoule or sachette, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies or fusion proteins are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies or antigen binding fragments should be stored at between 2 and 8 degrees C. in their original container and the antibodies should be administered within 12 hours, preferably within 6 hours, within 5 hours, within 3 hours, or within 1 hour after being reconstituted. In an alternative embodiment, antibodies or fusion proteins are supplied in liquid form in a hermetically sealed container indicating the quantity and concentration of the antibody, fusion protein, or conjugated molecule. Preferably, the liquid form of the antibodies or fusion proteins are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies of fusion proteins.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof, or fusion proteins may be reduced by enhancing uptake and tissue penetration of the antibodies or fusion proteins by modifications such as, for example, lipidation.

In certain embodiments, the therapeutic or prophylactic composition is a nucleic acid encoding an Ebola antibody or an antigen-binding fragment thereof. The nucleic acid can be administered in vivo to promote expression of its encoded antibody or fragment, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, the disclosed compositions include a prophylactically or therapeutically effective amount of antibody or fusion protein and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with antibody or antigen binding fragment. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more antibodies or antigen binding fragments. In another embodiment, a kit further comprises one or more other prophylactic or therapeutic agents useful for the treatment of Ebola infection, in one or more containers.

Diagnostic Methods

The Ebola antibodies and their antigen-binding fragments disclosed herein can be used for diagnostic purposes, such as to detect, diagnose, or monitor Ebola infections. The invention provides for the detection or diagnosis of infection comprising: (a) assaying a sample for Ebola or in a tissue sample of a subject using one or more antibodies (or fragments thereof) that immunospecifically bind to Ebola particles comprising the epitopes; and (b) comparing the level of the Ebola with a control level, e.g., levels in normal tissue samples, whereby an increase or decrease in the assayed level of Ebola compared to the control level is indicative of the infection. Such antibodies and fragments are preferably employed in immunoassays, such as the enzyme linked immunosorbent assay (ELISA), the radioimmunoassay (MA) and fluorescence-activated cell sorting (FACS).

One embodiment relates to the use of such antibodies and fragments, and particularly such antibodies and fragments that bind to human Ebola, as reagents for detection of Ebola in a sample or at a site of in vivo dormancy. Thus, the antibodies and fragments of the present invention have utility in the detection and diagnosis of an infection in a human. In one embodiment, such diagnosis comprises: a) administering to a subject (for example, parenterally, subcutaneously, or intraperitoneally) an effective amount of a labeled antibody or antigen-binding fragment that immunospecifically binds to Ebola particles; b) waiting for a time interval following the administration for permitting the labeled molecule to preferentially concentrate at sites in the subject where Ebola is (and for unbound labeled molecule to be cleared to background level); c) determining background level; and d) detecting the labeled antibody in the subject, such that detection of labeled antibody above the background level indicates that the subject has the infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of an infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the disclosed diagnostic methods include, but are not limited to, computed tomography (CT), whole body scan such as position emission tomography (PET), magnetic resonance imaging (MRI), and sonography.

In a specific embodiment, the antibody or antigen binding fragment is labeled with a radioisotope and is detected in the patient using a radiation responsive surgical instrument (Thurston et al., U.S. Pat. No. 5,441,050). In another embodiment, the antibody or antigen binding fragment is labeled with a fluorescent compound and is detected in the patient using a fluorescence responsive scanning instrument. In another embodiment, the antibody or antigen binding fragment is labeled with a positron emitting metal and is detected in the patient using positron emission-tomography. In yet another embodiment, the antibody or antigen binding fragment is labeled with a paramagnetic label and is detected in a patient using magnetic resonance imaging (MM).

EXAMPLES

Disclosed herein are monoclonal antibodies specific for the glycoprotein of Ebola virus that can be used as a neutralizing antibody, prophylactically treating those who have yet to develop symptoms, or for treating patients diagnosed with Ebola virus disease. In order to develop these antibodies, circulating B cells and plasma cells were collected from the blood of patients who had recovered from Ebola infection. The three cell populations (bulk activated B cells, bulk plasmablasts, and Ebola glycoprotein-binding B cells), were sorted so that virus-specific antibodies could be isolated. Antibody heavy and light chain variable region segments were then amplified by PCR from single sorted cells. These gene segments were cloned into expression vectors and the antibodies were produced and evaluated for their ability to neutralize Ebola virus infectivity in vitro. Over 1000 individual sequences were determined in order to identify 200 Ebola glycoprotein-binding antibodies. These were screened to determine their ability to neutralize Ebola virus in vitro.

Through in vitro studies, it was identified that several of the monoclonal antibodies that were generated have high affinity compared to the antibody component of ZMapp, monoclonal antibody for treating Ebola virus disease. Tables Below Show Data for Certain Antibodies.

| antibody | ELISA EC50 | | specificity | GP construct used for ELISA |
|---|---|---|---|---|
| 5.1.10B3 | 5.2 ng/ml | (35 pM) | New epitope | Delta mucin |
| 2.1.1D05 | 5.1 ng/ml | (34 pM) | New epitope | Delta mucin |
| 5.6.1A2 | 12 ng/ml | (80 pM) | Chalice base? | Delta mucin |
| 13C6 | 40 ng/ml | (270 pM) | Glycan cap | Delta mucin |
| 2G4 | 100 ng/ml | (670 pM) | Chalice base | Delta mucin |
| 1H3 | 400 ng/ml | (2.7 nM) | Glycan cap | Delta mucin |
| KZ52 | 40 ng/ml | (270 pM) | Chalice base | Delta mucin |
| 13F6 | 4 ng/ml | (2.7 pM) | Mucin domain | Full length GP |

| antibody | PRNT50 (ug/ml) for Ebola Zaire (Kikwit strain) |
|---|---|
| 5.6.c2618 (ATK-13) | 0.0061 |
| 9.6.3A06 | 0.0488 |
| 5.1.13G03 | 0.0978 |
| 5.6.1A02 | 0.195 |
| 2.1.7G07 | 1.57 |
| 2.1.1D07 | 6.25 |
| 5.1.10B03 | 3.13 |
| 2.1.1D05 | 3.13 |
| 5.1.7D03 | 1.57 |
| 9.6.1A09 | 0.78125 |
| 9.6.3D06 | 1.57 |
| 2.10.1E06 | 0.78125 |

Neutralizing Antibodies and their Properties are as Follows:

Antibody, 5.6.1A2, neutralizes Ebola virus in vitro with a PRNT50 value of below 100 ng/ml—this is comparable or superior to all previously described antibodies. The mouse protection data for 5.1.10B3 and 5.6.1A2 showed 80-90% protection when the antibodies were given one day prior to infection of the animals with Ebola virus, which is superior to the protection observed in previous studies. PRNT is a plaque reduction neutralization test standard for detecting and measuring antibodies that neutralize viruses; number represents the concentration of serum necessary to reduce the number of infected host cell plaques that form.

5.1.10B3—antibody source: bulk plasmablasts from EVD5 1 month; PRNT*80 of 3 ug/ml and PRNT50 of 25 ug/ml; protected 8/10 mice. Escape mutations map to GP base.

5.6.1A2—antibody source: GP binding cells from EVD5 6 months; PRNT80 of 98 ng/ml and PRNT50 not yet determined but less than 98 ng/ml; protected 9/10 mice. Escape mutations map to fusion loop.

2.1.1D05—antibody source: GP binding cells from EVD2 1 month; in vitro neutralization potency not yet determined; protected 3/10 mice. Escape mutations map to glycan cap.

2.1.1D07—antibody source: GP binding cells from EVD2 1 month.

9.6.3D6—antibody source: GP binding cells from EVD9 6 months; in vitro neutralization.

Strain-relevant binding affinity:
Ebola Zaire (Mayinga) GP—all
Bundibugyo GP—5.6.1A2, 9.6.3D6
Reston GP—2.1.1D05, 2.1.1D07, 5.6.1A2
Sudan GP—2.1.1D07

TABLE

Data for Select Antibodies

| mAb name | epitope location | 50% plaque reduction neutralization titer (PRNT50) for Ebola Zaire | 50% plaque reduction neutralization titer (PRNT50) for Ebola Sudan | % of mice protected from 100 p.f.u. Ebola challenge when antibody given 1 day prior to infection |
|---|---|---|---|---|
| 2.1.1B02 | mucin residues 478-490 | non-neutralizing | | 100% protection |
| 5.24.1C11 | fusion loop | <0.36 µg/ml | <0.36 µg/ml | |
| 9.20.1C03 | inner chalice bowl | <0.36 µg/ml | <0.36 µg/ml | |
| 5.24.1B03 Binds all filoviruses | glycan cap | non-neutralizing | | |
| 9.20.1D09 | chalice base | <0.36 µg/ml | 0.78 µg/ml | |
| 5.24.2A03 Binds all filoviruses | glycan cap | non-neutralizing | | |
| 9.20.1A02 | inner chalice bowl | <0.36 µg/ml | non-neutralizing | |
| 5.24.2C05 | chalice base | <0.36 µg/ml | 6.25 µg/ml | |
| 5.24.2B07 | inner chalice bowl | 1.56 µg/ml | 12.5 µg/ml | |

Methods for Production of the Antibodies Utilized Protocols Provided in the Following References.

Wrammert et al. report using immunoglobulin variable regions isolated from sorted single ASCs to produce human monoclonal antibodies (mAbs) that bound with high affinity. Nature. 2008 May 29; 453(7195): 667-671. Smith et al.

report a protocol for the production of antigen-specific human monoclonal antibodies (hmAbs) wherein antibody-secreting cells (ASCs) are isolated from whole blood collected after vaccination and sorted by flow cytometry into single cell plates. The antibody genes of the ASCs are then amplified by RT-PCR and nested PCR, cloned into expression vectors and transfected into a human cell line. See FIG. 1.

The complete sequence for a cloning vector for generating a chimeric antibody heavy chain with a human immunoglobulin G1 (AbVec-hIgG1) is found in GenBank ACCESSION FJ475055 which comprises a CMV promotor, murine IgG1 signal peptide, cloning site, Cgamma-1 (IgG1) constant region derived from *Homo sapiens* (SEQ ID NO: 66), followed by beta-lactamase which confers resistance to ampicillin.

In certain embodiments, antibodies or antigen binding fragments disclosed herein comprise a heavy chain constant region of with a sequence below or with a sequence having at least 80, 85, 90, 95, 98, 99%, or more identity or similarity. Heavy chain constant region sequence:

(SEQ ID NO: 66)
RSTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In certain embodiments, antibody or antigen binding fragment comprises the N297A mutation:

(SEQ ID NO: 67)
RSTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In certain embodiments, antibody or antigen binding fragment comprises the triple mutation M252Y/S254T/T256E mutation:

(SEQ ID NO: 68)
RSTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLYITREPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

```
                        SEQUENCE LISTING

Sequence total quantity: 218
SEQ ID NO: 1            moltype = AA  length = 107
FEATURE                 Location/Qualifiers
REGION                  1..107
                        note = Synthetic
source                  1..107
                        mol_type = protein
                        organism = synthetic construct
SEQUENCE: 1
DIQMTQSPSS LSASVGDRVT ITCRASQSIS SFLNWHQQKP GKAPKLLIYA ASSLQSGVPS   60
RFSGSGSGTD FTLTISSLQP EDFAIYYCQQ SYISPFTFGP GTKVDIK               107

SEQ ID NO: 2            moltype = AA  length = 118
FEATURE                 Location/Qualifiers
REGION                  1..118
                        note = Synthetic
source                  1..118
                        mol_type = protein
                        organism = synthetic construct
SEQUENCE: 2
EVQLVESGGG LVQPGGSLRL SCAASGFTFR SYDMHWVRQA TGKGLEWVSA IGTAGDTYYP   60
GSVKGRFTIS RENAKNSLYL QMNSLRAEDT AVYYCARVRF GDTAVDYWGQ GTLVTVSS   118

SEQ ID NO: 3            moltype = AA  length = 113
FEATURE                 Location/Qualifiers
REGION                  1..113
                        note = Synthetic
source                  1..113
                        mol_type = protein
                        organism = synthetic construct
SEQUENCE: 3
DIVMTQSPRS LSVTPGEPAS ISCRSSQSLL HRNGYNYLDW YLQKPGQSPQ LLIYLGSNRA   60
SGVPDRFSGS GSGTDFTLKI SRVEAEDVGV YYCMQALQTP SWTFGQGTKV EIK        113
```

-continued

```
SEQ ID NO: 4             moltype = AA  length = 122
FEATURE                  Location/Qualifiers
REGION                   1..122
                         note = Synthetic
source                   1..122
                         mol_type = protein
                         organism = synthetic construct
SEQUENCE: 4
EVQLVESGGG LIQPGGSLRL SCAASGFAVR SNYLSWVRQA PGKGLEWVSL IYSGGLTAYA   60
DSVEGRFTIS RDNSKNTLYL QMNSLRVEDT ALYYCARVAS SAGTFYYGMD VWGQGTTVTV  120
SS                                                                 122

SEQ ID NO: 5             moltype = AA  length = 112
FEATURE                  Location/Qualifiers
REGION                   1..112
                         note = Synthetic
source                   1..112
                         mol_type = protein
                         organism = synthetic construct
SEQUENCE: 5
QSVLTQPPSV SGAPGQRVTI SCTGSSSNIG AGYDVYWYQQ LPGTAPKLLI YGNSNRPSGV   60
PDRFSGSKSG TSASLAITGL QAEDEADYYC QSFDSSLRDS WVFGGGTKLT VL          112

SEQ ID NO: 6             moltype = AA  length = 120
FEATURE                  Location/Qualifiers
REGION                   1..120
                         note = Synthetic
source                   1..120
                         mol_type = protein
                         organism = synthetic construct
SEQUENCE: 6
EVQLVESGGG LVKPGGSLRL SCAASGFTFS NAWMNWVRQA PGKGLEWVGR IKSKTDGGAA   60
DYAAPVKGRF TISRDDSKNT LYLQMNSLKT EDTAVYFCTT VYRYNYDSVW GQGTLVTVSS  120

SEQ ID NO: 7             moltype = AA  length = 108
FEATURE                  Location/Qualifiers
REGION                   1..108
                         note = Synthetic
source                   1..108
                         mol_type = protein
                         organism = synthetic construct
SEQUENCE: 7
EIVLTQSPGT LSLSPGERAT LSCRASQSVS SSYLAWYQQK PGQAPRLLIY GAFNRATGIP   60
DRFSGSGSGT DFTLTISRLE PEDFAVYYCQ LYGSSPWTFG QGTKVEIK               108

SEQ ID NO: 8             moltype = AA  length = 120
FEATURE                  Location/Qualifiers
REGION                   1..120
                         note = Synthetic
source                   1..120
                         mol_type = protein
                         organism = synthetic construct
SEQUENCE: 8
EVQLLESGGG LVQPGGSLRL SCAASGFTFS TYGMSWVRQA PGKGLEWVSG ISGSGGITYY   60
ADSVRGRFTI SRDNSKNTLY LRMNSLRAED TAVYYCAKVG EYYDFWSGYS PFEYWGQGTL  120

SEQ ID NO: 9             moltype = AA  length = 108
FEATURE                  Location/Qualifiers
REGION                   1..108
                         note = Synthetic
source                   1..108
                         mol_type = protein
                         organism = synthetic construct
SEQUENCE: 9
DIQMTQSPST LSASVGDRVT ITCRASQRIN NLVAWYQQKP GKAPKVMIYD ASSLKSGVPS   60
RFSGSGSGTE FTLTISSLQP DDFATYFCQQ YDTDSGWTFG QGTKVEIK               108

SEQ ID NO: 10            moltype = AA  length = 129
FEATURE                  Location/Qualifiers
REGION                   1..129
                         note = Synthetic
source                   1..129
                         mol_type = protein
                         organism = synthetic construct
SEQUENCE: 10
EVQLLESGGG LVQPGGSLRL SCAASGFTFS KYAMIWVRQA PGKGLQWVAG INKSGGRTYY   60
ADSVRGRFTI SRDNSKNTLY LQMKSLRADD TAMYYCAKEG SPLSDVLLVA APFGWFDPWG  120
QGTLVTVSS                                                          129
```

```
SEQ ID NO: 11           moltype = AA   length = 11
FEATURE                 Location/Qualifiers
REGION                  1..11
                        note = Synthetic
source                  1..11
                        mol_type = protein
                        organism = synthetic construct
SEQUENCE: 11
RASQSISSFL N                                                                11

SEQ ID NO: 12           moltype = AA   length = 7
FEATURE                 Location/Qualifiers
REGION                  1..7
                        note = Synthetic
source                  1..7
                        mol_type = protein
                        organism = synthetic construct
SEQUENCE: 12
AASSLQS                                                                     7

SEQ ID NO: 13           moltype = AA   length = 9
FEATURE                 Location/Qualifiers
REGION                  1..9
                        note = Synthetic
source                  1..9
                        mol_type = protein
                        organism = synthetic construct
SEQUENCE: 13
QQSYISPFT                                                                   9

SEQ ID NO: 14           moltype = AA   length = 9
FEATURE                 Location/Qualifiers
REGION                  1..9
                        note = Synthetic
source                  1..9
                        mol_type = protein
                        organism = synthetic construct
SEQUENCE: 14
FTFRSYDMH                                                                   9

SEQ ID NO: 15           moltype = AA   length = 10
FEATURE                 Location/Qualifiers
REGION                  1..10
                        note = Synthetic
source                  1..10
                        mol_type = protein
                        organism = synthetic construct
SEQUENCE: 15
IGTAGDTYYP                                                                  10

SEQ ID NO: 16           moltype = AA   length = 10
FEATURE                 Location/Qualifiers
REGION                  1..10
                        note = Synthetic
source                  1..10
                        mol_type = protein
                        organism = synthetic construct
SEQUENCE: 16
VRFGDTAVDY                                                                  10

SEQ ID NO: 17           moltype = AA   length = 16
FEATURE                 Location/Qualifiers
REGION                  1..16
                        note = Synthetic
source                  1..16
                        mol_type = protein
                        organism = synthetic construct
SEQUENCE: 17
RSSQSLLHRN GYNYLD                                                           16

SEQ ID NO: 18           moltype = AA   length = 7
FEATURE                 Location/Qualifiers
REGION                  1..7
                        note = Synthetic
source                  1..7
                        mol_type = protein
                        organism = synthetic construct
SEQUENCE: 18
```

```
LGSNRAS                                                                         7

SEQ ID NO: 19           moltype = AA   length = 10
FEATURE                 Location/Qualifiers
REGION                  1..10
                        note = Synthetic
source                  1..10
                        mol_type = protein
                        organism = synthetic construct
SEQUENCE: 19
MQALQTPSWT                                                                     10

SEQ ID NO: 20           moltype = AA   length = 9
FEATURE                 Location/Qualifiers
REGION                  1..9
                        note = Synthetic
source                  1..9
                        mol_type = protein
                        organism = synthetic construct
SEQUENCE: 20
FAVRSNYLS                                                                       9

SEQ ID NO: 21           moltype = AA   length = 16
FEATURE                 Location/Qualifiers
REGION                  1..16
                        note = Synthetic
source                  1..16
                        mol_type = protein
                        organism = synthetic construct
SEQUENCE: 21
LIYSGGLTAY ADSVEG                                                              16

SEQ ID NO: 22           moltype = AA   length = 14
FEATURE                 Location/Qualifiers
REGION                  1..14
                        note = Synthetic
source                  1..14
                        mol_type = protein
                        organism = synthetic construct
SEQUENCE: 22
VASSAGTFYY GMDV                                                                14

SEQ ID NO: 23           moltype = AA   length = 14
FEATURE                 Location/Qualifiers
REGION                  1..14
                        note = Synthetic
source                  1..14
                        mol_type = protein
                        organism = synthetic construct
SEQUENCE: 23
TGSSSNIGAG YDVY                                                                14

SEQ ID NO: 24           moltype = AA   length = 7
FEATURE                 Location/Qualifiers
REGION                  1..7
                        note = Synthetic
source                  1..7
                        mol_type = protein
                        organism = synthetic construct
SEQUENCE: 24
GNSNRPS                                                                         7

SEQ ID NO: 25           moltype = AA   length = 12
FEATURE                 Location/Qualifiers
REGION                  1..12
                        note = Synthetic
source                  1..12
                        mol_type = protein
                        organism = synthetic construct
SEQUENCE: 25
QSFDSSLRDS WV                                                                  12

SEQ ID NO: 26           moltype = AA   length = 9
FEATURE                 Location/Qualifiers
REGION                  1..9
                        note = Synthetic
source                  1..9
                        mol_type = protein
                        organism = synthetic construct
```

```
SEQUENCE: 26
FTFSNAWMN                                                                   9

SEQ ID NO: 27           moltype = AA  length = 19
FEATURE                 Location/Qualifiers
REGION                  1..19
                        note = Synthetic
source                  1..19
                        mol_type = protein
                        organism = synthetic construct
SEQUENCE: 27
RIKSKTDGGA ADYAAPVKG                                                       19

SEQ ID NO: 28           moltype = AA  length = 9
FEATURE                 Location/Qualifiers
REGION                  1..9
                        note = Synthetic
source                  1..9
                        mol_type = protein
                        organism = synthetic construct
SEQUENCE: 28
VYRYNYDSV                                                                   9

SEQ ID NO: 29           moltype = AA  length = 12
FEATURE                 Location/Qualifiers
REGION                  1..12
                        note = Synthetic
source                  1..12
                        mol_type = protein
                        organism = synthetic construct
SEQUENCE: 29
RASQSVSSSY LA                                                              12

SEQ ID NO: 30           moltype = AA  length = 7
FEATURE                 Location/Qualifiers
REGION                  1..7
                        note = Synthetic
source                  1..7
                        mol_type = protein
                        organism = synthetic construct
SEQUENCE: 30
GAFNRAT                                                                     7

SEQ ID NO: 31           moltype = AA  length = 9
FEATURE                 Location/Qualifiers
REGION                  1..9
                        note = Synthetic
source                  1..9
                        mol_type = protein
                        organism = synthetic construct
SEQUENCE: 31
QLYGSSPWT                                                                   9

SEQ ID NO: 32           moltype = AA  length = 9
FEATURE                 Location/Qualifiers
REGION                  1..9
                        note = Synthetic
source                  1..9
                        mol_type = protein
                        organism = synthetic construct
SEQUENCE: 32
FTFSTYGMS                                                                   9

SEQ ID NO: 33           moltype = AA  length = 17
FEATURE                 Location/Qualifiers
REGION                  1..17
                        note = Synthetic
source                  1..17
                        mol_type = protein
                        organism = synthetic construct
SEQUENCE: 33
GISGSGGITY YADSVRG                                                         17

SEQ ID NO: 34           moltype = AA  length = 16
FEATURE                 Location/Qualifiers
REGION                  1..16
                        note = Synthetic
source                  1..16
                        mol_type = protein
```

```
                            organism = synthetic construct
SEQUENCE: 34
VGEYYDFWSG YSPFEY                                                     16

SEQ ID NO: 35               moltype = AA   length = 11
FEATURE                     Location/Qualifiers
REGION                      1..11
                            note = Synthetic
source                      1..11
                            mol_type = protein
                            organism = synthetic construct
SEQUENCE: 35
RASQRINNLV A                                                          11

SEQ ID NO: 36               moltype = AA   length = 7
FEATURE                     Location/Qualifiers
REGION                      1..7
                            note = Synthetic
source                      1..7
                            mol_type = protein
                            organism = synthetic construct
SEQUENCE: 36
DASSLKS                                                               7

SEQ ID NO: 37               moltype = AA   length = 10
FEATURE                     Location/Qualifiers
REGION                      1..10
                            note = Synthetic
source                      1..10
                            mol_type = protein
                            organism = synthetic construct
SEQUENCE: 37
QQYDTDSGWT                                                            10

SEQ ID NO: 38               moltype = AA   length = 9
FEATURE                     Location/Qualifiers
REGION                      1..9
                            note = Synthetic
source                      1..9
                            mol_type = protein
                            organism = synthetic construct
SEQUENCE: 38
FTFSKYAMI                                                             9

SEQ ID NO: 39               moltype = AA   length = 17
FEATURE                     Location/Qualifiers
REGION                      1..17
                            note = Synthetic
source                      1..17
                            mol_type = protein
                            organism = synthetic construct
SEQUENCE: 39
GINKSGGRTY YADSVRG                                                    17

SEQ ID NO: 40               moltype = AA   length = 20
FEATURE                     Location/Qualifiers
REGION                      1..20
                            note = Synthetic
source                      1..20
                            mol_type = protein
                            organism = synthetic construct
SEQUENCE: 40
EGSPLSDVLL VAAPFGWFDP                                                 20

SEQ ID NO: 41               moltype = AA   length = 7
FEATURE                     Location/Qualifiers
REGION                      1..7
                            note = Synthetic
REGION                      1..7
                            note = X - X is any amino acid
source                      1..7
                            mol_type = protein
                            organism = synthetic construct
SEQUENCE: 41
RXSQXIX                                                               7

SEQ ID NO: 42               moltype = AA   length = 6
FEATURE                     Location/Qualifiers
REGION                      1..6
```

```
                        note = Synthetic
REGION                  1..6
                        note = X - X is any amino acid
source                  1..6
                        mol_type = protein
                        organism = synthetic construct
SEQUENCE: 42
RXSQSX                                                                          6

SEQ ID NO: 43           moltype = AA  length = 6
FEATURE                 Location/Qualifiers
REGION                  1..6
                        note = Synthetic
REGION                  1..6
                        note = X - X is any amino acid
source                  1..6
                        mol_type = protein
                        organism = synthetic construct
SEQUENCE: 43
ASSLXS                                                                          6

SEQ ID NO: 44           moltype = AA  length = 6
FEATURE                 Location/Qualifiers
REGION                  1..6
                        note = Synthetic
REGION                  1..6
                        note = X - X is any amino acid
source                  1..6
                        mol_type = protein
                        organism = synthetic construct
SEQUENCE: 44
XSNRXS                                                                          6

SEQ ID NO: 45           moltype = AA  length = 9
FEATURE                 Location/Qualifiers
REGION                  1..9
                        note = Synthetic
REGION                  1..9
                        note = X - X is any amino acid
source                  1..9
                        mol_type = protein
                        organism = synthetic construct
SEQUENCE: 45
QXXXXSPXT                                                                       9

SEQ ID NO: 46           moltype =   length =
SEQUENCE: 46
000

SEQ ID NO: 47           moltype = AA  length = 8
FEATURE                 Location/Qualifiers
REGION                  1..8
                        note = Synthetic
REGION                  1..8
                        note = X - X is any amino acid
source                  1..8
                        mol_type = protein
                        organism = synthetic construct
SEQUENCE: 47
FTFXXYXM                                                                        8

SEQ ID NO: 48           moltype = AA  length = 11
FEATURE                 Location/Qualifiers
REGION                  1..11
                        note = Synthetic
REGION                  1..11
                        note = X - X is any amino acid
source                  1..11
                        mol_type = protein
                        organism = synthetic construct
SEQUENCE: 48
GXXXYXXSVX G                                                                   11

SEQ ID NO: 49           moltype =   length =
SEQUENCE: 49
000

SEQ ID NO: 50           moltype = AA  length = 328
FEATURE                 Location/Qualifiers
```

```
source                      1..328
                            mol_type = protein
                            organism = Homo sapiens
SEQUENCE: 50
STKGPSVFPL APSSKSTSGG TAALGCLVKD YFPEPVTVSW NSGALTSGVH TFPAVLQSSG    60
LYSLSSVVTV PSSSLGTQTY ICNVNHKPSN TKVDKKVEPK SCDKTHTCPP CPAPELLGGP   120
SVFLFPPKPK DTLMISRTPE VTCVVVDVSH EDPEVKFNWY VDGVEVHNAK TKPREEQYNS   180
TYRVVSVLTV LHQDWLNGKE YKCKVSNKAL PAPIEKTISK AKGQPREPQV YTLPPSRDEL   240
TKNQVSLTCL VKGFYPSDIA VEWESNGQPE NNYKTTPPVL DSDGSFFLYS KLTVDKSRWQ   300
QGNVFSCSVM HEALHNHYTQ KSLSLSPG                                     328

SEQ ID NO: 51               moltype = DNA   length = 321
FEATURE                     Location/Qualifiers
misc_feature                1..321
                            note = Synthetic
source                      1..321
                            mol_type = other DNA
                            organism = synthetic construct
SEQUENCE: 51
gacatccaga tgacccagtc tccatcctcc ctgtctgcat ctgtaggaga cagagtcacc    60
atcacttgcc gggcaagtca gagcattagc agcttttaa attggcatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caatttacta ctgtcaacag agttacattt ccccattcac tttcggccct   300
gggaccaaag tggatatcaa a                                            321

SEQ ID NO: 52               moltype = DNA   length = 356
FEATURE                     Location/Qualifiers
misc_feature                1..356
                            note = Synthetic
source                      1..356
                            mol_type = other DNA
                            organism = synthetic construct
SEQUENCE: 52
gaggtgcagc tggtggagtc tgggggaggc ttggtacagc ctggggggtc cctgagactc    60
tcctgtgcag cctctggatt caccttcaga agctacgaca tgcactgggt ccgccaagct   120
acaggaaaag gtctggagtg ggtctcagct attggtactg ctggtgacac atactatcca   180
ggctccgtga agggccgatt caccatctcc agagaaaatg ccaagaactc cttgtatctt   240
caaatgaaca gcctgagagc cgaggacacg gccgtgtatt actgtgcaag agtccgtttc   300
ggggatacag ccgttgacta ctggggccag ggaaccctgg tcaccgtctc ctcagc       356

SEQ ID NO: 53               moltype = DNA   length = 339
FEATURE                     Location/Qualifiers
misc_feature                1..339
                            note = Synthetic
source                      1..339
                            mol_type = other DNA
                            organism = synthetic construct
SEQUENCE: 53
gatattgtga tgactcagtc tccacgctcc ctgtccgtca cccctggaga gccggcctcc    60
atctcctgca ggtctagtca gagcctcctg catagaaatg gatataacta tttggattgg   120
tatctgcaga agccagggca gtctccacac ctcctgatct atttgggttc taatcgggcc   180
tccggggtcc ctgacaggtt cagtggcagt ggatcaggca cagattttac actgaaaatc   240
agcagagtgg aggctgaaga tgttggggtt tattactgca tgcaagctct acaaactccc   300
tcgtggacgt tcggccaagg gaccaaggtg gaaatcaaa                          339

SEQ ID NO: 54               moltype = DNA   length = 368
FEATURE                     Location/Qualifiers
misc_feature                1..368
                            note = Synthetic
source                      1..368
                            mol_type = other DNA
                            organism = synthetic construct
SEQUENCE: 54
gaggtgcagc tggtggagtc aggaggaggc ttgatccagc ctgggggtc cctgagactc     60
tcctgtgcag cctctggttt cgccgtcagg agcaactact tgagctgggt ccgccaggct   120
cctgggaagg ggctggagtg ggtctcactt atttatagtg gtggtctcac agcctacgca   180
gactccgtgg agggccggtt caccatctcc agagacaatt ctaagaacac actatatctt   240
caaatgaaca gcctgagagt cgaggacacg gcccctatatt actgtgcgag agtcgcatca   300
tcggctggaa ccttctacta cggtatggac gtctggggcc aagggaccac ggtcaccgtc   360
tcctcagc                                                            368

SEQ ID NO: 55               moltype = DNA   length = 336
FEATURE                     Location/Qualifiers
misc_feature                1..336
                            note = Synthetic
source                      1..336
                            mol_type = other DNA
                            organism = synthetic construct
```

```
SEQUENCE: 55
cagtctgtgc tgacgcagcc gccctcagtg tctggggccc cagggcagag ggtcaccatc    60
tcctgcactg ggagcagttc caacatcggg gcaggttatg atgtatactg gtaccagcag   120
cttccaggaa cagcccccaa actcctcatc tatggtaaca gcaatcggcc ctcagggg tc   180
cctgaccgat tctctggctc caagtctggc acctcagcct ccctggccat cactgggctc   240
caggctgagg atgaggctga ttactactgc cagtcctttg acagcagcct gagagattct   300
tgggtgttcg gcggggggac caagctgacc gtccta                             336

SEQ ID NO: 56            moltype = DNA  length = 362
FEATURE                  Location/Qualifiers
misc_feature             1..362
                         note = Synthetic
source                   1..362
                         mol_type = other DNA
                         organism = synthetic construct
SEQUENCE: 56
gaggtgcagc tggtggagtc tgggggaggc ttggtaaaac ctggggggtc ccttagactc    60
tcctgtgcag cctctggatt cactttcagt aacgcctgga tgaactgggt ccgccaggct   120
ccagggaagg ggctggagtg ggttggccgt attaagagca aaactgatgg tgggggctgca   180
gactacgctg cacccgtgaa gggcagattc accatctcaa gagatgattc aaaaaacacg   240
ctgtatctgc aaatgaacag cctgaaaacc gaggacacag ccgtgtattt ctgtaccaca   300
gtctacagat acaactatga ttccgtctgg ggccaggaa ccctggtcac cgtctcctca   360
gc                                                                   362

SEQ ID NO: 57            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 57
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcattta cagggccac tggcatccca   180
gacaggttca gtggcagtgg gtctgggaca gacttcactc tcaccatcag cagactggag   240
cctgaagatt ttgcagtgta ttactgtcag ctgtatggta gctcaccgtg gacgttcggc   300
caagggacca aggtggaaat caaa                                           324

SEQ ID NO: 58            moltype = DNA  length = 377
FEATURE                  Location/Qualifiers
misc_feature             1..377
                         note = Synthetic
source                   1..377
                         mol_type = other DNA
                         organism = synthetic construct
SEQUENCE: 58
gaggtgcagc tgttggagtc tgggggaggc ttggtacagc ctgggggg tc cctgagactc    60
tcctgtgcag cctctggatt caccttagc acctatggca tgagctgggt ccgccaggct   120
ccagggaagg ggctggagtg ggtctcaggt attagtggta gtggtggtat cacatactac   180
gcagactccg tgaggggccg gttcaccatc tccagagaca attccaagaa cacgctgtat   240
ctgcgaatga acagcctgag agccgaggac acggccgtat attactgtgc gaaagtgggg   300
gagtattacg atttttggag tggttattcc cctttgaat actggggcca gggaaccctg   360
gtcaccgtct cctcagc                                                   377

SEQ ID NO: 59            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 59
gacatccaga tgacccagtc tccttccacc ctgtctgcat ctgtaggaga cagagtcacc    60
atcacttgcc gggccagtca gaggattaat aatttggtgg cctggtatca gcagaaacca   120
gggaaagccc ctaaggtcat gatctatgat gcctccagtt tgaaaagtgg ggtcccatca   180
aggttcagcg gcagtggatc tgggacagaa ttcactctca ccatcagcag cctgcaacct   240
gatgattttg caacttattt ctgccaacag tatgatactg attcggggtg gacgttcggc   300
caagggacca aggtggaaat caaa                                           324

SEQ ID NO: 60            moltype = DNA  length = 389
FEATURE                  Location/Qualifiers
misc_feature             1..389
                         note = Synthetic
source                   1..389
                         mol_type = other DNA
                         organism = synthetic construct
SEQUENCE: 60
gaggtgcagc tgttggagtc tgggggaggc ttggtacagc cggggggg tc cctgagactc    60
```

```
tcctgtgccg cctctggatt cacctttagc aaatatgcca tgatctgggt ccgccaggcc    120
ccagggaagg ggctgcagtg ggtcgcaggt attaataaga gtggtggcag gacatactac    180
gcagactccg tgaggggccg gttcaccatc tccagagaca attccaagaa tacgctgtac    240
ctgcaaatga aaagcctgag agccgacgac acggccatgt attactgtgc gaaagaggga    300
tccccttta cagatgtttt actggtagca gctccatttg ggtggttcga tccctggggc    360
cagggaaccc tggtcaccgt ctcctcagc                                      389

SEQ ID NO: 61          moltype = AA  length = 16
FEATURE                Location/Qualifiers
REGION                 1..16
                       note = Synthetic
REGION                 1..16
                       note = X - X is any amino acid
source                 1..16
                       mol_type = protein
                       organism = synthetic construct
SEQUENCE: 61
YXXLXXXXXX XXYXXL                                                    16

SEQ ID NO: 62          moltype = AA  length = 150
FEATURE                Location/Qualifiers
REGION                 1..150
                       note = Synthetic
source                 1..150
                       mol_type = protein
                       organism = synthetic construct
SEQUENCE: 62
AQLPITEAQS FGLLDPKLCY LLDGILFIYG VILTALFLRV KFSRSADAPA YQQGQNQLYN    60
ELNLGRREEY DVLDKRRGRD PEMGGKPRRK NPQEGLYNEL QKDKMAEAYS EIGMKGERRR    120
GKGHDGLYQG LSTATKDTYD ALHMQALPPR                                     150

SEQ ID NO: 63          moltype = AA  length = 151
FEATURE                Location/Qualifiers
REGION                 1..151
                       note = Synthetic
source                 1..151
                       mol_type = protein
                       organism = synthetic construct
SEQUENCE: 63
AQLPITEAQS FGLLDPKLCY LLDGILFIYG VILTALFLRV KFSRSADAPA YQQGQNQLYN    60
ELNLGRREEY DVLDKRRGRD PEMGGKPQRR KNPQEGLYNE LQKDKMAEAY SEIGMKGERR    120
RGKGHDGLYQ GLSTATKDTY DALHMQALPP R                                   151

SEQ ID NO: 64          moltype = AA  length = 150
FEATURE                Location/Qualifiers
REGION                 1..150
                       note = Synthetic
source                 1..150
                       mol_type = protein
                       organism = synthetic construct
SEQUENCE: 64
AQLPITEAQS FGLLDPKLCY LLDGILFIYG VILTALFLRV KFSRSAEPPA YQQGQNQLYN    60
ELNLGRREEY DVLDKRRGRD PEMGGKPRRK NPQEGLYNEL QKDKMAEAYS EIGMKGERRR    120
GKGHDGLYQG LSTATKDTYD ALHMQALPPR                                     150

SEQ ID NO: 65          moltype = AA  length = 62
FEATURE                Location/Qualifiers
REGION                 1..62
                       note = Synthetic
source                 1..62
                       mol_type = protein
                       organism = synthetic construct
SEQUENCE: 65
EPQLCYILDA ILFLYGIVLT LLYCRLKIQV RKAAITSYEK SDGVYTGLST RNQETYETLK    60
HE                                                                    62

SEQ ID NO: 66          moltype = AA  length = 330
FEATURE                Location/Qualifiers
REGION                 1..330
                       note = Synthetic
source                 1..330
                       mol_type = protein
                       organism = synthetic construct
SEQUENCE: 66
RSTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
```

```
QQGNVFSCSV MHEALHNHYT QKSLSLSPGK                                          330

SEQ ID NO: 67            moltype = AA   length = 330
FEATURE                  Location/Qualifiers
REGION                   1..330
                         note = Synthetic
source                   1..330
                         mol_type = protein
                         organism = synthetic construct
SEQUENCE: 67
RSTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKKVEP KSCDKTHTCP PCPAPELLGG         120
PSVFLFPPKP KDTLMISRTP EVTCVVVDVS HEDPEVKFNW YVDGVEVHNA KTKPREEQYA         180
STYRVVSVLT VLHQDWLNGK EYKCKVSNKA LPAPIEKTIS KAKGQPREPQ VYTLPPSRDE         240
LTKNQVSLTC LVKGFYPSDI AVEWESNGQP ENNYKTTPPV LDSDGSFFLY SKLTVDKSRW         300
QQGNVFSCSV MHEALHNHYT QKSLSLSPGK                                          330

SEQ ID NO: 68            moltype = AA   length = 330
FEATURE                  Location/Qualifiers
REGION                   1..330
                         note = Synthetic
source                   1..330
                         mol_type = protein
                         organism = synthetic construct
SEQUENCE: 68
RSTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKKVEP KSCDKTHTCP PCPAPELLGG         120
PSVFLFPPKP KDTLYITREP EVTCVVVDVS HEDPEVKFNW YVDGVEVHNA KTKPREEQYN         180
STYRVVSVLT VLHQDWLNGK EYKCKVSNKA LPAPIEKTIS KAKGQPREPQ VYTLPPSRDE         240
LTKNQVSLTC LVKGFYPSDI AVEWESNGQP ENNYKTTPPV LDSDGSFFLY SKLTVDKSRW         300
QQGNVFSCSV MHEALHNHYT QKSLSLSPGK                                          330

SEQ ID NO: 69            moltype = AA   length = 108
FEATURE                  Location/Qualifiers
REGION                   1..108
                         note = Synthetic
source                   1..108
                         mol_type = protein
                         organism = synthetic construct
SEQUENCE: 69
EIVLTQSPGT LSLSPGERAT LSCRASQSVS SSYLAWYQQK PGQAPRLLIY GAFNRATGIP          60
DRFSGSGSGT DFTLTISRLE PEDFAVYYCQ QYGRSPFTFG PGTKVDIK                     108

SEQ ID NO: 70            moltype = AA   length = 7
FEATURE                  Location/Qualifiers
REGION                   1..7
                         note = Synthetic
source                   1..7
                         mol_type = protein
                         organism = synthetic construct
SEQUENCE: 70
QSVSSSY                                                                    7

SEQ ID NO: 71            moltype = AA   length = 7
FEATURE                  Location/Qualifiers
REGION                   1..7
                         note = Synthetic
source                   1..7
                         mol_type = protein
                         organism = synthetic construct
SEQUENCE: 71
GAFNRAT                                                                    7

SEQ ID NO: 72            moltype = AA   length = 9
FEATURE                  Location/Qualifiers
REGION                   1..9
                         note = Synthetic
source                   1..9
                         mol_type = protein
                         organism = synthetic construct
SEQUENCE: 72
QQYGRSPFT                                                                  9

SEQ ID NO: 73            moltype = AA   length = 125
FEATURE                  Location/Qualifiers
REGION                   1..125
                         note = Synthetic
source                   1..125
                         mol_type = protein
```

```
                        organism = synthetic construct
SEQUENCE: 73
EVQLVESGGG LVQPGGSLRL SCAASGFAFS TYAMSWVRQA PGKGLEWVSA ITGSGYSTYY    60
ADSVKGRFTI SGDNSKNTLY LQMNSLRAED TALYYCAKVG EYYDFWSGYS PFDSWGQGTL   120
VTVSS                                                              125

SEQ ID NO: 74           moltype = AA   length = 8
FEATURE                 Location/Qualifiers
REGION                  1..8
                        note = Synthetic
source                  1..8
                        mol_type = protein
                        organism = synthetic construct
SEQUENCE: 74
GFAFSTYA                                                             8

SEQ ID NO: 75           moltype = AA   length = 8
FEATURE                 Location/Qualifiers
REGION                  1..8
                        note = Synthetic
source                  1..8
                        mol_type = protein
                        organism = synthetic construct
SEQUENCE: 75
ITGSGYST                                                             8

SEQ ID NO: 76           moltype = AA   length = 18
FEATURE                 Location/Qualifiers
REGION                  1..18
                        note = Synthetic
source                  1..18
                        mol_type = protein
                        organism = synthetic construct
SEQUENCE: 76
AKVGEYYDFW SGYSPFDS                                                 18

SEQ ID NO: 77           moltype = AA   length = 112
FEATURE                 Location/Qualifiers
REGION                  1..112
                        note = Synthetic
source                  1..112
                        mol_type = protein
                        organism = synthetic construct
SEQUENCE: 77
DIVMTQTPLS SAVTLGQPAS ISCRSSQRLV HSDGNTYLSW LHQRPGQPPR LLIYKVSLRF    60
SGVPDRFSGS GAGTDFTLKI SRVEAEDVGI YYCMQATQFP LTFGGGTKVE IK           112

SEQ ID NO: 78           moltype = AA   length = 11
FEATURE                 Location/Qualifiers
REGION                  1..11
                        note = Synthetic
source                  1..11
                        mol_type = protein
                        organism = synthetic construct
SEQUENCE: 78
QRLVHSDGNT Y                                                        11

SEQ ID NO: 79           moltype = AA   length = 7
FEATURE                 Location/Qualifiers
REGION                  1..7
                        note = Synthetic
source                  1..7
                        mol_type = protein
                        organism = synthetic construct
SEQUENCE: 79
KVSLRFS                                                              7

SEQ ID NO: 80           moltype = AA   length = 9
FEATURE                 Location/Qualifiers
REGION                  1..9
                        note = Synthetic
source                  1..9
                        mol_type = protein
                        organism = synthetic construct
SEQUENCE: 80
MQATQFPLT                                                            9

SEQ ID NO: 81           moltype = AA   length = 115
FEATURE                 Location/Qualifiers
```

```
REGION                  1..115
                        note = Synthetic
source                  1..115
                        mol_type = protein
                        organism = synthetic construct
SEQUENCE: 81
EVQLLESGGG LVKPGGSLRL SCAASGFTFN EYMMNWVRQP PGKGLEWVSS ISGTSTYINY   60
ADSVKGRFTI SRDNAKNSLY LQMNSLRSDD TAMYYCARGS TGGYWGQGTL ITVSS       115

SEQ ID NO: 82           moltype = AA   length = 8
FEATURE                 Location/Qualifiers
REGION                  1..8
                        note = Synthetic
source                  1..8
                        mol_type = protein
                        organism = synthetic construct
SEQUENCE: 82
GFTFNEYM                                                             8

SEQ ID NO: 83           moltype = AA   length = 8
FEATURE                 Location/Qualifiers
REGION                  1..8
                        note = Synthetic
source                  1..8
                        mol_type = protein
                        organism = synthetic construct
SEQUENCE: 83
ISGTSTYI                                                             8

SEQ ID NO: 84           moltype = AA   length = 6
FEATURE                 Location/Qualifiers
REGION                  1..6
                        note = Synthetic
source                  1..6
                        mol_type = protein
                        organism = synthetic construct
SEQUENCE: 84
GSTGGY                                                               6

SEQ ID NO: 85           moltype = AA   length = 107
FEATURE                 Location/Qualifiers
REGION                  1..107
                        note = Synthetic
source                  1..107
                        mol_type = protein
                        organism = synthetic construct
SEQUENCE: 85
DIQMTQSPSS LSASVGDRVT ITCRASQSIS SYLNWYQQKP GKAPKVLIYS AFSLQNGVPS   60
RFSGSGSGTD FTLTISSLQP EDFATYYCQQ SYSTPRTFGQ GTKVEIK                107

SEQ ID NO: 86           moltype = AA   length = 8
FEATURE                 Location/Qualifiers
REGION                  1..8
                        note = Synthetic
source                  1..8
                        mol_type = protein
                        organism = synthetic construct
SEQUENCE: 86
QSISSYLN                                                             8

SEQ ID NO: 87           moltype = AA   length = 7
FEATURE                 Location/Qualifiers
REGION                  1..7
                        note = Synthetic
source                  1..7
                        mol_type = protein
                        organism = synthetic construct
SEQUENCE: 87
SAFSLQN                                                              7

SEQ ID NO: 88           moltype = AA   length = 9
FEATURE                 Location/Qualifiers
REGION                  1..9
                        note = Synthetic
source                  1..9
                        mol_type = protein
                        organism = synthetic construct
SEQUENCE: 88
QQSYSTPRT                                                            9
```

```
SEQ ID NO: 89          moltype = AA   length = 116
FEATURE                Location/Qualifiers
REGION                 1..116
                       note = Synthetic
source                 1..116
                       mol_type = protein
                       organism = synthetic construct
SEQUENCE: 89
QVQLQESGPG LVKPSGTLSL TCAVSGGSIS STNWWSWVRQ PPGKGLEWIG EIYHSGSTNY    60
NPSLKSRVTI SLDKSKDQFS LKLSSVTAAD TAVYYCAYSN TWTGGWGQGT LVTVSS       116

SEQ ID NO: 90          moltype = AA   length = 10
FEATURE                Location/Qualifiers
REGION                 1..10
                       note = Synthetic
source                 1..10
                       mol_type = protein
                       organism = synthetic construct
SEQUENCE: 90
GSISSTNWWS                                                           10

SEQ ID NO: 91          moltype = AA   length = 6
FEATURE                Location/Qualifiers
REGION                 1..6
                       note = Synthetic
source                 1..6
                       mol_type = protein
                       organism = synthetic construct
SEQUENCE: 91
HSGSTN                                                                6

SEQ ID NO: 92          moltype = AA   length = 7
FEATURE                Location/Qualifiers
REGION                 1..7
                       note = Synthetic
source                 1..7
                       mol_type = protein
                       organism = synthetic construct
SEQUENCE: 92
SNTWTGG                                                               7

SEQ ID NO: 93          moltype = AA   length = 107
FEATURE                Location/Qualifiers
REGION                 1..107
                       note = Synthetic
source                 1..107
                       mol_type = protein
                       organism = synthetic construct
SEQUENCE: 93
EVVLTQSPVT LSLSPGERAT LSCRASQSVS GYLAWYQQKP GQVPRLLIYD TSNRATGIPA    60
RFSGSGSGTD FTLTISTIEP EDFAVYYCQQ RSKWGVTFGG GTKVDIK                 107

SEQ ID NO: 94          moltype = AA   length = 8
FEATURE                Location/Qualifiers
REGION                 1..8
                       note = Synthetic
source                 1..8
                       mol_type = protein
                       organism = synthetic construct
SEQUENCE: 94
QSVSGYLA                                                              8

SEQ ID NO: 95          moltype = AA   length = 7
FEATURE                Location/Qualifiers
REGION                 1..7
                       note = Synthetic
source                 1..7
                       mol_type = protein
                       organism = synthetic construct
SEQUENCE: 95
DTSNRAT                                                               7

SEQ ID NO: 96          moltype = AA   length = 9
FEATURE                Location/Qualifiers
REGION                 1..9
                       note = Synthetic
source                 1..9
                       mol_type = protein
```

```
                        organism = synthetic construct
SEQUENCE: 96
QQRSKWGVT                                                                         9

SEQ ID NO: 97           moltype = AA  length = 124
FEATURE                 Location/Qualifiers
REGION                  1..124
                        note = Synthetic
source                  1..124
                        mol_type = protein
                        organism = synthetic construct
SEQUENCE: 97
QVQLVQSGAE VKKPGASVNL SCKGSGYSFR TYYIHWVRQA PGQGLEWMGI INSSGGGTTY                 60
AQKFQGRVTM TRDTSTSTVY MELRSLKYED TAMYYCARDR FPTVSGEPFA MDVWGQGTTV                120
TVSS                                                                            124

SEQ ID NO: 98           moltype = AA  length = 10
FEATURE                 Location/Qualifiers
REGION                  1..10
                        note = Synthetic
source                  1..10
                        mol_type = protein
                        organism = synthetic construct
SEQUENCE: 98
GYSFRTYYIH                                                                       10

SEQ ID NO: 99           moltype = AA  length = 10
FEATURE                 Location/Qualifiers
REGION                  1..10
                        note = Synthetic
source                  1..10
                        mol_type = protein
                        organism = synthetic construct
SEQUENCE: 99
INSSGGGTTY                                                                       10

SEQ ID NO: 100          moltype = AA  length = 15
FEATURE                 Location/Qualifiers
REGION                  1..15
                        note = Synthetic
source                  1..15
                        mol_type = protein
                        organism = synthetic construct
SEQUENCE: 100
DRFPTVSGEP FAMDV                                                                 15

SEQ ID NO: 101          moltype = AA  length = 109
FEATURE                 Location/Qualifiers
REGION                  1..109
                        note = Synthetic
source                  1..109
                        mol_type = protein
                        organism = synthetic construct
SEQUENCE: 101
EIVLTQSPGT LSLSPGERAT LSCRASQSVT SNYLAWYQQK PGQAPRVLIY GASSRATGIP                 60
DRFSGSGSGT DFTLTISRLE PEDFAVYYCQ QFGASPPYSF GQGTKVEIK                            109

SEQ ID NO: 102          moltype = AA  length = 9
FEATURE                 Location/Qualifiers
REGION                  1..9
                        note = Synthetic
source                  1..9
                        mol_type = protein
                        organism = synthetic construct
SEQUENCE: 102
QSVTSNYLA                                                                         9

SEQ ID NO: 103          moltype = AA  length = 7
FEATURE                 Location/Qualifiers
REGION                  1..7
                        note = Synthetic
source                  1..7
                        mol_type = protein
                        organism = synthetic construct
SEQUENCE: 103
GASSRAT                                                                           7

SEQ ID NO: 104          moltype = AA  length = 10
FEATURE                 Location/Qualifiers
```

```
REGION                      1..10
                            note = Synthetic
source                      1..10
                            mol_type = protein
                            organism = synthetic construct
SEQUENCE: 104
QQFGASPPYS                                                                  10

SEQ ID NO: 105              moltype = AA  length = 127
FEATURE                     Location/Qualifiers
REGION                      1..127
                            note = Synthetic
source                      1..127
                            mol_type = protein
                            organism = synthetic construct
SEQUENCE: 105
EVQLVESGGG LIQPGGSLRL SCTASGFTFS KFAMSWVRQA PGRGLEWISY ISGGSKTKYY            60
ADSVRGRFTI SRDNAKGSLF LQMNSLRAED TAIYFCAKKG WQSTFLGMDY FYGMDVWGKG           120
TTVTVSS                                                                    127

SEQ ID NO: 106              moltype = AA  length = 10
FEATURE                     Location/Qualifiers
REGION                      1..10
                            note = Synthetic
source                      1..10
                            mol_type = protein
                            organism = synthetic construct
SEQUENCE: 106
GFTFSKFAMS                                                                  10

SEQ ID NO: 107              moltype = AA  length = 9
FEATURE                     Location/Qualifiers
REGION                      1..9
                            note = Synthetic
source                      1..9
                            mol_type = protein
                            organism = synthetic construct
SEQUENCE: 107
ISGGSKTKY                                                                    9

SEQ ID NO: 108              moltype = AA  length = 20
FEATURE                     Location/Qualifiers
REGION                      1..20
                            note = Synthetic
source                      1..20
                            mol_type = protein
                            organism = synthetic construct
SEQUENCE: 108
AKKGWQSTFL GMDYFYGMDV                                                       20

SEQ ID NO: 109              moltype = AA  length = 113
FEATURE                     Location/Qualifiers
REGION                      1..113
                            note = Synthetic
source                      1..113
                            mol_type = protein
                            organism = synthetic construct
SEQUENCE: 109
DIVMTQSPDS LAVSLGERAS INCKSSQSVL SSSNTKNYLA WYQHKPGQPP KLLIYWASTR           60
ESGVPDRFSG SGSGTDFTLT ISSLQPEDVA VYYCQQYYGA PYTFGQGTKV EIK                 113

SEQ ID NO: 110              moltype = AA  length = 12
FEATURE                     Location/Qualifiers
REGION                      1..12
                            note = Synthetic
source                      1..12
                            mol_type = protein
                            organism = synthetic construct
SEQUENCE: 110
QSVLSSSNTK NY                                                               12

SEQ ID NO: 111              moltype = AA  length = 7
FEATURE                     Location/Qualifiers
REGION                      1..7
                            note = Synthetic
source                      1..7
                            mol_type = protein
                            organism = synthetic construct
SEQUENCE: 111
```

```
WASTRES                                                                  7

SEQ ID NO: 112          moltype = AA   length = 9
FEATURE                 Location/Qualifiers
REGION                  1..9
                        note = Synthetic
source                  1..9
                        mol_type = protein
                        organism = synthetic construct
SEQUENCE: 112
QQYYGAPYT                                                                9

SEQ ID NO: 113          moltype = AA   length = 118
FEATURE                 Location/Qualifiers
REGION                  1..118
                        note = Synthetic
source                  1..118
                        mol_type = protein
                        organism = synthetic construct
SEQUENCE: 113
EVQLVESGGG LVQPGGSLRL SCAASGFTFR SYDMDWFRQS TGKGLEWVSA IGSAGDTYYT         60
DSVKGRFTIS RENGKNSLYL QMNSLRAGDT AVYYCARARF GDNVFDLWGR GTLVTVSS          118

SEQ ID NO: 114          moltype = AA   length = 9
FEATURE                 Location/Qualifiers
REGION                  1..9
                        note = Synthetic
source                  1..9
                        mol_type = protein
                        organism = synthetic construct
SEQUENCE: 114
FTFRSYDMD                                                                9

SEQ ID NO: 115          moltype = AA   length = 7
FEATURE                 Location/Qualifiers
REGION                  1..7
                        note = Synthetic
source                  1..7
                        mol_type = protein
                        organism = synthetic construct
SEQUENCE: 115
IGSAGDT                                                                  7

SEQ ID NO: 116          moltype = AA   length = 10
FEATURE                 Location/Qualifiers
REGION                  1..10
                        note = Synthetic
source                  1..10
                        mol_type = protein
                        organism = synthetic construct
SEQUENCE: 116
ARFGDNVFDL                                                               10

SEQ ID NO: 117          moltype = AA   length = 108
FEATURE                 Location/Qualifiers
REGION                  1..108
                        note = Synthetic
source                  1..108
                        mol_type = protein
                        organism = synthetic construct
SEQUENCE: 117
EIVLTQSPGT LSLSPGERAA LSCRASQSVS GNYFAWYQQK SGQAPRLLIS AASSRATGVP         60
DRFSASGSGT DFTLTISRLE PEDSAVYYCQ QYGSSPLTFG QGTKVEIK                     108

SEQ ID NO: 118          moltype = AA   length = 8
FEATURE                 Location/Qualifiers
REGION                  1..8
                        note = Synthetic
source                  1..8
                        mol_type = protein
                        organism = synthetic construct
SEQUENCE: 118
SVSGNYFA                                                                 8

SEQ ID NO: 119          moltype = AA   length = 7
FEATURE                 Location/Qualifiers
REGION                  1..7
                        note = Synthetic
source                  1..7
```

```
                        mol_type = protein
                        organism = synthetic construct
SEQUENCE: 119
AASSRAT                                                                       7

SEQ ID NO: 120          moltype = AA  length = 9
FEATURE                 Location/Qualifiers
REGION                  1..9
                        note = Synthetic
source                  1..9
                        mol_type = protein
                        organism = synthetic construct
SEQUENCE: 120
QQYGSSPLT                                                                     9

SEQ ID NO: 121          moltype = AA  length = 118
FEATURE                 Location/Qualifiers
REGION                  1..118
                        note = Synthetic
source                  1..118
                        mol_type = protein
                        organism = synthetic construct
SEQUENCE: 121
EVQLVQSGGG LAQPGGSLRL SCAASGFTFR SYDMHWVRQV TGKGLEWVSA IGTAGDTYYT            60
GSVKGRFTIS RENDKSSLYL QMSSLRGEDT AVYYCARAAF GSHYFDYWGQ GTLVTVSS             118

SEQ ID NO: 122          moltype = AA  length = 9
FEATURE                 Location/Qualifiers
REGION                  1..9
                        note = Synthetic
source                  1..9
                        mol_type = protein
                        organism = synthetic construct
SEQUENCE: 122
FTFRSYDMH                                                                     9

SEQ ID NO: 123          moltype = AA  length = 10
FEATURE                 Location/Qualifiers
REGION                  1..10
                        note = Synthetic
source                  1..10
                        mol_type = protein
                        organism = synthetic construct
SEQUENCE: 123
IGTAGDTYYT                                                                   10

SEQ ID NO: 124          moltype = AA  length = 10
FEATURE                 Location/Qualifiers
REGION                  1..10
                        note = Synthetic
source                  1..10
                        mol_type = protein
                        organism = synthetic construct
SEQUENCE: 124
AAFGSHYFDY                                                                   10

SEQ ID NO: 125          moltype = AA  length = 108
FEATURE                 Location/Qualifiers
REGION                  1..108
                        note = Synthetic
source                  1..108
                        mol_type = protein
                        organism = synthetic construct
SEQUENCE: 125
SYELTQPPSV SVSPGQTARI TCSGDALPKQ YAYWYQQKPG QAPVPVIYKD SERPSGIPER            60
FSGSSSGTTV TLTISGVQAE DEADYYCQSS DSSGTYVVFG GGTKLTVL                        108

SEQ ID NO: 126          moltype = AA  length = 6
FEATURE                 Location/Qualifiers
REGION                  1..6
                        note = Synthetic
source                  1..6
                        mol_type = protein
                        organism = synthetic construct
SEQUENCE: 126
ALPKQY                                                                        6

SEQ ID NO: 127          moltype = AA  length = 4
FEATURE                 Location/Qualifiers
```

```
REGION                  1..4
                        note = Synthetic
source                  1..4
                        mol_type = protein
                        organism = synthetic construct
SEQUENCE: 127
KDSE                                                                      4

SEQ ID NO: 128          moltype = AA   length = 11
FEATURE                 Location/Qualifiers
REGION                  1..11
                        note = Synthetic
source                  1..11
                        mol_type = protein
                        organism = synthetic construct
SEQUENCE: 128
QSSDSSGTYV V                                                             11

SEQ ID NO: 129          moltype = AA   length = 120
FEATURE                 Location/Qualifiers
REGION                  1..120
                        note = Synthetic
source                  1..120
                        mol_type = protein
                        organism = synthetic construct
SEQUENCE: 129
EVQLVQSGAE VKKPGASVKV SCKASGYTFT SYYMHWVRQA PGQGLEWMGI INPSGGSTSY         60
AQKFQGRVTM TRDTSTSTVY MELSSLRSED TAVYYCARHD SSGYDAFDIW GQGTMVTVSS        120

SEQ ID NO: 130          moltype = AA   length = 8
FEATURE                 Location/Qualifiers
REGION                  1..8
                        note = Synthetic
source                  1..8
                        mol_type = protein
                        organism = synthetic construct
SEQUENCE: 130
GYTFTSYY                                                                  8

SEQ ID NO: 131          moltype = AA   length = 8
FEATURE                 Location/Qualifiers
REGION                  1..8
                        note = Synthetic
source                  1..8
                        mol_type = protein
                        organism = synthetic construct
SEQUENCE: 131
INPSGGST                                                                  8

SEQ ID NO: 132          moltype = AA   length = 13
FEATURE                 Location/Qualifiers
REGION                  1..13
                        note = Synthetic
source                  1..13
                        mol_type = protein
                        organism = synthetic construct
SEQUENCE: 132
ARHDSSGYDA FDI                                                           13

SEQ ID NO: 133          moltype = AA   length = 112
FEATURE                 Location/Qualifiers
REGION                  1..112
                        note = Synthetic
source                  1..112
                        mol_type = protein
                        organism = synthetic construct
SEQUENCE: 133
DIVMTQSPLS LPVTPGEPAS ISCRSSQSLL HSNGYNYVDW YLQKPGQSPQ LLIYLGSSRA         60
SGVPDRFSGS GSGTDFTLKI SRVETEDVGI YYCMQGLQTP LTFGGGTKVE IK                112

SEQ ID NO: 134          moltype = AA   length = 11
FEATURE                 Location/Qualifiers
REGION                  1..11
                        note = Synthetic
source                  1..11
                        mol_type = protein
                        organism = synthetic construct
SEQUENCE: 134
QSLLHSNGYN Y                                                             11
```

```
SEQ ID NO: 135           moltype = AA  length = 4
FEATURE                  Location/Qualifiers
REGION                   1..4
                         note = Synthetic
source                   1..4
                         mol_type = protein
                         organism = synthetic construct
SEQUENCE: 135
LGSS                                                                      4

SEQ ID NO: 136           moltype = AA  length = 9
FEATURE                  Location/Qualifiers
REGION                   1..9
                         note = Synthetic
source                   1..9
                         mol_type = protein
                         organism = synthetic construct
SEQUENCE: 136
MQGLQTPLT                                                                 9

SEQ ID NO: 137           moltype = AA  length = 121
FEATURE                  Location/Qualifiers
REGION                   1..121
                         note = Synthetic
source                   1..121
                         mol_type = protein
                         organism = synthetic construct
SEQUENCE: 137
QVQLVQSGAE VKKPGASVKV SCRTSGYTFS SYNIHWVRQA PGQGLEWMGV INPYGRSTTL         60
YARRFRDRVT MTRDTSTSTV YMELSSLRSE DTAVYFCGRL YSGAPYGLDV WGQGSTVTVS         120
S                                                                        121

SEQ ID NO: 138           moltype = AA  length = 10
FEATURE                  Location/Qualifiers
REGION                   1..10
                         note = Synthetic
source                   1..10
                         mol_type = protein
                         organism = synthetic construct
SEQUENCE: 138
GYTFSSYNIH                                                                10

SEQ ID NO: 139           moltype = AA  length = 7
FEATURE                  Location/Qualifiers
REGION                   1..7
                         note = Synthetic
source                   1..7
                         mol_type = protein
                         organism = synthetic construct
SEQUENCE: 139
PYGRSTT                                                                   7

SEQ ID NO: 140           moltype = AA  length = 13
FEATURE                  Location/Qualifiers
REGION                   1..13
                         note = Synthetic
source                   1..13
                         mol_type = protein
                         organism = synthetic construct
SEQUENCE: 140
GRLYSGAPYG LDV                                                            13

SEQ ID NO: 141           moltype = AA  length = 113
FEATURE                  Location/Qualifiers
REGION                   1..113
                         note = Synthetic
source                   1..113
                         mol_type = protein
                         organism = synthetic construct
SEQUENCE: 141
DIVLTQSPDS LAASLGERAT ISCKSSHSVL YSSNNKDFFA WYQQKPGQPP KLLISWASTR         60
ESGVPVRFNG GGSGTHFTLT ISSLQAEDVA VYYCQQYFSS PITFGQGTRL EIK                113

SEQ ID NO: 142           moltype = AA  length = 12
FEATURE                  Location/Qualifiers
REGION                   1..12
                         note = Synthetic
source                   1..12
```

```
                        mol_type = protein
                        organism = synthetic construct
SEQUENCE: 142
HSVLYSSNNK DF                                                     12

SEQ ID NO: 143          moltype = AA   length = 4
FEATURE                 Location/Qualifiers
REGION                  1..4
                        note = Synthetic
source                  1..4
                        mol_type = protein
                        organism = synthetic construct
SEQUENCE: 143
WAST                                                              4

SEQ ID NO: 144          moltype = AA   length = 9
FEATURE                 Location/Qualifiers
REGION                  1..9
                        note = Synthetic
source                  1..9
                        mol_type = protein
                        organism = synthetic construct
SEQUENCE: 144
QQYFSSPIT                                                         9

SEQ ID NO: 145          moltype = AA   length = 124
FEATURE                 Location/Qualifiers
REGION                  1..124
                        note = Synthetic
source                  1..124
                        mol_type = protein
                        organism = synthetic construct
SEQUENCE: 145
QVQLVQSGAE VKKPGSSVKV ACKVSGGTFS SYTISWVRQA PGQGLEWMGG IIPSFGVGHY  60
SQKFRDRVTL TADKSTTTAF LELSSVRSED TALYYCAILG TFNWKSGGNY FGPWGQGTLV 120
TVSS                                                             124

SEQ ID NO: 146          moltype = AA   length = 8
FEATURE                 Location/Qualifiers
REGION                  1..8
                        note = Synthetic
source                  1..8
                        mol_type = protein
                        organism = synthetic construct
SEQUENCE: 146
GGTFSSYT                                                          8

SEQ ID NO: 147          moltype = AA   length = 8
FEATURE                 Location/Qualifiers
REGION                  1..8
                        note = Synthetic
source                  1..8
                        mol_type = protein
                        organism = synthetic construct
SEQUENCE: 147
IIPSFGVG                                                          8

SEQ ID NO: 148          moltype = AA   length = 17
FEATURE                 Location/Qualifiers
REGION                  1..17
                        note = Synthetic
source                  1..17
                        mol_type = protein
                        organism = synthetic construct
SEQUENCE: 148
AILGTFNWKS GGNYFGP                                                17

SEQ ID NO: 149          moltype = AA   length = 107
FEATURE                 Location/Qualifiers
REGION                  1..107
                        note = Synthetic
source                  1..107
                        mol_type = protein
                        organism = synthetic construct
SEQUENCE: 149
EIVLTQSPNT LSLSPGERAT LSCRASQSLR TNQLAWYQQK PGQAPRLLIH TSTRATGIPD  60
RFSGSGSGTD FTLTISGLEA EDFAVYYCQA SDTSSLTFGG GTKLEIR              107

SEQ ID NO: 150          moltype = AA   length = 6
```

```
FEATURE                 Location/Qualifiers
REGION                  1..6
                        note = Synthetic
source                  1..6
                        mol_type = protein
                        organism = synthetic construct
SEQUENCE: 150
QSLRTN                                                                    6

SEQ ID NO: 151          moltype = AA   length = 4
FEATURE                 Location/Qualifiers
REGION                  1..4
                        note = Synthetic
source                  1..4
                        mol_type = protein
                        organism = synthetic construct
SEQUENCE: 151
HTST                                                                      4

SEQ ID NO: 152          moltype = AA   length = 9
FEATURE                 Location/Qualifiers
REGION                  1..9
                        note = Synthetic
source                  1..9
                        mol_type = protein
                        organism = synthetic construct
SEQUENCE: 152
QASDTSSLT                                                                 9

SEQ ID NO: 153          moltype = AA   length = 125
FEATURE                 Location/Qualifiers
REGION                  1..125
                        note = Synthetic
source                  1..125
                        mol_type = protein
                        organism = synthetic construct
SEQUENCE: 153
QVQLQESGPG LVKPSESLSL TCTISGGSIR DYYWSWIRQA PGKGLEWIGY KYHAARGNSN         60
PSLESRVTMS IDTSRSEFSL RLTSVTAADT AVYYCARVQY GPGGGYYSGN WLDLWGQGTL        120
VTVSS                                                                   125

SEQ ID NO: 154          moltype = AA   length = 8
FEATURE                 Location/Qualifiers
REGION                  1..8
                        note = Synthetic
source                  1..8
                        mol_type = protein
                        organism = synthetic construct
SEQUENCE: 154
GGSIRDYY                                                                  8

SEQ ID NO: 155          moltype = AA   length = 7
FEATURE                 Location/Qualifiers
REGION                  1..7
                        note = Synthetic
source                  1..7
                        mol_type = protein
                        organism = synthetic construct
SEQUENCE: 155
KYHAARG                                                                   7

SEQ ID NO: 156          moltype = AA   length = 19
FEATURE                 Location/Qualifiers
REGION                  1..19
                        note = Synthetic
source                  1..19
                        mol_type = protein
                        organism = synthetic construct
SEQUENCE: 156
ARVQYGPGGG YYSGNWLDL                                                     19

SEQ ID NO: 157          moltype = AA   length = 106
FEATURE                 Location/Qualifiers
REGION                  1..106
                        note = Synthetic
source                  1..106
                        mol_type = protein
                        organism = synthetic construct
SEQUENCE: 157
```

```
EIVMTQSPAT LSLSPGERAS LSCRASQSIA TNLAWYQQKP GQPPRVLIYG ASTRATGIPT    60
RFSGSGSGTE FTLTISSLQS EDFAIYYCHQ YHSWRTFGQG TKVEMK                 106

SEQ ID NO: 158          moltype = AA  length = 6
FEATURE                 Location/Qualifiers
REGION                  1..6
                        note = Synthetic
source                  1..6
                        mol_type = protein
                        organism = synthetic construct
SEQUENCE: 158
QSIATN                                                               6

SEQ ID NO: 159          moltype = AA  length = 4
FEATURE                 Location/Qualifiers
REGION                  1..4
                        note = Synthetic
source                  1..4
                        mol_type = protein
                        organism = synthetic construct
SEQUENCE: 159
GAST                                                                 4

SEQ ID NO: 160          moltype = AA  length = 8
FEATURE                 Location/Qualifiers
REGION                  1..8
                        note = Synthetic
source                  1..8
                        mol_type = protein
                        organism = synthetic construct
SEQUENCE: 160
HQYHSWRT                                                             8

SEQ ID NO: 161          moltype = AA  length = 122
FEATURE                 Location/Qualifiers
REGION                  1..122
                        note = Synthetic
source                  1..122
                        mol_type = protein
                        organism = synthetic construct
SEQUENCE: 161
QLQLQESGPG LVKPSETLSL TCTVSGGSVA SSNDYWGWIR QPPGKGPEWI GTIFYRGTTD    60
YNPSLKSRLT MSVDTSRNQF SLKLSSVTAA DTAVYYCARL PLWFSELGHD YWGQGTLVTV   120
SS                                                                 122

SEQ ID NO: 162          moltype = AA  length = 10
FEATURE                 Location/Qualifiers
REGION                  1..10
                        note = Synthetic
source                  1..10
                        mol_type = protein
                        organism = synthetic construct
SEQUENCE: 162
GGSVASSNDY                                                          10

SEQ ID NO: 163          moltype = AA  length = 7
FEATURE                 Location/Qualifiers
REGION                  1..7
                        note = Synthetic
source                  1..7
                        mol_type = protein
                        organism = synthetic construct
SEQUENCE: 163
IFYRGTT                                                              7

SEQ ID NO: 164          moltype = AA  length = 14
FEATURE                 Location/Qualifiers
REGION                  1..14
                        note = Synthetic
source                  1..14
                        mol_type = protein
                        organism = synthetic construct
SEQUENCE: 164
ARLPLWFSEL GHDY                                                     14

SEQ ID NO: 165          moltype = AA  length = 111
FEATURE                 Location/Qualifiers
REGION                  1..111
                        note = Synthetic
```

```
source                  1..111
                        mol_type = protein
                        organism = synthetic construct
SEQUENCE: 165
QSALTQPPSA SGSPGQSVTI SCTGTSSDVG VYNSVSWYRQ HPGKVPKLMI YEVSKRPSGV    60
PDRFSGSKSG NTASLTVSGL QADDEGDYYC CSCSGTNSLC VFGTGTKVTV L            111

SEQ ID NO: 166          moltype = AA   length = 9
FEATURE                 Location/Qualifiers
REGION                  1..9
                        note = Synthetic
source                  1..9
                        mol_type = protein
                        organism = synthetic construct
SEQUENCE: 166
SSDVGVYNS                                                              9

SEQ ID NO: 167          moltype = AA   length = 4
FEATURE                 Location/Qualifiers
REGION                  1..4
                        note = Synthetic
source                  1..4
                        mol_type = protein
                        organism = synthetic construct
SEQUENCE: 167
EVSK                                                                   4

SEQ ID NO: 168          moltype = AA   length = 11
FEATURE                 Location/Qualifiers
REGION                  1..11
                        note = Synthetic
source                  1..11
                        mol_type = protein
                        organism = synthetic construct
SEQUENCE: 168
CSCSGTNSLC V                                                          11

SEQ ID NO: 169          moltype = AA   length = 124
FEATURE                 Location/Qualifiers
REGION                  1..124
                        note = Synthetic
source                  1..124
                        mol_type = protein
                        organism = synthetic construct
SEQUENCE: 169
QVQLHESGPG LVQPSETLSL TCTVSGDSIT NYYWSWIRQP PGKGLEWIGY MYYSASAHYN    60
PSLQSRVTIS VDTSKNQFSL KLSSVTAADT AVYFCARVDY SSSSYYSGNW FDPWGQGTLV   120
TVSS                                                                 124

SEQ ID NO: 170          moltype = AA   length = 8
FEATURE                 Location/Qualifiers
REGION                  1..8
                        note = Synthetic
source                  1..8
                        mol_type = protein
                        organism = synthetic construct
SEQUENCE: 170
GDSITNYY                                                               8

SEQ ID NO: 171          moltype = AA   length = 7
FEATURE                 Location/Qualifiers
REGION                  1..7
                        note = Synthetic
source                  1..7
                        mol_type = protein
                        organism = synthetic construct
SEQUENCE: 171
MYYSASA                                                                7

SEQ ID NO: 172          moltype = AA   length = 18
FEATURE                 Location/Qualifiers
REGION                  1..18
                        note = Synthetic
source                  1..18
                        mol_type = protein
                        organism = synthetic construct
SEQUENCE: 172
ARVDYSSSSY YSGNWFDP                                                   18
```

```
SEQ ID NO: 173            moltype = AA  length = 112
FEATURE                   Location/Qualifiers
REGION                    1..112
                          note = Synthetic
source                    1..112
                          mol_type = protein
                          organism = synthetic construct
SEQUENCE: 173
QSVLTQPPSV SGAPGQTVTI SCTGSYSNIG AGYDVQWYQH LPGTAPKLLI YDNVHRPSGV   60
PDRFSGSKSG TSASLAITGL QTEDEADYYC QSYDSRLRDQ WVFGGGTKLT VL          112

SEQ ID NO: 174            moltype = AA  length = 9
FEATURE                   Location/Qualifiers
REGION                    1..9
                          note = Synthetic
source                    1..9
                          mol_type = protein
                          organism = synthetic construct
SEQUENCE: 174
YSNIGAGYD                                                            9

SEQ ID NO: 175            moltype = AA  length = 4
FEATURE                   Location/Qualifiers
REGION                    1..4
                          note = Synthetic
source                    1..4
                          mol_type = protein
                          organism = synthetic construct
SEQUENCE: 175
DNVH                                                                 4

SEQ ID NO: 176            moltype = AA  length = 12
FEATURE                   Location/Qualifiers
REGION                    1..12
                          note = Synthetic
source                    1..12
                          mol_type = protein
                          organism = synthetic construct
SEQUENCE: 176
QSYDSRLRDQ WV                                                       12

SEQ ID NO: 177            moltype = AA  length = 122
FEATURE                   Location/Qualifiers
REGION                    1..122
                          note = Synthetic
source                    1..122
                          mol_type = protein
                          organism = synthetic construct
SEQUENCE: 177
EVQLVESGGD LVQPGGSLRL SCAASGITLS GVWMNWVRQA PGKGLEWIGR IKSTSDGGRA   60
DFAAPARGRF TMSRDESKNK LFLQMNNLGI EDTGMYYCFT RVQRDGTKDD FWGRGTLVTV  120
SS                                                                 122

SEQ ID NO: 178            moltype = AA  length = 8
FEATURE                   Location/Qualifiers
REGION                    1..8
                          note = Synthetic
source                    1..8
                          mol_type = protein
                          organism = synthetic construct
SEQUENCE: 178
GITLSGVW                                                             8

SEQ ID NO: 179            moltype = AA  length = 10
FEATURE                   Location/Qualifiers
REGION                    1..10
                          note = Synthetic
source                    1..10
                          mol_type = protein
                          organism = synthetic construct
SEQUENCE: 179
IKSTSDGGRA                                                          10

SEQ ID NO: 180            moltype = AA  length = 13
FEATURE                   Location/Qualifiers
REGION                    1..13
                          note = Synthetic
source                    1..13
                          mol_type = protein
```

```
                        organism = synthetic construct
SEQUENCE: 180
FTRVQRDGTK DDF                                                            13

SEQ ID NO: 181          moltype = AA  length = 107
FEATURE                 Location/Qualifiers
REGION                  1..107
                        note = Synthetic
source                  1..107
                        mol_type = protein
                        organism = synthetic construct
SEQUENCE: 181
QSALTQPASV SGSPGQSITL SCTVGGNKFV SWYQQHPGKA PKLIISDFTD RPSGVSSRFS          60
GSKSGNTASL TISGLQPDDE ATYFCSSYAS TSTSLWVFGG GTKLTVL                       107

SEQ ID NO: 182          moltype = AA  length = 8
FEATURE                 Location/Qualifiers
REGION                  1..8
                        note = Synthetic
source                  1..8
                        mol_type = protein
                        organism = synthetic construct
SEQUENCE: 182
CTVGGNKF                                                                  8

SEQ ID NO: 183          moltype = AA  length = 4
FEATURE                 Location/Qualifiers
REGION                  1..4
                        note = Synthetic
source                  1..4
                        mol_type = protein
                        organism = synthetic construct
SEQUENCE: 183
DFTD                                                                      4

SEQ ID NO: 184          moltype = AA  length = 12
FEATURE                 Location/Qualifiers
REGION                  1..12
                        note = Synthetic
source                  1..12
                        mol_type = protein
                        organism = synthetic construct
SEQUENCE: 184
SSYASTSTSL WV                                                             12

SEQ ID NO: 185          moltype = AA  length = 125
FEATURE                 Location/Qualifiers
REGION                  1..125
                        note = Synthetic
source                  1..125
                        mol_type = protein
                        organism = synthetic construct
SEQUENCE: 185
QEQLQESGPG LVKPSGTLSL TCTVSGVSVS GSYFWNWVRQ PPGKGLEWLG FIHSTGSTNT          60
NPSLKSRVTI SVDTSKNQFS LRLTSVSAAD TAVYYCARAA WLVGGEYYNY GMDLWGQGTT          120
VTVSS                                                                     125

SEQ ID NO: 186          moltype = AA  length = 9
FEATURE                 Location/Qualifiers
REGION                  1..9
                        note = Synthetic
source                  1..9
                        mol_type = protein
                        organism = synthetic construct
SEQUENCE: 186
GVSVSGSYF                                                                 9

SEQ ID NO: 187          moltype = AA  length = 7
FEATURE                 Location/Qualifiers
REGION                  1..7
                        note = Synthetic
source                  1..7
                        mol_type = protein
                        organism = synthetic construct
SEQUENCE: 187
IHSTGST                                                                   7

SEQ ID NO: 188          moltype = AA  length = 18
FEATURE                 Location/Qualifiers
```

```
REGION                  1..18
                        note = Synthetic
source                  1..18
                        mol_type = protein
                        organism = synthetic construct
SEQUENCE: 188
ARAAWLVGGE YYNYGMDL                                                    18

SEQ ID NO: 189          moltype = AA  length = 107
FEATURE                 Location/Qualifiers
REGION                  1..107
                        note = Synthetic
source                  1..107
                        mol_type = protein
                        organism = synthetic construct
SEQUENCE: 189
GIQLTQSPSF LSASVGDRVT ITCRASQGIY TYLAWYQQKP GKAPKLLVYV ASTLQSGVPS       60
RFSGSGSGTE FTLTISSLQP EDFATYYCQQ LNSYPLTFGQ GTKLEIK                    107

SEQ ID NO: 190          moltype = AA  length = 6
FEATURE                 Location/Qualifiers
REGION                  1..6
                        note = Synthetic
source                  1..6
                        mol_type = protein
                        organism = synthetic construct
SEQUENCE: 190
QGIYTY                                                                  6

SEQ ID NO: 191          moltype = AA  length = 4
FEATURE                 Location/Qualifiers
REGION                  1..4
                        note = Synthetic
source                  1..4
                        mol_type = protein
                        organism = synthetic construct
SEQUENCE: 191
VASY                                                                    4

SEQ ID NO: 192          moltype = AA  length = 9
FEATURE                 Location/Qualifiers
REGION                  1..9
                        note = Synthetic
source                  1..9
                        mol_type = protein
                        organism = synthetic construct
SEQUENCE: 192
QQLNSYPLT                                                               9

SEQ ID NO: 193          moltype = AA  length = 127
FEATURE                 Location/Qualifiers
REGION                  1..127
                        note = Synthetic
source                  1..127
                        mol_type = protein
                        organism = synthetic construct
SEQUENCE: 193
QVQLVESGGG VVQPGRSLRL SCVASGFTFS SYGMHWVRQA PGKGLEWVAF IWYDGTIQYY       60
GDSVKGRFII SRDNSRNTLY LQMNSLRAED TAVYYCASTL YRNGDYGSGS RTPDDYWGQG      120
TLVTVSS                                                               127

SEQ ID NO: 194          moltype = AA  length = 8
FEATURE                 Location/Qualifiers
REGION                  1..8
                        note = Synthetic
source                  1..8
                        mol_type = protein
                        organism = synthetic construct
SEQUENCE: 194
GFTFSSYG                                                                8

SEQ ID NO: 195          moltype = AA  length = 8
FEATURE                 Location/Qualifiers
REGION                  1..8
                        note = Synthetic
source                  1..8
                        mol_type = protein
                        organism = synthetic construct
SEQUENCE: 195
```

```
IWYDGTIQ                                                                    8

SEQ ID NO: 196           moltype = AA   length = 20
FEATURE                  Location/Qualifiers
REGION                   1..20
                         note = Synthetic
source                   1..20
                         mol_type = protein
                         organism = synthetic construct
SEQUENCE: 196
ASTLYRNGDY GSGSRTPDDY                                                      20

SEQ ID NO: 197           moltype = DNA   length = 360
FEATURE                  Location/Qualifiers
misc_feature             1..360
                         note = Synthetic
source                   1..360
                         mol_type = other DNA
                         organism = synthetic construct
SEQUENCE: 197
gaggtgcagc tggtgcagtc tggggctgag gtgaagaagc ctggggcctc agtgaaggtt            60
tcctgcaagg catctggata cacccttcacc agctactata tgcactgggt gcgacaggcc         120
cctggacaag gcttgagtg gatgggaata tcaaccctag tggtggtag cacaagctac            180
gcacagaagt tccagggcag agtcaccatg accaggaca cgtccacgag cacagtctac           240
atggagctga gcagcctgag atctgaggac acggccgtgt attactgtgc taggcatgat          300
agtagtggtt atgatgcttt tgatatctgg ggccaaggga caatggtcac cgtctcttca          360

SEQ ID NO: 198           moltype = DNA   length = 324
FEATURE                  Location/Qualifiers
misc_feature             1..324
                         note = Synthetic
source                   1..324
                         mol_type = other DNA
                         organism = synthetic construct
SEQUENCE: 198
tcctatgagc tgacacagcc accctcggtg tcagtgtccc caggacagac ggccaggatc            60
acctgctctg gagatgcatt gccaaagcaa tatgcttatt ggtaccagca gaagccaggc          120
caggcccctg tgccggtgat atataaagac agtgagaggc cctcagggat ccctgagcga          180
ttctctggct ccagctcagg gacaacagtc acgttgacca tcagtggagt ccaggcagaa          240
gacgaggctg actattactg tcaatcatca gacagcagtg gtacttatgt ggtattcggc          300
ggagggacca agctgaccgt ccta                                                 324

SEQ ID NO: 199           moltype = DNA   length = 363
FEATURE                  Location/Qualifiers
misc_feature             1..363
                         note = Synthetic
source                   1..363
                         mol_type = other DNA
                         organism = synthetic construct
SEQUENCE: 199
caggtgcaac tggtgcagtc aggggctgag gtgaagaagc ctggggcctc agtgaaggtt            60
tcctgcagga catctggata cacattctcc agctacaata tacattgggt gcgacaggcc          120
cctggacaag gtcttgagtg gatgggagtt attaatcctt atggccgtag taccacactt          180
tacgcacgga ggttccggga cagagtcacc atgaccaggg acacgtccac gagcacagtt          240
tacatggaac tgagcagcct gagatccgag gacacggccg tatactttct ggaaggctt           300
tacagtggtg cacccctatgg tttggacgtc tggggccaag ggagcacggt caccgtctct         360
tca                                                                        363

SEQ ID NO: 200           moltype = DNA   length = 336
FEATURE                  Location/Qualifiers
misc_feature             1..336
                         note = Synthetic
source                   1..336
                         mol_type = other DNA
                         organism = synthetic construct
SEQUENCE: 200
gatattgtga tgactcagtc tccactctcc ctgcccgtca cccctggaga gccggcctcc            60
atctcctgca ggtctagtca gagcctcctg catagtaatg gatacaacta tgtggattgg          120
tacctgcaga gccagggca gtctccacag ctcctgatct atttgggttc tagtcgggcc           180
tccggggtcc ctgacaggtt cagtggcagt ggatcaggca cagatttac actgaaaatc           240
agcagagtgg agactgagga tgttggcatt tattactgca tgcaaggtct acaaactccc          300
ctcactttcg gcggagggac caaggtggag atcaaa                                    336

SEQ ID NO: 201           moltype = DNA   length = 372
FEATURE                  Location/Qualifiers
misc_feature             1..372
                         note = Synthetic
source                   1..372
                         mol_type = other DNA
```

-continued

```
                        organism = synthetic construct
SEQUENCE: 201
caggtgcagc tggtgcagtc tggggctgaa gtgaagaagc ctgggtcctc ggtgaaggtc    60
gcctgcaagg tttctggagg caccttcagc agctatacta ttagttgggt gcgacaggcc   120
cctggacaag ggcttgagtg gatgggaggg atcatccctt cctttggtgt gggacactac   180
tcacagaagt tccgggacag agtcacgcta accgcggaca aatccacgac cacagccttc   240
ttggaactga gcagcgtgag atctgaagac acggccctat attactgtgc gatactgggg   300
acttttaact ggaagtccgg gggcaactac ttcggcccct ggggccaggg gaccctggtc   360
accgtctctt ca                                                      372

SEQ ID NO: 202          moltype = DNA   length = 339
FEATURE                 Location/Qualifiers
misc_feature            1..339
                        note = Synthetic
source                  1..339
                        mol_type = other DNA
                        organism = synthetic construct
SEQUENCE: 202
gacatcgtgc tgacccagtc tccagactcc ctggctgcgt ctctgggcga gagggccacc    60
atcagctgca agtccagcca cagtgtttta tacagctcca acaataagga cttctttgcc   120
tggtaccagc agaaaccagg acagcctccc aaactgctca tttcctgggc atctacccgg   180
gaatccgggg tccctgtccg attcaatggc ggcgggtctg ggacacattt cactctcacc   240
atcagcagcc tgcaggctga agatgtggca gtttactact gtcagcaata ttttagttct   300
ccgatcacct tcggccaagg gacacgactg gagattaaa                         339

SEQ ID NO: 203          moltype = DNA   length = 375
FEATURE                 Location/Qualifiers
misc_feature            1..375
                        note = Synthetic
source                  1..375
                        mol_type = other DNA
                        organism = synthetic construct
SEQUENCE: 203
caggtgcagc tgcaggagtc gggcccagga ctggtgaagc cttcggagag cctgtccctc    60
acatgcacta tctctggcgg ctccataagg gactattact ggagctggat tcggcaggcc   120
ccagggaagg gactgagtg gatcggatat aagtatcacg ctgcgcgcgg caactccaat   180
ccctccctcg agagtcgagt caccatgtcc atcgacacgt ccaggagcga gttctccctg   240
aggctgactt ctgtgaccgc tgcggacacg gccgtctatt attgtgcgag agttcaatac   300
ggtcctgggg gcggttacta ttcggggaac tggttggacc tctgggccca gggaaccctg   360
gtcaccgtct cttca                                                   375

SEQ ID NO: 204          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 204
gaaattgtgt tgacacagtc tccaaacacc ctgtctttgt ctccagggga aagagccacc    60
ctctcctgca gggccagtca gagtcttcgt accaaccagt tagcctggta ccagcaaaaa   120
cctggccagg ctcccaggct cctcatccat acatccacca gggccactgg catcccagac   180
aggttcagtg gcagtgggtc tgggacagac ttcactctca ccatcagcgg actgaggct   240
gaagactttg cagtgtatta ctgtcaggcg tctgatacct catcgctcac tttcggcgga   300
gggaccaagt tagagatcag a                                            321

SEQ ID NO: 205          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 205
cagctgcagc tgcaggagtc gggcccagga ctggtgaagc cttcggagac cctgtccctc    60
acctgcactg tctctggtgg ctccgtcgcc agtagtaatg actactgggg ctggatccgc   120
cagcccccag ggaaggggcc ggagtggatt gggactatct tttatagagg gaccaccgac   180
tacaacccgt ccctcaagag tcgactcact atgtccgtgg acacgtccag gaaccagttc   240
tccctgaagc tgagctctgt gaccgccgca gacacggctg tctattactg tgcgagactg   300
cccctatggt tcagtgagtt aggtcatgac tactggggcc agggaaccct ggtcaccgtc   360
tcctca                                                             366

SEQ ID NO: 206          moltype = DNA   length = 407
FEATURE                 Location/Qualifiers
misc_feature            1..407
                        note = Synthetic
source                  1..407
                        mol_type = other DNA
                        organism = synthetic construct
```

-continued

```
SEQUENCE: 206
gaaatagtga tgacgcagtc tccagccacc ctgtctctgt ctccaggaga aagagcctcc    60
ctgtcctgca gggccagtca gagtattgcc accaacttag cctggtacca gcaaaaacct   120
ggccagcctc ccagggtcct catctatggt gcatccacaa gggcaactgg tatcccaacc   180
aggttcagtg gcagtggatc tgggacagag ttcactctca ccatcagcag cctgcagtct   240
gaagatttg caatttatta ctgtcaccag tatcatagct ggcggacgtt cggccaaggg    300
accaaggtag aaatgaaagt gcgagagtgg actacagttc gagtagttat tattcgggaa   360
actggttcga cccctggggc cagggaaccc ttgtcaccgt ctcctca                 407

SEQ ID NO: 207          moltype = DNA   length = 372
FEATURE                 Location/Qualifiers
misc_feature            1..372
                        note = Synthetic
source                  1..372
                        mol_type = other DNA
                        organism = synthetic construct
SEQUENCE: 207
caggtgcagc tgcatgagtc gggcccaggg ctggtgcagc cttcggagac cctgtccctc    60
acctgcactg tctctggtga ctccatcact aattactact ggagctggat ccggcagccc   120
ccagggaagg gactggagtg gattggatat atgtattaca gtgcgagcgc ccactacaat   180
ccctccctcc agagtcgagt caccatttca gtggacacgt ccaagaacca gttctccctg   240
aaaactgagc tctgtgaccg ctgcggacacg gccgtgtatt tctgtgcgag agtggactac   300
agttcgagta gttattattc gggaaactgg ttcgacccct ggggccaggg aacccttgtc   360
accgtctcct ca                                                        372

SEQ ID NO: 208          moltype = DNA   length = 333
FEATURE                 Location/Qualifiers
misc_feature            1..333
                        note = Synthetic
source                  1..333
                        mol_type = other DNA
                        organism = synthetic construct
SEQUENCE: 208
cagtctgccc tgactcagcc tccctccgcg tccgggtctc ctggacagtc agtcaccatc    60
tcctgcactg gaaccagcag tgacgttggt gtttataatt ctgtctcctg gtaccgacag   120
cacccaggca aagtccccaa actcatgatt tatgaggtca gtaagcggcc ctcaggggtc   180
cctgatcgct tctctggctc caagtccggc aacacggcct ccctgaccgt ctctgggctc   240
caggctgacg atgagggtga ttattactgc tgctcatgtt caggcaccaa cagcctctgt   300
gtcttcggaa ctgggaccaa ggtcaccgtc ctg                                 333

SEQ ID NO: 209          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 209
gaggtgcagc tggtggagtc tgggggagac ttagtacagc ctgggggtc cctcagactc     60
tcctgtgcag cctctggaat caccttgagt ggagtttgga tgaactgggt ccgccaggct   120
ccagggaagg ggctggagtg gattggccgt attaaaagca caagtgacgg tgggagagca   180
gacttcgccg cacccgcgag aggcagattc accatgtcaa gagatgagtc aaagaataag   240
ctgtttctgc aaatgaacaa cctgggaatc gaagacacag gcatgtatta ttgtttcacg   300
agagtccaaa gagacggaac taaagatgac ttctggggcc ggggaaccct ggtcaccgtc   360
tcttca                                                               366

SEQ ID NO: 210          moltype = DNA   length = 336
FEATURE                 Location/Qualifiers
misc_feature            1..336
                        note = Synthetic
source                  1..336
                        mol_type = other DNA
                        organism = synthetic construct
SEQUENCE: 210
cagtctgtgc tgacgcagcc gccctcagtg tctggggccc agggcagac ggtcaccatc     60
tcctgcactg ggagctactc caacatcggg gcaggttatg atgtacagtg gtaccagcac   120
cttcctggaa cagcccccaa actcctcatt tatgataatg tccatcggcc ctcagggtc    180
cctgaccgat tctctggctc caagtctggc acctcagcct ccctggccat cactgggctc   240
cagactgaag atgaggctga ttattattgc cagtcctatg acagcagact gagggatcaa   300
tgggtgttcg gcggagggac caagctgacc gtccta                              336

SEQ ID NO: 211          moltype = DNA   length = 375
FEATURE                 Location/Qualifiers
misc_feature            1..375
                        note = Synthetic
source                  1..375
                        mol_type = other DNA
                        organism = synthetic construct
SEQUENCE: 211
```

```
caggagcagc tgcaagagtc gggcccagga ctggtgaagc cttcggggac cctgtccctc    60
acctgcactg tctccggcgt ctccgtcagt gggagttact tctggaattg ggtccgccag   120
cccccaggga agggactgga gtggcttgga tttattcata gcactgggag caccaacacc   180
aaccctccc tcaagagtcg agtcaccatt tcagtagaca cgtccaagaa ccagttctcc    240
ctgaggctga cttctgtgag cgctgcggac acggccgttt attactgtgc gagagccgct   300
tggttagtag gggggagta ctacaactac ggtatggacc tttggggcca agggaccacg    360
gttaccgtct cctca                                                    375

SEQ ID NO: 212         moltype = DNA   length = 321
FEATURE                Location/Qualifiers
misc_feature           1..321
                       note = Synthetic
source                 1..321
                       mol_type = other DNA
                       organism = synthetic construct
SEQUENCE: 212
cagtctgccc tgactcagcc cgcctccgtt tctgggtctc ctggacagtc gatcaccctc    60
tcctgcactg taggcggtaa taagtttgtc tcttggtatc aacaacaccc aggcaaagcc   120
cccaaactca ttatttctga tttcactgat cggccctcag gggtctctag tcgcttctct   180
ggctccaagt ctggcaacac ggcctccctg accatctctg ggctcagcc tgacgacgag    240
gctacttatt tctgcagttc ttacgcaagc accagcactt ctctttgggt cttcggcggg   300
gggaccaagc tgaccgtcct a                                             321

SEQ ID NO: 213         moltype = DNA   length = 381
FEATURE                Location/Qualifiers
misc_feature           1..381
                       note = Synthetic
source                 1..381
                       mol_type = other DNA
                       organism = synthetic construct
SEQUENCE: 213
caggtgcagc tggtggaatc tgggggaggc gtggtccagc ctgggaggtc cctgagactc    60
tcctgtgtag cgtctggatt caccttcagt agttatggca tgcactgggt ccgccaggct   120
ccaggcaagg ggctggagtg ggtggcattt atatggtatg atggaactat tcaatactat   180
ggagactccg tgaagggccg attcatcatc tccagagaca attccaggaa tacgctgtat   240
ctacaaatga acagcctgag agccgaggac acggctgtgt attactgtgc gagcactctt   300
taccgaaacg gtgactacgg gtcagggtcc cggaccccgg acgactactg gggccaggga   360
accctggtca ccgtctcttc a                                             381

SEQ ID NO: 214         moltype = DNA   length = 321
FEATURE                Location/Qualifiers
misc_feature           1..321
                       note = Synthetic
source                 1..321
                       mol_type = other DNA
                       organism = synthetic construct
SEQUENCE: 214
ggcatccagt tgacccagtc tccatccttc ctgtctgcat ctgtaggaga cagagtcacc    60
atcacttgcc gggccagtca gggcatttac acttatttag cctggtatca gcaaaaacca   120
gggaaagccc ctaagctcct ggtctatgtt gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt accctctcac ttttggccag    300
gggaccaagc tggagatcaa a                                             321

SEQ ID NO: 215         moltype = AA    length = 6
FEATURE                Location/Qualifiers
REGION                 1..6
                       note = Synthetic construct
source                 1..6
                       mol_type = protein
                       organism = synthetic construct
SEQUENCE: 215
GGGGGG                                                                6

SEQ ID NO: 216         moltype = AA    length = 5
FEATURE                Location/Qualifiers
REGION                 1..5
                       note = Synthetic construct
source                 1..5
                       mol_type = protein
                       organism = synthetic construct
SEQUENCE: 216
GGGGT                                                                 5

SEQ ID NO: 217         moltype = AA    length = 6
FEATURE                Location/Qualifiers
REGION                 1..6
                       note = Synthetic construct
source                 1..6
```

```
SEQUENCE: 217
GGGPPP                                                                        6

SEQ ID NO: 218         moltype = AA  length = 7
FEATURE                Location/Qualifiers
REGION                 1..7
                       note = Synthetic construct
source                 1..7
                       mol_type = protein
                       organism = synthetic construct
SEQUENCE: 218
GGGAPPP                                                                       7
```

The invention claimed is:

1. A non-naturally occurring chimeric antibody or antigen binding fragment comprising six complementarity determining regions (CDRs) of antibody 9.20.1A02,
wherein the CDRs comprise the three light chain CDRs, wherein light chain CDR 1 comprises the amino acid sequence of (SEQ ID NO: 174) YSNIGAGYD; light chain CDR2 comprises the amino acid sequence of (SEQ ID NO: 175) DNVH; and light chain CDR3 comprises the amino acid sequence of (SEQ ID NO: 176) QSYDSRLRDQWV; and,
wherein the CDRs comprise the three heavy chain CDRs, wherein heavy chain CDR 1 comprises the amino acid sequence of (SEQ ID NO: 178) GITLSGVW; CDR 2 comprises the amino acid sequence of ((SEQ ID NO: 179) IKSTSDGGRA, and CDR 3 comprises the amino acid sequence of (SEQ ID NO: 180) FTRVQRDGTKDDF, and
wherein the antibody or antigen binding fragment thereof binds to an epitope expressed in an Ebola virus particle.

2. The antibody or antigen binding fragment of claim 1 comprising a human constant domain from an immunoglobulin constant region (Fc) having one or more of the following mutations: G236A, S239D, A330L, I332E, S267E, L328F, P238D, H268F, S324T, S228P, G236R, L328R, L234A, L235A, M252Y, S254T, T256E, M428L, N434S, A330L, N297A, and N297Q wherein the Fc mutations are in reference to positions in amino acid sequence (SEQ ID NO: 50) STKGPSVFPLAPSSKSTSGGTAAL-GCLVKDYFPEPVTVSWNSGALTSGVHTFPAVLQSSGLYS-LSSVVTVPSSSLGTQTYICNVNHKPSNTKVDKKVE-PKSCDKTHTCPPCPAPELLGGP SVFLFPPKPKDTLMISRTPEVTCVVVDVSHEDPE-VKFNWYVDGVEVHNAKTKPREEQY NSTYRVVSVLTVLHQDWLNGKEYKCKVSNKALPA-PIEKTISKAKGQPREPQVYTLPPSR DE, wherein the N-terminal amino acid serine (S) is position 119.

3. The antibody or antigen fragment of claim 1 comprising at least one amino acid substitution in the heavy chain constant region that is not present in naturally occurring antibodies comprising the six CDRs.

4. The antibody of claim 1, wherein the heavy chain comprises a sequence in a constant region that is different from any sequences present in naturally occurring antibodies for which the light chain variable region comprises the three light chain CDRs and the heavy chain variable region comprise the three heavy chain CDRs.

5. The antibody or antigen binding fragment thereof of claim 1, wherein the epitope expressed on an Ebola virus particle is arrayed on a surface, expressed on the surface of a cell, or expressed at an endogenous or transfected concentration, and the antibody or antigen binding fragment is bound to the epitope.

6. A nucleic acid molecule encoding an antibody or antigen binding fragment of claim 1.

7. An expression vector comprising a nucleic acid molecule encoding the antibody or the antigen binding fragment of claim 1.

8. A recombinant protein expression system comprising isolated host cells expressing the nucleic acid molecule of the expression vector of claim 7, wherein the isolated host cells are prokaryotic cells or eukaryotic cells.

9. A pharmaceutical composition comprising the antibody or antigen binding fragment thereof of claim 1, and a physiologically acceptable carrier or excipient.

10. A method of detection Ebola virus infection, comprising: (a) assaying the expression of Ebola virus epitope in cells or in a tissue sample of a subject using the antibody or antigen binding fragment thereof of claim 1 and (b) comparing the level of the Ebola virus epitope with a control level, wherein an increase in the assayed level of Ebola virus compared to the control level is indicative of the infection.

11. A method of treating an Ebola virus infection comprising administering an effective amount of a pharmaceutical composition of claim 8 to a subject in need thereof.

* * * * *